US011751606B2

(12) United States Patent
Gallagher et al.

(10) Patent No.: US 11,751,606 B2
(45) Date of Patent: *Sep. 12, 2023

(54) HEATING ENGINE CONTROL ALGORITHM FOR NON-NICOTINE E-VAPOR DEVICE

(71) Applicant: Altria Client Services LLC, Richmond, VA (US)

(72) Inventors: Niall Gallagher, Richmond, VA (US); William Wykeham, Richmond, VA (US); Raymond W. Lau, Richmond, VA (US); Eric Hawes, Glen Allen, VA (US); Terry Bache, Richmond, VA (US); Rangaraj S. Sundar, Richmond, VA (US); Jarrett Keen, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 752 days.

This patent is subject to a terminal disclaimer.

(21) Appl. No.: 16/786,181

(22) Filed: Feb. 10, 2020

(65) Prior Publication Data

US 2021/0244095 A1 Aug. 12, 2021

(51) Int. Cl.
*A24F 40/46* (2020.01)
*A24F 40/60* (2020.01)
(Continued)

(52) U.S. Cl.
CPC .............. *A24F 40/46* (2020.01); *A24F 40/51* (2020.01); *A24F 40/53* (2020.01); *A24F 40/60* (2020.01); *A24F 40/57* (2020.01)

(58) Field of Classification Search
CPC .......... A24F 40/46; A24F 40/50; A24F 40/53; A24F 40/57
See application file for complete search history.

(56) References Cited

U.S. PATENT DOCUMENTS

| 5,595,706 A | 1/1997 | Sikka et al. |
| 9,282,772 B2 | 3/2016 | Tucker et al. |
| (Continued) | | |

FOREIGN PATENT DOCUMENTS

| CN | 203643774 U | 6/2014 |
| DE | 102006004484 A1 | 8/2007 |
| (Continued) | | |

OTHER PUBLICATIONS

International Search Report and Written Opinion of the International Searching Authority for International Application No. PCT/EP2021/053241 dated Jul. 27, 2021.

(Continued)

*Primary Examiner* — Hae Moon Hyeon
(74) *Attorney, Agent, or Firm* — Harness, Dickey & Pierce, P. L. C.

(57) ABSTRACT

A method of controlling a heater of a device including a removable container that stores a material includes detecting, from the removable container, power information indicating a first operating point and a second operating point; and supplying power to the heater based on the detected power information by, determining a first amount of power based on the first operating point, supplying the first amount of power to the heater during a first operation mode of the heater, determining a second amount of power based on the second operating point, and supplying the second amount of power to the heater during a second operation mode of the heater, the second amount of power being higher than the first amount of power, the device being a non-nicotine e-vaping device or a heat-not-burn aerosol-generating device, the material being a non-nicotine pre-vapor formulation or an aerosol-forming substrate.

21 Claims, 36 Drawing Sheets

(51) Int. Cl.
    *A24F 40/53*     (2020.01)
    *A24F 40/51*     (2020.01)
    *A24F 40/57*     (2020.01)

(56) References Cited

U.S. PATENT DOCUMENTS

| | | |
|---|---|---|
| 9,980,514 B2 * | 5/2018 | Malamud ............ H05B 1/0244 |
| 2013/0042865 A1 | 2/2013 | Monsees et al. |
| 2014/0000638 A1 | 1/2014 | Sebastian et al. |
| 2014/0014126 A1 | 1/2014 | Peleg et al. |
| 2014/0096782 A1 | 4/2014 | Ampolini et al. |
| 2014/0123990 A1 | 5/2014 | Timmermans |
| 2014/0246035 A1 | 9/2014 | Minskoff et al. |
| 2014/0261486 A1 | 9/2014 | Potter et al. |
| 2014/0261491 A1 | 9/2014 | Hawes |
| 2014/0270727 A1 | 9/2014 | Ampolini et al. |
| 2014/0283825 A1 | 9/2014 | Buchberger |
| 2014/0318560 A1 | 10/2014 | Hon |
| 2014/0332016 A1 | 11/2014 | Bellinger et al. |
| 2014/0345635 A1 | 11/2014 | Rabinowitz et al. |
| 2015/0027459 A1 | 1/2015 | Collett et al. |
| 2015/0047656 A1 | 2/2015 | Robinson et al. |
| 2015/0114409 A1 | 4/2015 | Brammer et al. |
| 2015/0320116 A1 | 11/2015 | Bleloch et al. |
| 2015/0335074 A1 | 11/2015 | Leung |
| 2015/0359263 A1 | 12/2015 | Bellinger |
| 2015/0359266 A1 | 12/2015 | Memari et al. |
| 2016/0021930 A1 | 1/2016 | Minskoff et al. |
| 2016/0053988 A1 | 2/2016 | Quintana |
| 2016/0057811 A1 | 2/2016 | Alarcon et al. |
| 2017/0042251 A1 | 2/2017 | Yamada et al. |
| 2017/0108840 A1 | 4/2017 | Hawes et al. |
| 2017/0231282 A1 | 8/2017 | Bowen et al. |
| 2018/0104214 A1 | 4/2018 | Raichman |
| 2019/0104764 A1 | 4/2019 | Tucker et al. |
| 2019/0387796 A1 | 12/2019 | Cohen |
| 2020/0229509 A1 | 7/2020 | Griscik et al. |
| 2020/0405980 A1 | 12/2020 | Griscik et al. |
| 2021/0045457 A1 | 2/2021 | Weigensberg et al. |
| 2021/0195948 A1 * | 7/2021 | Bilat ....................... A24F 40/46 |
| 2021/0244094 A1 * | 8/2021 | Gallagher ............... A24F 40/50 |

FOREIGN PATENT DOCUMENTS

| | | |
|---|---|---|
| DE | 202013010986 U1 | 2/2014 |
| EP | 2967140 A1 | 1/2016 |
| WO | WO-2014/066730 A1 | 5/2014 |
| WO | WO-2015/038981 A2 | 3/2015 |
| WO | WO-2015/107552 A1 | 7/2015 |
| WO | WO-2015/038981 A3 | 10/2015 |
| WO | WO-2016/030661 A1 | 3/2016 |
| WO | WO-2018/185460 A1 | 10/2018 |
| WO | WO-2019/104227 A1 | 5/2019 |
| WO | WO-2019/141577 A1 | 7/2019 |

OTHER PUBLICATIONS

Madgwick, S., "An efficient orientation filter for intertial and intertial/magnetic sensor arrays," Apr. 2010, x-io Technologies Limited, https://x-io.co.uk/res/doc/madgwick_internal_report.pdf.

Mason, T. et al., "A practical approach to replicating human puff profiles in a mechanical smoking machine." 2005, SPPT 35, http://www.cerulean.com/media/315639/A-practical-approach-to-replicating-human-puff-profiles-in-a-mechanical-smoking-machine.pdf.

"Application Guide—Electric Heaters—Power Calculations—calculations for Required Heat Energy", Watlow, 2006 <https://www.watlow.com/reference/files/powercalculations.pdf>, retrieved Jul. 2020.

International Search Report and Written Opinion of the International Searching Authority for International Application No. PCT/US2021/015018 dated Jul. 9, 2021.

International Preliminary Report on Patentability for International Application No. PCT/EP2021/053241 dated Mar. 28, 2022.

Invitation to Pay Fees for PCT/EP2021/053241 dated Feb. 15, 2022.

Notification Concerning Transmittal of International Preliminary Report on Patentability and Written Opinion of the International Searching Authority dated Aug. 25, 2022 issued in corresponding international patent application No. PCT/US2021/015018.

International Search Report for International Application No. PCT/EP2021/053241 dated May 17, 2021.

U.S. Non-Final Office Action for Corresponding U.S. Appl. No. 16/785,785, dated Jan. 17, 2023.

* cited by examiner

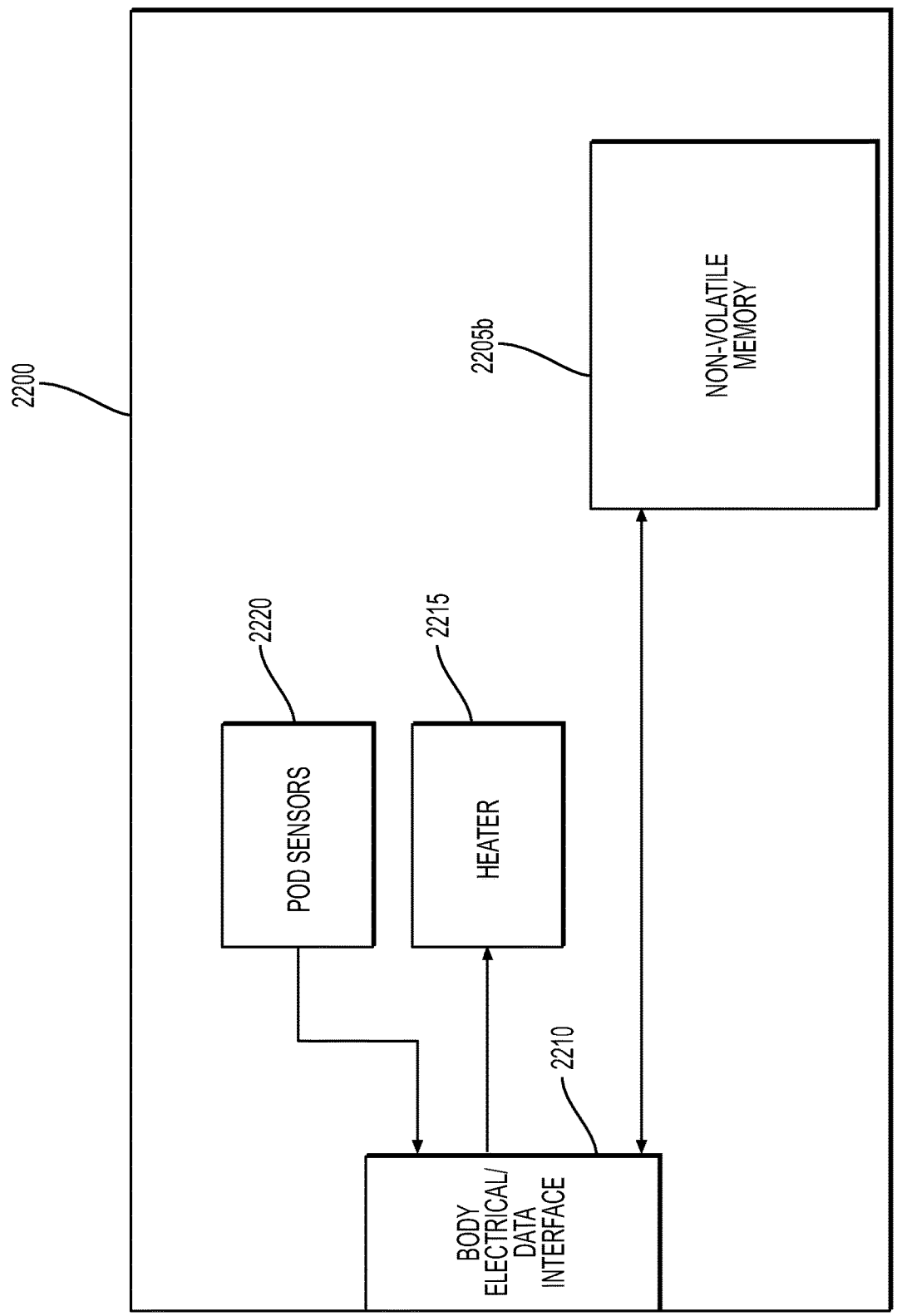

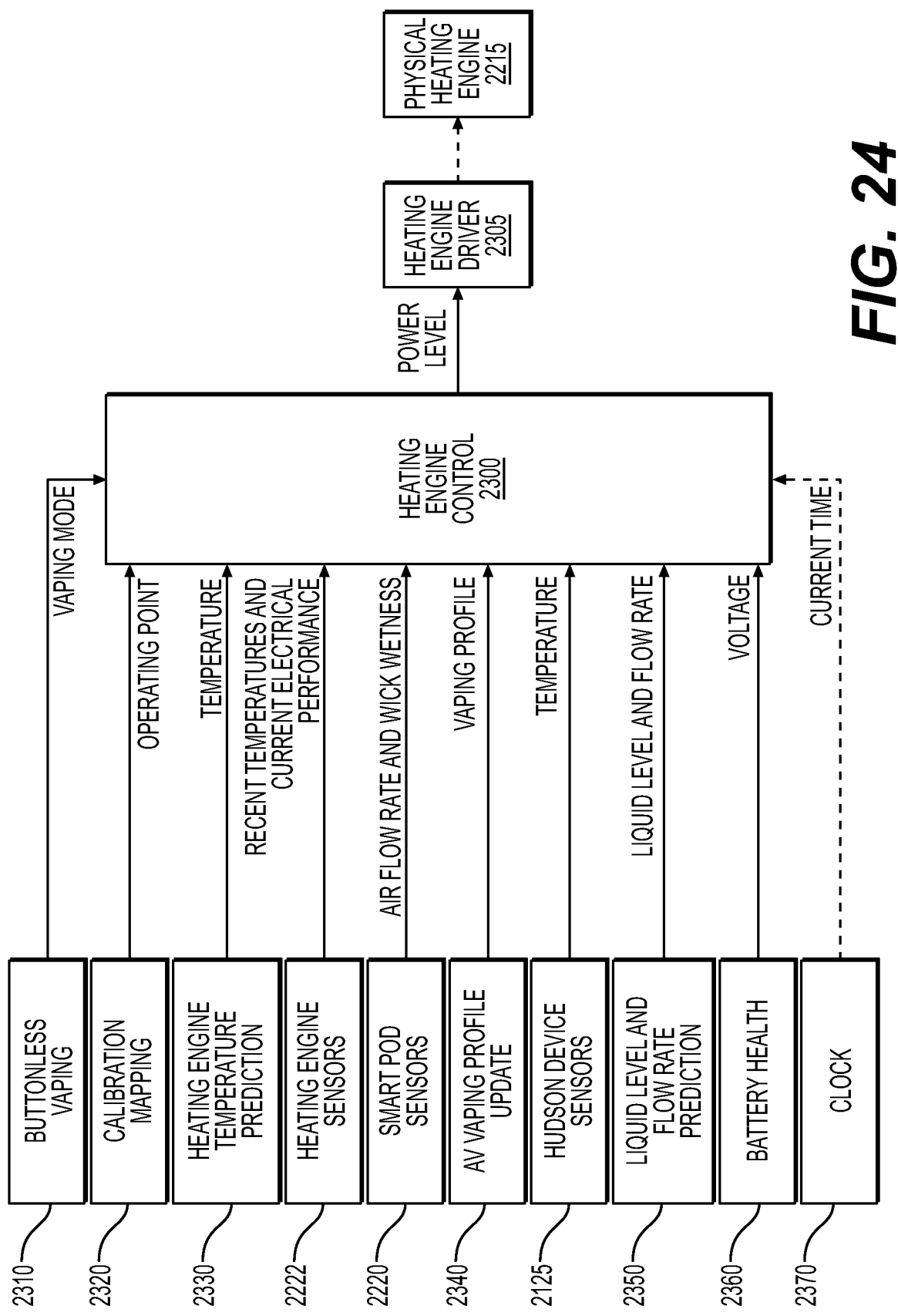

HEATING ENGINE CONTROL ALGORITHM FOR NON-NICOTINE E-VAPOR DEVICE

BACKGROUND

Field

The present disclosure relates to non-nicotine electronic vapor devices including self-contained articles including non-nicotine pre-vapor formulations.

Description of Related Art

Non-nicotine electronic vaping devices are used to vaporize a non-nicotine pre-vapor formulation material into a non-nicotine vapor. These non-nicotine electronic vaping devices may be referred to as non-nicotine e-vapor devices. Non-nicotine e-vapor devices include a heater which vaporizes the non-nicotine pre-vapor formulation material to produce non-nicotine vapor. A non-nicotine e-vapor device may include several e-vaping elements including a power source, a cartridge or non-nicotine e-vaping tank including the heater and along with a reservoir capable of holding the non-nicotine pre-vapor formulation material.

SUMMARY

According to at least some example embodiments, a method of controlling a heater of a device, the device including a removable container that stores a material, includes detecting, from the removable container, power information indicating a first operating point and a second operating point; and supplying power to the heater based on the detected power information by, determining a first amount of power based on the first operating point, supplying the first amount of power to the heater during a first operation mode of the heater, determining a second amount of power based on the second operating point, and supplying the second amount of power to the heater during a second operation mode of the heater, the second amount of power being higher than the first amount of power, the device being a non-nicotine e-vaping device or a heat-not-burn aerosol-generating device, the material being a non-nicotine pre-vapor formulation or an aerosol-forming substrate.

The first amount of power supplied during the first operation mode may be an amount that causes the heater to heat the material stored in the device to a temperature below a dispersion temperature of the material, and the second amount of power supplied during the second operation mode may be an amount that causes the heater to heat the material stored in the device to a temperature equal to, or greater than, the dispersion temperature of the material, the dispersion temperature being a boiling point of the material, when the material is a non-nicotine pre-vapor formulation, the dispersion temperature being an aerosolization temperature of the material, when the material is an aerosol-forming substrate.

The material may be stored in the removable container.

The removable container may include the heater.

The power information may include a plurality of operating points that correspond, respectively, to a plurality of coarse preference levels, and the method may further include receiving, via one or more touch sensors located on the device, a selection of a coarse preference level, from among the plurality of coarse preference levels; and selecting, as the second operating point, the operating point, from among the plurality of operating points, that corresponds to the selected coarse preference level.

The determining of the second amount of power may include receiving, by the device from an external source, a selection of a fine preference level, from among a plurality of fine preference levels; and determining the second amount of power based on the selected second operating point and the selected fine preference level.

The external source may be a wireless communication device, and the receiving of the selection of the fine preference level may include receiving, by the device, the selection of the fine preference level via a wireless communication link between the device and the external source.

The power information may include a first plurality of operating points that correspond, respectively, to a plurality of coarse preference levels, and the method may further include receiving, via one or more touch sensors located on the device, a selection of a coarse preference level, from among the plurality of coarse preference levels; and selecting, as the first operating point, the operating point, from among the first plurality of operating points, that corresponds to the selected coarse preference level.

The determining of the first amount of power may include receiving, by the device from an external source, a selection of a fine preference level, from among a plurality of fine preference levels; and determining the first amount of power based on the selected first operating point and the selected fine preference level.

The external source may be a wireless communication device, and the receiving of the selection of the fine preference level may include receiving, by the device, the selection of the fine preference level via a wireless communication link between the device and the external source.

The power information may include a second plurality of operating points that correspond, respectively, to the plurality of coarse preference levels, and the method may further include selecting, as the second operating point, the operating point, from among the second plurality of operating points, that corresponds to the selected coarse preference level.

The determining of the second amount of power may include determining the second amount of power based on the selected second operating point and the selected fine preference level.

The external source may be a wireless communication device, and the receiving of the selection of the fine preference level may include receiving, by the device, the selection of the fine preference level via a wireless communication link between the device and the external source.

The detecting of the power information may include reading, by the device, the power information from an image located on the removable container.

The image may include a quick response (QR) code, and the reading of the power information may include reading, by the device, the power information from the QR code located on the removable container.

The removable container may include memory, the memory of the removable container may store data that includes the power information, and the detecting of the power information may include reading, by the device, the power information from the memory of the removable container.

According to at least some example embodiments, a method of controlling a heater of a device, the device being configured to hold a removable container that stores a material, includes receiving, via one or more touch sensors located on the device, a selection of a coarse preference level, from among a plurality of coarse preference levels; receiving, by the device from an external source, a selection of a fine preference level, from among a plurality of fine preference levels; determining a first amount of power based on the selected coarse preference level and the selected fine preference level; and supplying the determined first amount of power to the heater, the device being a non-nicotine e-vaping device or a heat-not-burn aerosol-generating device, the material being a non-nicotine pre-vapor formulation or an aerosol-forming substrate.

The external source may be a wireless communication device, and the receiving of the selection of the fine preference level may include receiving, by the device, the selection of the fine preference level via a wireless communication link between the device and the external source.

The method may further include receiving, by the device, a first removable container via insertion of the first removable container into the device, the first removable container containing a material; detecting, by the device, a first formulation type as a type of the material of the first removable container; and storing, in association with the detected first formulation type, the selected coarse preference level and the selected fine preference level in a memory of the device, and wherein the determined first amount of power may be an amount that causes the heater to heat the material stored in the first removable container to a temperature equal to, or greater than, a dispersion temperature of the material stored in the first removable container, the dispersion temperature being a boiling point of the material stored in the first removable container, when the material stored in the first removable container is a non-nicotine pre-vapor formulation, the dispersion temperature being an aerosolization temperature of the material stored in the first removable container, when the material stored in the first removable container is an aerosol-forming substrate.

The detecting may include reading, by the device, formulation type information from an image located on the first removable container; and detecting the first formulation type as the type of the material of the first removable container based on the read formulation type information.

The image may include a QR code, and the reading of the formulation type information may include reading, by the device, the formulation type information from the QR code located on the first removable container.

The first removable container may include memory, the memory of the first removable container may store data that includes formulation type information, and the detecting may include reading, by the device, the formulation type information from the memory of the first removable container; and detecting the first formulation type as the type of the material of the first removable container based on the read formulation type information.

The method may further include receiving, by the device, a second removable container via insertion of the second removable container into the device, the second removable container containing a material; detecting, by the device, the first formulation type as a type of the material of the second removable container; based on the detecting of the first formulation type as the type of the material of the second removable container, reading, from the memory of the device, the coarse preference level and the fine preference level that were previously stored in the memory of the device in association with the first formulation type; determining a second amount of power based on the read coarse preference level and the read fine preference level; and causing the heater to heat the material stored in the second removable container to a temperature equal to, or greater than, a dispersion temperature of the material stored in the second removable container by supplying the determined second amount of power to the heater, the dispersion temperature being a boiling point of the material stored in the second removable container, when the material stored in the second removable container is a non-nicotine pre-vapor formulation, the dispersion temperature being an aerosolization temperature of the material stored in the second removable container, when the material stored in the second removable container is an aerosol-forming substrate.

The detecting may include reading, by the device, formulation type information from an image located on the second removable container; and detecting the first formulation type as the type of the material of the second removable container based on the read formulation type information.

The image may include a QR code, and the reading of the formulation type information may include reading, by the device, the formulation type information from the QR code located on the second removable container.

The second removable container may include memory, the memory of the second removable container may store data that includes formulation type information, and the detecting may include reading, by the device, the formulation type information from the memory of the first removable container; and detecting the first formulation type as the type of the material of the second removable container based on the read formulation type information.

According to at least some example embodiments, a method of controlling a heater of a device, the device being configured to hold a removable container that stores a material, includes receiving, by the device, a plurality of vaping preference levels; determining, by the device, a current time; determining, by the device, a predicted vaping preference level based on the determined current time; determining an amount of power to supply to the heater based on the predicted vaping preference level; and supplying the determined amount of power to the heater, the device being a non-nicotine e-vaping device or a heat-not-burn aerosol-generating device, the material being a non-nicotine pre-vapor formulation or an aerosol-forming substrate.

The plurality of vaping preference levels may include first received vaping preference levels received by the device during a first time of day and second received vaping preference levels received by the device during a second time of day, and the determining of the predicted vaping preference level may include determining, by the device, the predicted vaping preference level based on the first received vaping preference levels, when the determined current time is within the first time of day; and determining, by the device, the predicted vaping preference level based on the second received vaping preference levels, when the determined current time is within the second time of day.

The receiving of the plurality of vaping preference levels may include receiving one or more of the plurality of vaping preference levels via one or more touch sensors located on the device.

The receiving of the plurality of vaping preference levels may include receiving one or more of the plurality of vaping preference levels from an external source.

The external source may be a wireless communication device, and the receiving of the one or more of the plurality of vaping preference levels may include receiving, by the device, the one or more of the plurality of vaping preference levels via a wireless communication link between the device and the external source.

According to at least some example embodiments, a method of controlling a heater of a device, the device being configured to hold a removable container that stores a material, includes receiving, via one or more touch sensors located on the device, a selection of a coarse preference level, from among a plurality of coarse preference levels; detecting, from the removable container included in the device, power information indicating a plurality of operating points corresponding, respectively, to the plurality of coarse preference levels; selecting, as a first operating point, the operating point, from among the plurality of operating points, that corresponds to the selected coarse preference level; determining a first amount of power based on the first operating point; and supplying the determined first amount of power to the heater, the device being a non-nicotine e-vaping device or a heat-not-burn aerosol-generating device, the material being a non-nicotine pre-vapor formulation or an aerosol-forming substrate.

The first amount of power may be an amount that causes the heater to heat the material stored in the device to a temperature below a dispersion temperature of the material, the dispersion temperature being a boiling point of the material, when the material is a non-nicotine pre-vapor formulation, the dispersion temperature being an aerosolization temperature of the material, when the material is an aerosol-forming substrate.

The first amount of power may be an amount that causes the heater to heat the material stored in the device to a temperature equal to, or greater than, a dispersion temperature point of the material, the dispersion temperature being a boiling point of the material, when the material is a non-nicotine pre-vapor formulation, the dispersion temperature being an aerosolization temperature of the material, when the material is an aerosol-forming substrate.

The detecting of the power information may include reading, by the device, the power information from an image located on the removable container.

The image may include a QR code, and the reading of the power information may include reading, by the device, the power information from the QR code located on the removable container.

The removable container may include memory, the memory of the removable container may store data that includes the power information, and the detecting of the power information may include reading, by the device, the power information from the memory of the removable container.

According to at least some example embodiments, a method of controlling a heater of a device, the device being configured to hold a removable container that stores a material, includes determining a heater temperature value; obtaining a target temperature value; and controlling, by a Proportional Integral Derivative (PID) controller, a level of power provided to the heater, based on the heater temperature value and the target temperature value, the device being a non-nicotine e-vaping device or a heat-not-burn aerosol-generating device, the material being a non-nicotine pre-vapor formulation or an aerosol-forming substrate.

The determining of the heater temperature value may include obtaining one or more electrical attributes of the heater; determining a resistance of the heater based on the obtained one or more electrical attributes; and obtaining, from a look-up table (LUT), based on the determined resistance, a first temperature value.

The LUT may store a plurality of temperature values that correspond, respectively, to a plurality of heater resistances, the obtained first temperature value may be the temperature value, from among the plurality of temperature values stored in the LUT, that corresponds to the determined resistance, and the heater temperature value may be the obtained first temperature value.

The obtaining of the target temperature value may include detecting, from a removable container included in the device, power information indicating a plurality of temperature setpoints; determining a current operation mode of the device; and selecting, as the target temperature value, a temperature setpoint, from among a plurality of temperature setpoints, that corresponds to the determined current operation mode of the device.

The controlling of the level of power provided to the heater may include controlling, by a PID controller, a level of power provided to the heater such that a magnitude of a difference between the target temperature value and the heater temperature value is reduced.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 22B illustrates an example of the pod system of FIG. 22A in which a cryptographic coprocessor is omitted, according to an example embodiment.

FIG. 24 is a diagram illustrating a heating engine control algorithm and related inputs according to at least one example embodiment.

DETAILED DESCRIPTION

Figure 1:
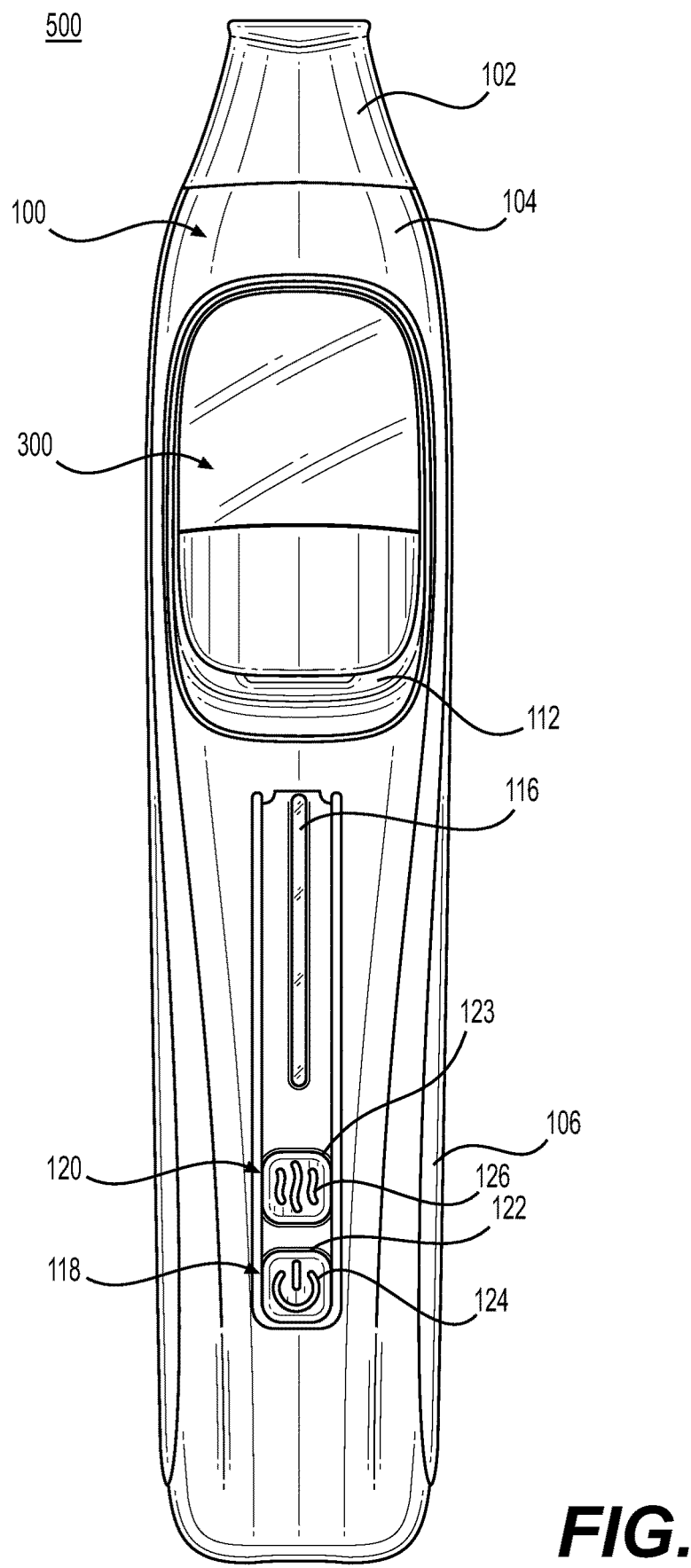
FIG. 1 is a front view of a non-nicotine e-vaping device according to an example embodiment.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, elements, regions, layers and/or sections, these elements, elements, regions, layers, and/or sections should not be limited by these terms. These terms are only used to distinguish one element, element, region, layer, or section from another region, layer, or section. Thus, a first element, element, region, layer, or section discussed below could be termed a second element, element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or elements, but do not preclude the presence or addition of one or more other features, integers, steps, operations, elements, elements, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. The regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Example Non-Nicotine E-Vapor Device Structure

A "non-nicotine e-vapor device" as used herein may be referred to on occasion using, and considered synonymous with, any of the terms: non-nicotine e-vaping device, non-nicotine e-vapor apparatus, and non-nicotine e-vaping apparatus. Pod assemblies (e.g., pod assembly 300) may also be referred to, herein, as a "pods" or "removable pods."

Figure 2:
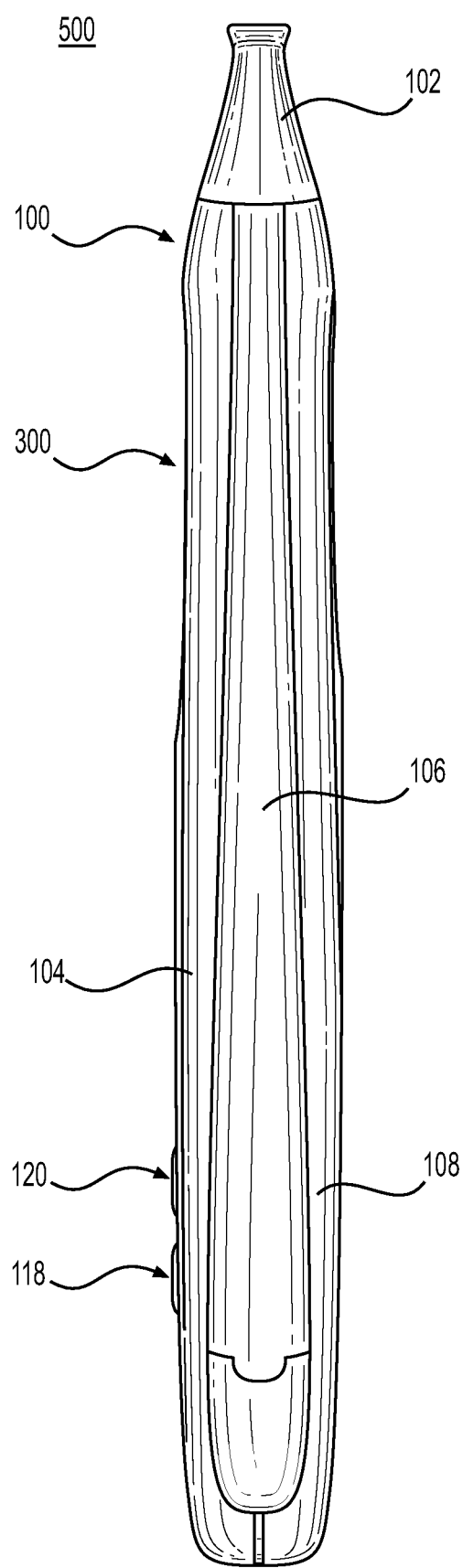
FIG. 2 is a side view of the non-nicotine e-vaping device of FIG. 1.
Figure 3:
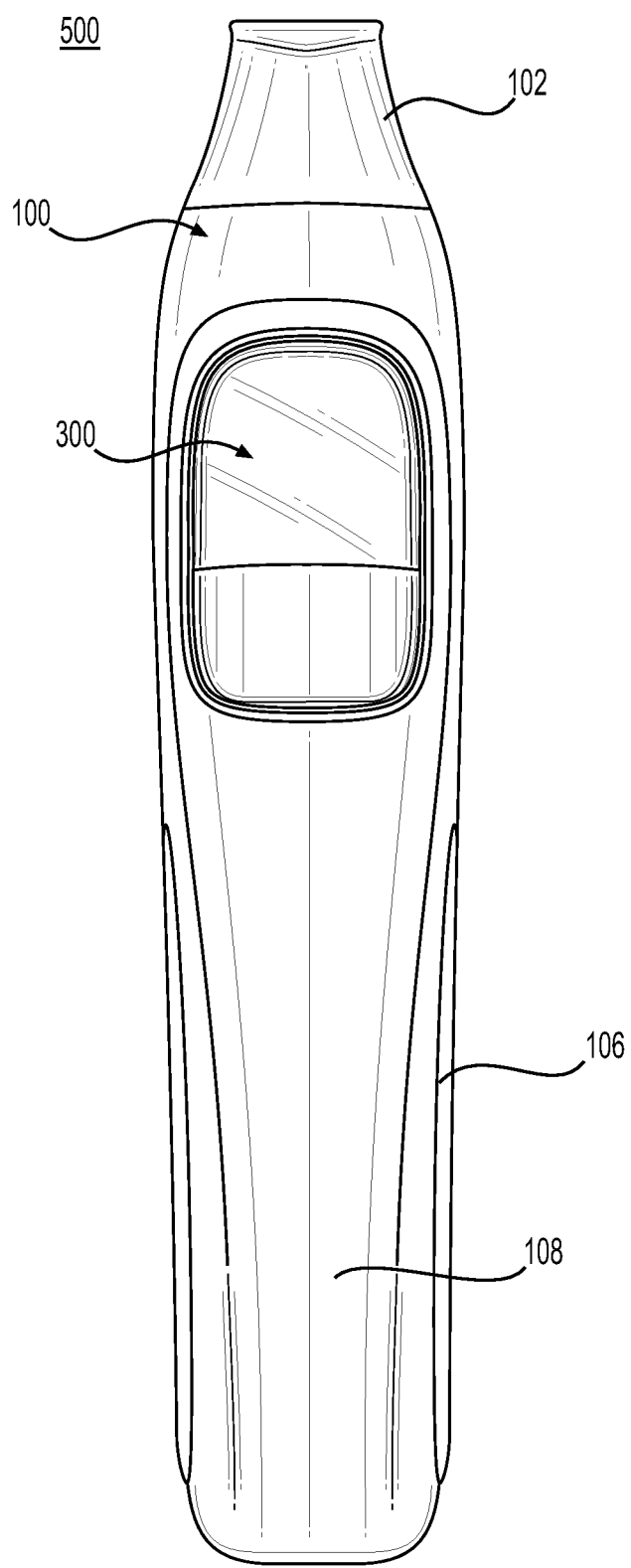
FIG. 3 is a rear view of the non-nicotine e-vaping device of FIG. 1.

FIG. 1 is a front view of a non-nicotine e-vaping device according to an example embodiment. FIG. 2 is a side view of the non-nicotine e-vaping device of FIG. 1. FIG. 3 is a rear view of the non-nicotine e-vaping device of FIG. 1. Referring to FIGS. 1-3, a non-nicotine e-vaping device 500 includes a device body 100 that is configured to receive a pod assembly 300. The pod assembly 300 is a modular article configured to hold a non-nicotine pre-vapor formulation. As used herein, the term "non-nicotine pre-vapor formulation" (or "non-nicotine pre-vapor formulation material") refers to a material (or combination of materials) that does not contain nicotine and may be transformed into a non-nicotine vapor. For example, the non-nicotine pre-vapor formulation may be a liquid, solid, and/or gel formulation including, but not limited to, water, oils, emulsions, beads, solvents, active ingredients, ethanol, plant extracts (e.g., cannabinoids), natural or artificial flavors, and/or vapor formers such as glycerin and propylene glycol. During vaping, the non-nicotine e-vaping device 500 is configured to heat the non-nicotine pre-vapor formulation to generate a non-nicotine vapor. As referred to herein, a "vapor" is any matter generated or outputted from any non-nicotine e-vaping device according to any of the example embodiments disclosed herein. The non-nicotine pre-vapor formulation may also be as described in U.S. application Ser. No. 16/540,433, titled "NON-NICOTINE E-VAPING SECTION, AND NON-NICOTINE E-VAPING DEVICE INCLUDING NON-NICOTINE E-VAPING SECTION", filed Aug. 14, 2019, the entire content of which is incorporated herein by reference.

The device body 100 includes a front cover 104, a frame 106, and a rear cover 108. The front cover 104, the frame 106, and the rear cover 108 form a device housing that encloses mechanical components, electronic components, and/or circuitry associated with the operation of the non-nicotine e-vaping device 500. For instance, the device housing of the device body 100 may enclose a power source configured to power the non-nicotine e-vaping device 500, which may include supplying an electric current to the pod assembly 300. In addition, when assembled, the front cover 104, the frame 106, and the rear cover 108 may constitute a majority of the visible portion of the device body 100.

The front cover 104 (e.g., first cover) defines a primary opening configured to accommodate a bezel structure 112. The bezel structure 112 defines a through hole 150 configured to receive the pod assembly 300. The through hole 150 is discussed herein in more detail in connection with, for instance, FIG. 9.

The front cover 104 also defines a secondary opening configured to accommodate a light guide arrangement. The secondary opening may resemble a slot (e.g., segmented slot), although other shapes are possible depending on the shape of the light guide arrangement. In an example embodiment, the light guide arrangement includes a light guide lens 116. Furthermore, the front cover 104 defines a tertiary opening and a quaternary opening configured to accommodate a first button 118 and a second button 120. Each of the tertiary opening and the quaternary opening may resemble a rounded square, although other shapes are possible depending on the shapes of the buttons. A first button housing 122 is configured to expose a first button lens 124, while a second button housing 123 is configured to expose a second button lens 126.

The operation of the non-nicotine e-vaping device 500 may be controlled by the first button 118 and the second button 120. For instance, the first button 118 may be a power button, and the second button 120 may be an intensity button. Although two buttons are shown in the drawings in connection with the light guide arrangement, it should be understood that more (or less) buttons may be provided depending on the available features and desired user interface. The frame 106 (e.g., base frame) is the central support structure for the device body 100 (and the non-nicotine e-vaping device 500 as a whole). The frame 106 may be referred to as a chassis. The frame 106 includes a proximal end, a distal end, and a pair of side sections between the proximal end and the distal end. The proximal end and the distal end may also be referred to as the downstream end and the upstream end, respectively. As used herein, "proximal" (and, conversely, "distal") is in relation to an adult vaper during vaping, and "downstream" (and, conversely, "upstream") is in relation to a flow of the vapor. A bridging section may be provided between the opposing inner surfaces of the side sections (e.g., about midway along the length of the frame 106) for additional strength and stability. The frame 106 may be integrally formed so as to be a monolithic structure.

With regard to material of construction, the frame 106 may be formed of an alloy or a plastic. The alloy (e.g., die cast grade, machinable grade) may be an aluminum (Al) alloy or a zinc (Zn) alloy. The plastic may be a polycarbonate (PC), an acrylonitrile butadiene styrene (ABS), or a combination thereof (PC/ABS). For instance, the polycarbonate may be LUPOY SC1004A. Furthermore, the frame 106 may be provided with a surface finish for functional and/or aesthetic reasons (e.g., to provide a premium appearance). In an example embodiment, the frame 106 (e.g., when formed of an aluminum alloy) may be anodized. In another embodiment, the frame 106 (e.g., when formed of a zinc alloy) may be coated with a hard enamel or painted. In another embodiment, the frame 106 (e.g., when formed of a polycarbonate) may be metallized. In yet another embodiment, the frame 106 (e.g., when formed of an acrylonitrile butadiene styrene) may be electroplated. It should be understood that the materials of construction with regard to the frame 106 may also be applicable to the front cover 104, the rear cover 108, and/or other appropriate parts of the non-nicotine e-vaping device 500.

The rear cover 108 (e.g., second cover) also defines an opening configured to accommodate the bezel structure 112. The front cover 104 and the rear cover 108 may be configured to engage with the frame 106 via a snap-fit arrangement.

The device body 100 also includes a mouthpiece 102. The mouthpiece 102 may be secured to the proximal end of the frame 106.

Figure 4:
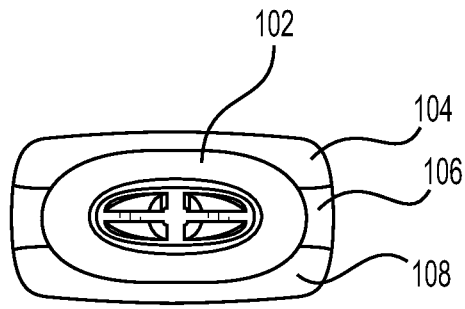
FIG. 4 is a proximal end view of the non-nicotine e-vaping device of FIG. 1.

FIG. 4 is a proximal end view of the non-nicotine e-vaping device of FIG. 1. Referring to FIG. 4, the outlet face of the mouthpiece 102 defines a plurality of vapor outlets. In a non-limiting embodiment, the outlet face of the mouthpiece 102 may be elliptically-shaped.

Figure 5:
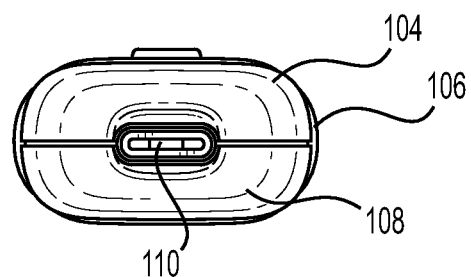
FIG. 5 is a distal end view of the non-nicotine e-vaping device of FIG. 1.

FIG. 5 is a distal end view of the non-nicotine e-vaping device of FIG. 1. Referring to FIG. 5, the distal end of the non-nicotine e-vaping device 500 includes a port 110. The port 110 is configured to receive an electric current (e.g., via a Universal Serial Bus (USB) cable) from an external power source so as to charge an internal power source within the non-nicotine e-vaping device 500. In addition, the port 110 may also be configured to send data to and/or receive data (e.g., via a USB cable) from another non-nicotine e-vaping device or other electronic device (e.g., phone, tablet, computer). Furthermore, the non-nicotine e-vaping device 500 may be configured for wireless communication with another electronic device, such as a phone, via an application software (app) installed on that electronic device. In such an instance, an adult vaper may control or otherwise interface with the non-nicotine e-vaping device 500 (e.g., locate the non-nicotine e-vaping device 500, check usage information, change operating parameters) through the app.

Figure 6:
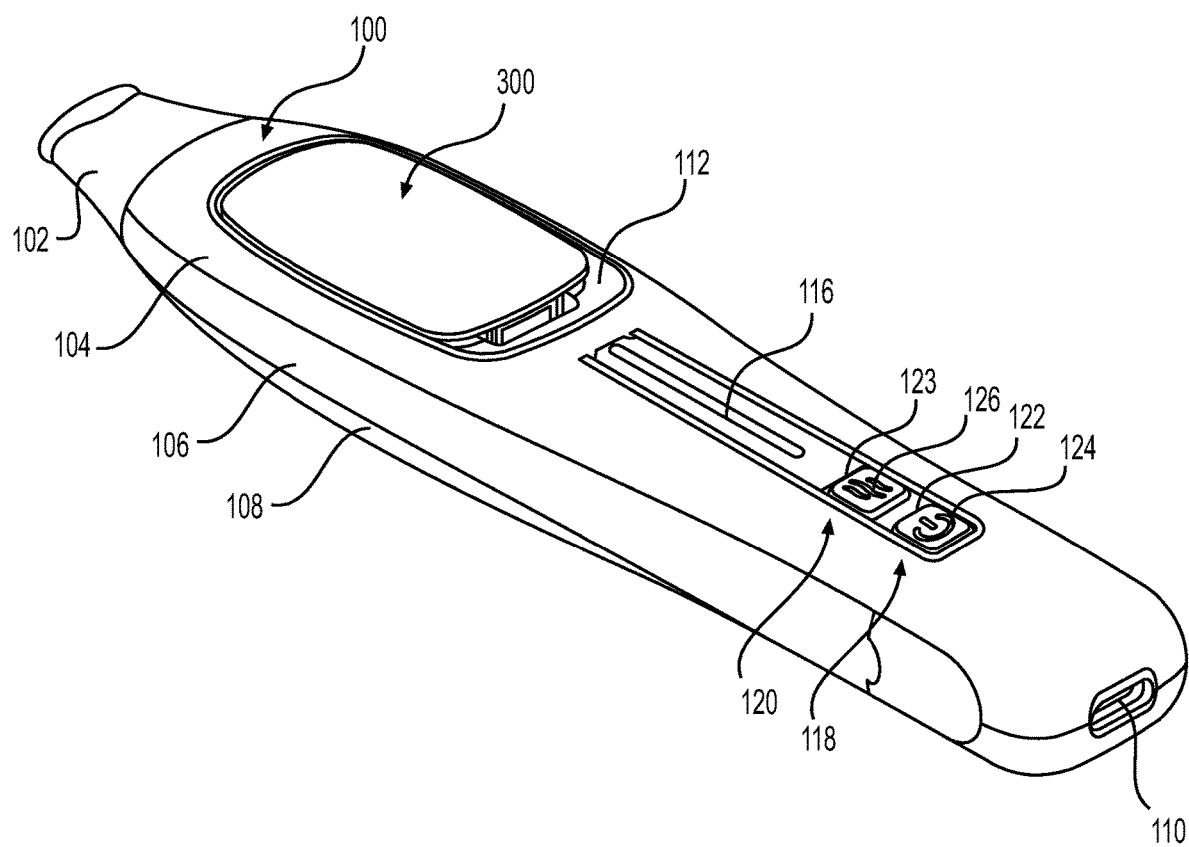
FIG. 6 is a perspective view of the non-nicotine e-vaping device of FIG. 1.
Figure 7:
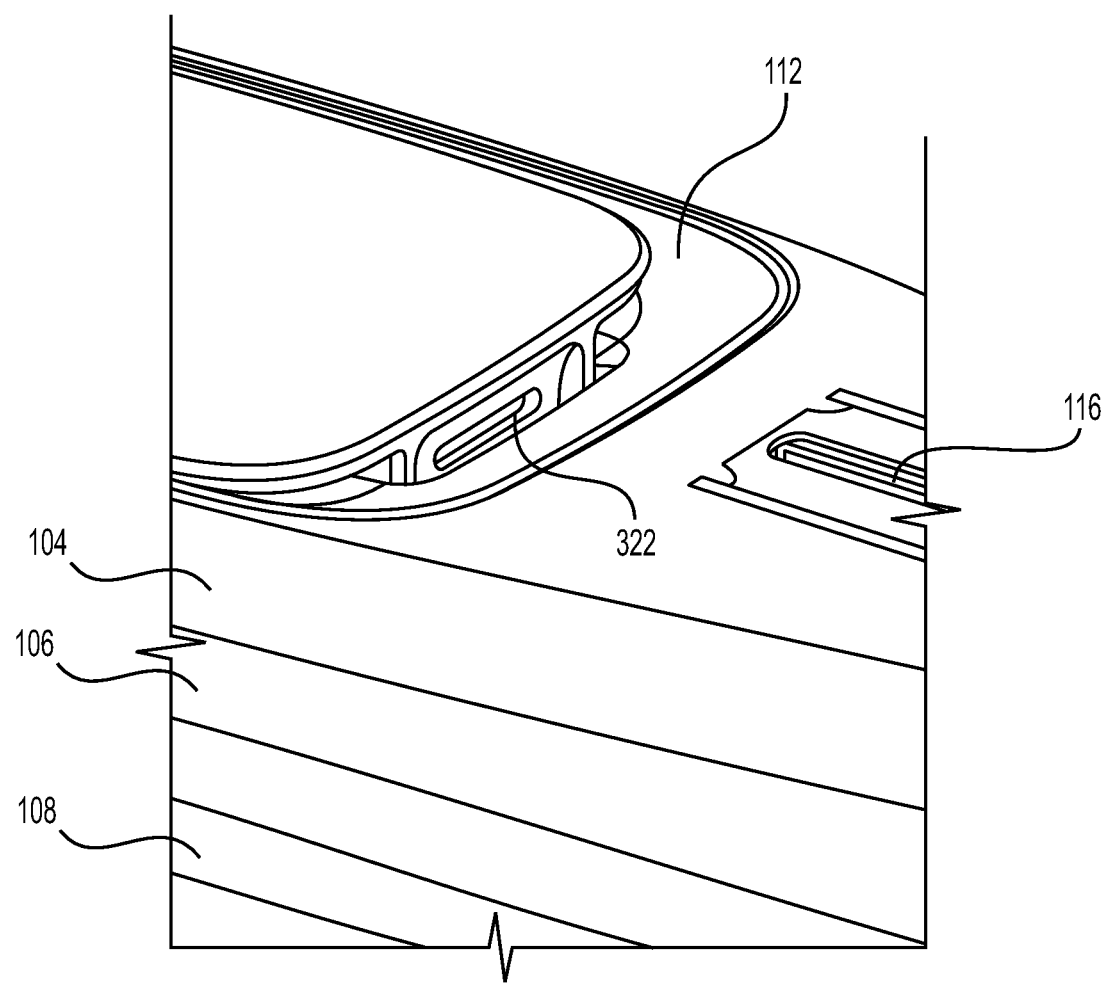
FIG. 7 is an enlarged view of the pod inlet in FIG. 6.

FIG. 6 is a perspective view of the non-nicotine e-vaping device of FIG. 1. FIG. 7 is an enlarged view of the pod inlet in FIG. 6. Referring to FIGS. 6-7, and as briefly noted above, the non-nicotine e-vaping device 500 includes a pod assembly 300 configured to hold a non-nicotine pre-vapor formulation. The pod assembly 300 has an upstream end (which faces the light guide arrangement) and a downstream end (which faces the mouthpiece 102). In a non-limiting embodiment, the upstream end is an opposing surface of the pod assembly 300 from the downstream end. The upstream end of the pod assembly 300 defines a pod inlet 322. The device body 100 defines a through hole (e.g., through hole 150 in FIG. 9) configured to receive the pod assembly 300. In an example embodiment, the bezel structure 112 of the device body 100 defines the through hole and includes an upstream rim. As shown, particularly in FIG. 7, the upstream rim of the bezel structure 112 is angled (e.g., dips inward) so as to expose the pod inlet 322 when the pod assembly 300 is seated within the through hole of the device body 100.

For instance, rather than following the contour of the front cover 104 (so as to be relatively flush with the front face of the pod assembly 300 and, thus, obscure the pod inlet 322), the upstream rim of the bezel structure 112 is in a form of a scoop configured to direct ambient air into the pod inlet 322. This angled/scoop configuration may help reduce or prevent the blockage of the air inlet (e.g., pod inlet 322) of the non-nicotine e-vaping device 500. The depth of the scoop may be such that less than half (e.g., less than a quarter) of the upstream end face of the pod assembly 300 is exposed. Additionally, in a non-limiting embodiment, the pod inlet 322 is in a form of a slot. Furthermore, if the device body 100 is regarded as extending in a first direction, then the slot may be regarded as extending in a second direction, wherein the second direction is transverse to the first direction.

Figure 8:
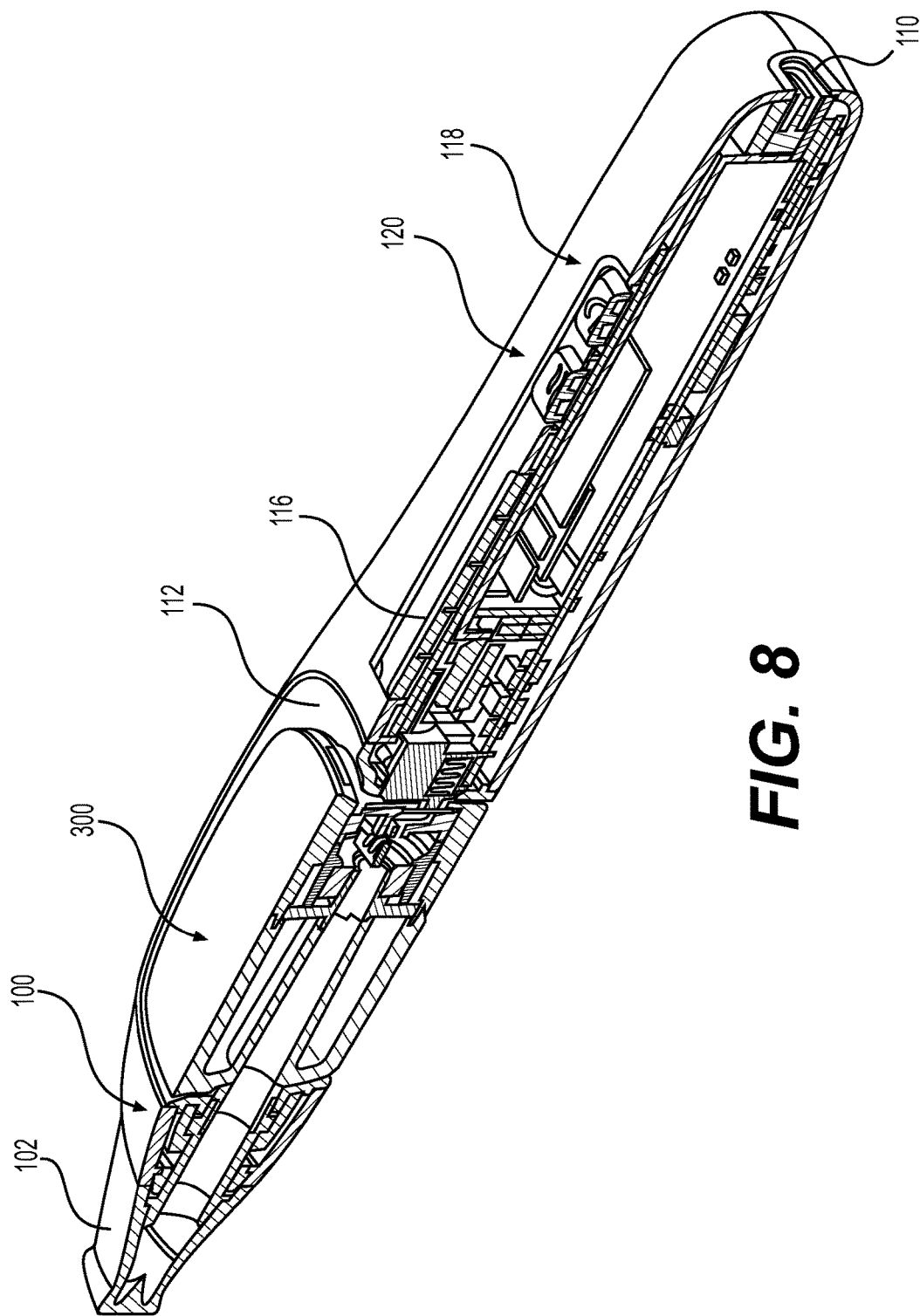
FIG. 8 is a cross-sectional view of the non-nicotine e-vaping device of FIG. 6.

FIG. 8 is a cross-sectional view of the non-nicotine e-vaping device of FIG. 6. In FIG. 8, the cross-section is taken along the longitudinal axis of the non-nicotine e-vaping device 500. As shown, the device body 100 and the pod assembly 300 include mechanical components, electronic components, and/or circuitry associated with the operation of the non-nicotine e-vaping device 500, which are discussed in more detail herein and/or are incorporated by reference herein. For instance, the pod assembly 300 may include mechanical components configured to actuate to release the non-nicotine pre-vapor formulation from a sealed reservoir within. The pod assembly 300 may also have mechanical aspects configured to engage with the device body 100 to facilitate the insertion and seating of the pod assembly 300.

Additionally, the pod assembly 300 may be a "smart pod" that includes electronic components and/or circuitry configured to store, receive, and/or transmit information to/from the device body 100. Such information may be used to authenticate the pod assembly 300 for use with the device body 100 (e.g., to prevent usage of an unapproved/counterfeit pod assembly). Furthermore, the information may be used to identify a type of the pod assembly 300 which is then correlated with a vaping profile based on the identified type. The vaping profile may be designed to set forth the general parameters for the heating of the non-nicotine pre-vapor formulation and may be subject to tuning, refining, or other adjustment by an adult vaper before and/or during vaping.

The pod assembly 300 may also communicate with the device body 100 other information that may be relevant to the operation of the non-nicotine e-vaping device 500. Examples of relevant information may include a level of the non-nicotine pre-vapor formulation within the pod assembly 300 and/or a length of time that has passed since the pod assembly 300 was inserted into the device body 100 and activated.

The device body 100 may include mechanical components (e.g. complementary structures) configured to engage, hold, and/or activate the pod assembly 300. In addition, the device body 100 may include electronic components and/or circuitry configured to receive an electric current to charge an internal power source (e.g., battery) which, in turn, is configured to supply power to the pod assembly 300 during vaping. Furthermore, the device body 100 may include electronic components and/or circuitry configured to communicate with the pod assembly 300, a different non-nicotine e-vaping device, other electronic devices (e.g., phone, tablet, computer), and/or the adult vaper.

Figure 9:
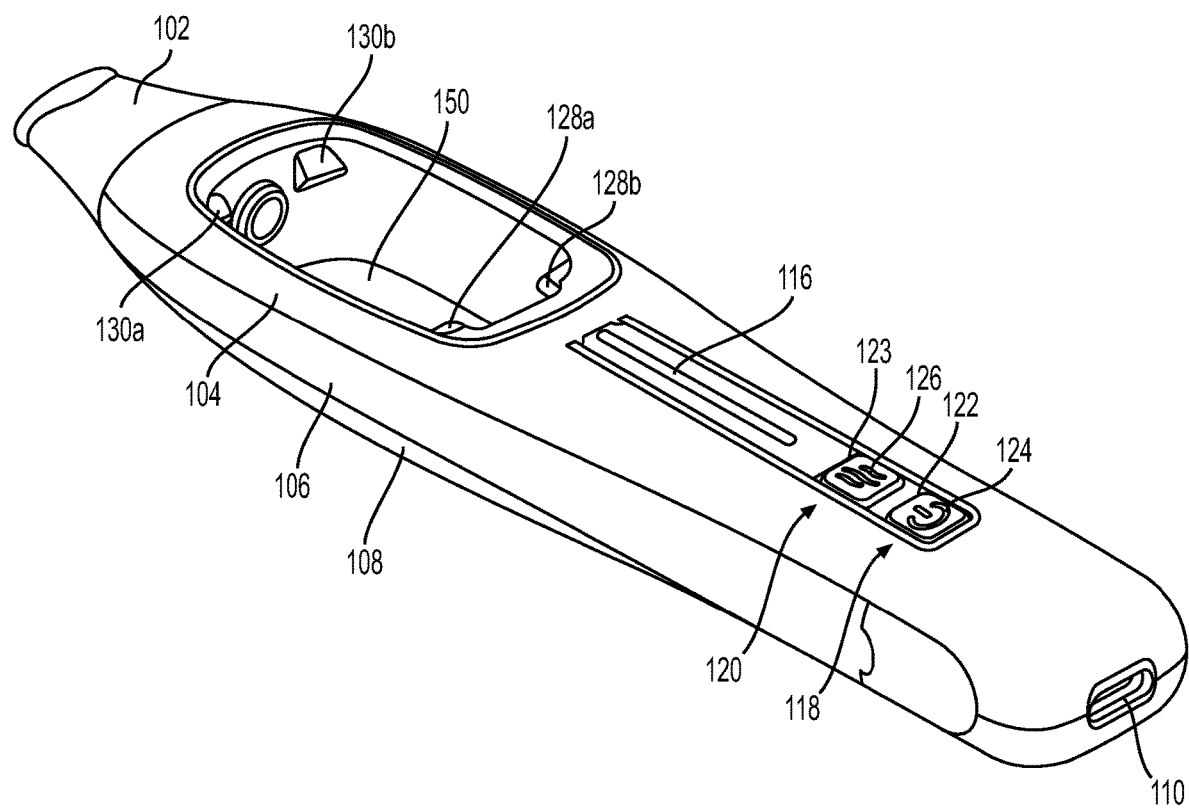
FIG. 9 is a perspective view of the device body of the non-nicotine e-vaping device of FIG. 6.

FIG. 9 is a perspective view of the device body of the non-nicotine e-vaping device of FIG. 6. Referring to FIG. 9, the bezel structure 112 of the device body 100 defines a through hole 150. The through hole 150 is configured to receive a pod assembly 300. To facilitate the insertion and seating of the pod assembly 300 within the through hole 150, the upstream rim of the bezel structure 112 includes a first upstream protrusion 128a and a second upstream protrusion 128b.

The downstream sidewall of the bezel structure 112 may define a first downstream opening, a second downstream opening, and a third downstream opening. A retention structure including a first downstream protrusion 130a and a second downstream protrusion 130b is engaged with the bezel structure 112 such that the first downstream protrusion 130a and the second downstream protrusion 130b protrude through the first downstream opening and the second downstream opening, respectively, of the bezel structure 112 and into the through hole 150.

Figure 10:
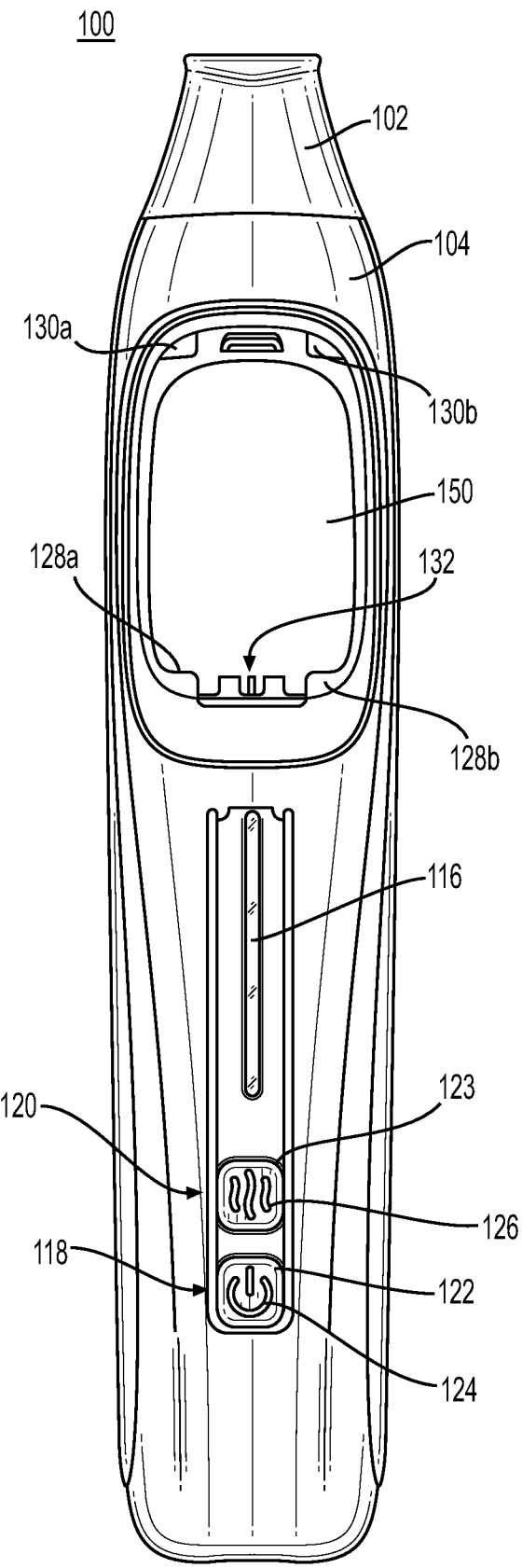
FIG. 10 is a front view of the device body of FIG. 9.

FIG. 10 is a front view of the device body of FIG. 9. Referring to FIG. 10, the device body 100 includes a device electrical connector 132 disposed at an upstream side of the through hole 150. The device electrical connector 132 of the device body 100 is configured to electrically engage with a pod assembly 300 that is seated within the through hole 150. As a result, power can be supplied from the device body 100 to the pod assembly 300 via the device electrical connector 132 during vaping. In addition, data can be sent to and/or received from the device body 100 and the pod assembly 300 via the device electrical connector 132.

Figure 11:
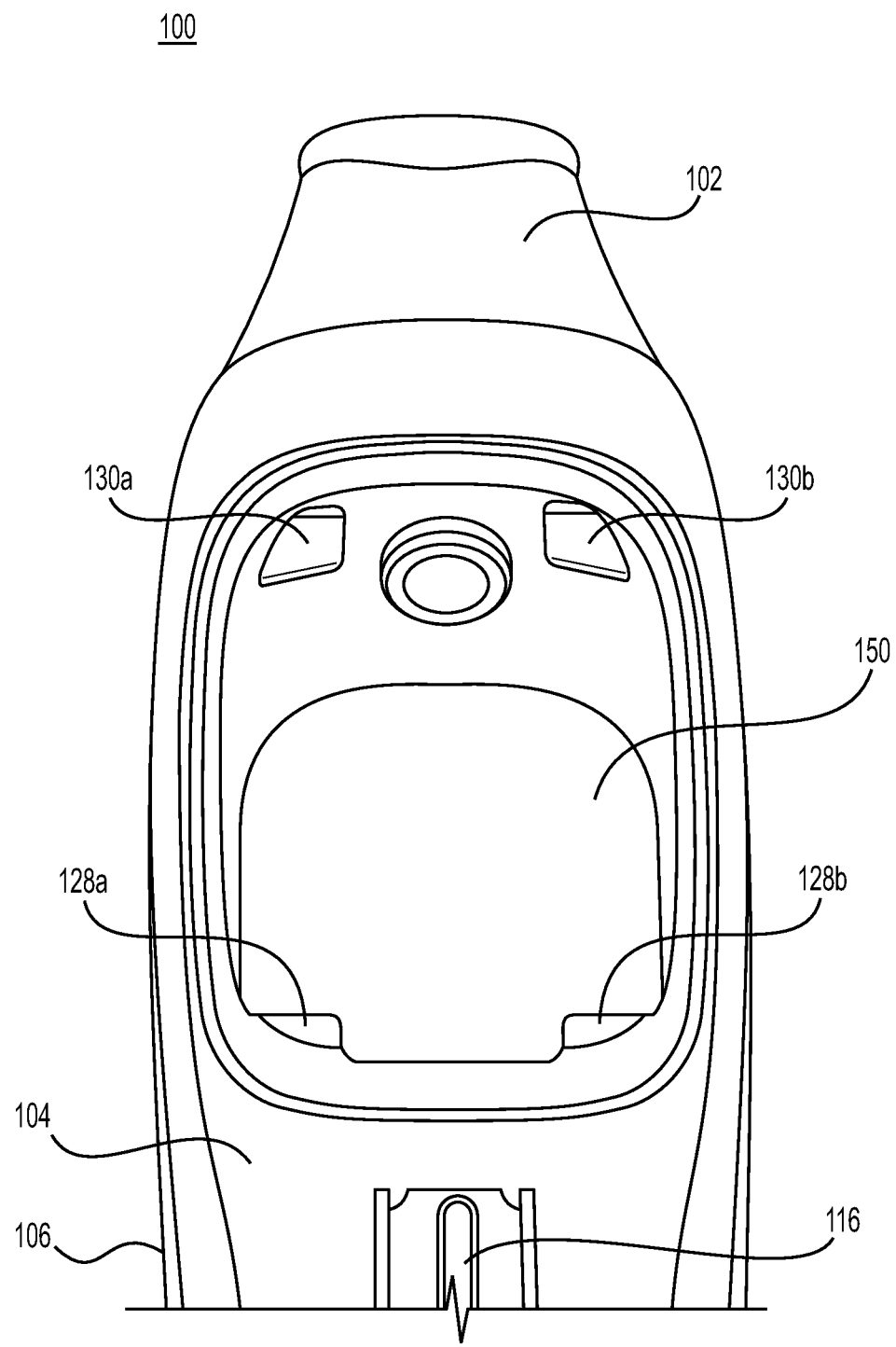
FIG. 11 is an enlarged perspective view of the through hole in FIG. 10.

FIG. 11 is an enlarged perspective view of the through hole in FIG. 10. Referring to FIG. 11, the first upstream protrusion 128a, the second upstream protrusion 128b, the first downstream protrusion 130a, the second downstream protrusion 130b, and the distal end of the mouthpiece 102 protrude into the through hole 150. In an example embodiment, the first upstream protrusion 128a and the second upstream protrusion 128b are stationary structures (e.g., stationary pivots), while the first downstream protrusion 130a and the second downstream protrusion 130b are tractable structures (e.g., retractable members). For instance, the first downstream protrusion 130a and the second downstream protrusion 130b may be configured (e.g., spring-loaded) to default to a protracted state while also configured to transition temporarily to a retracted state (and reversibly back to the protracted state) to facilitate an insertion of a pod assembly 300.

Figure 12:
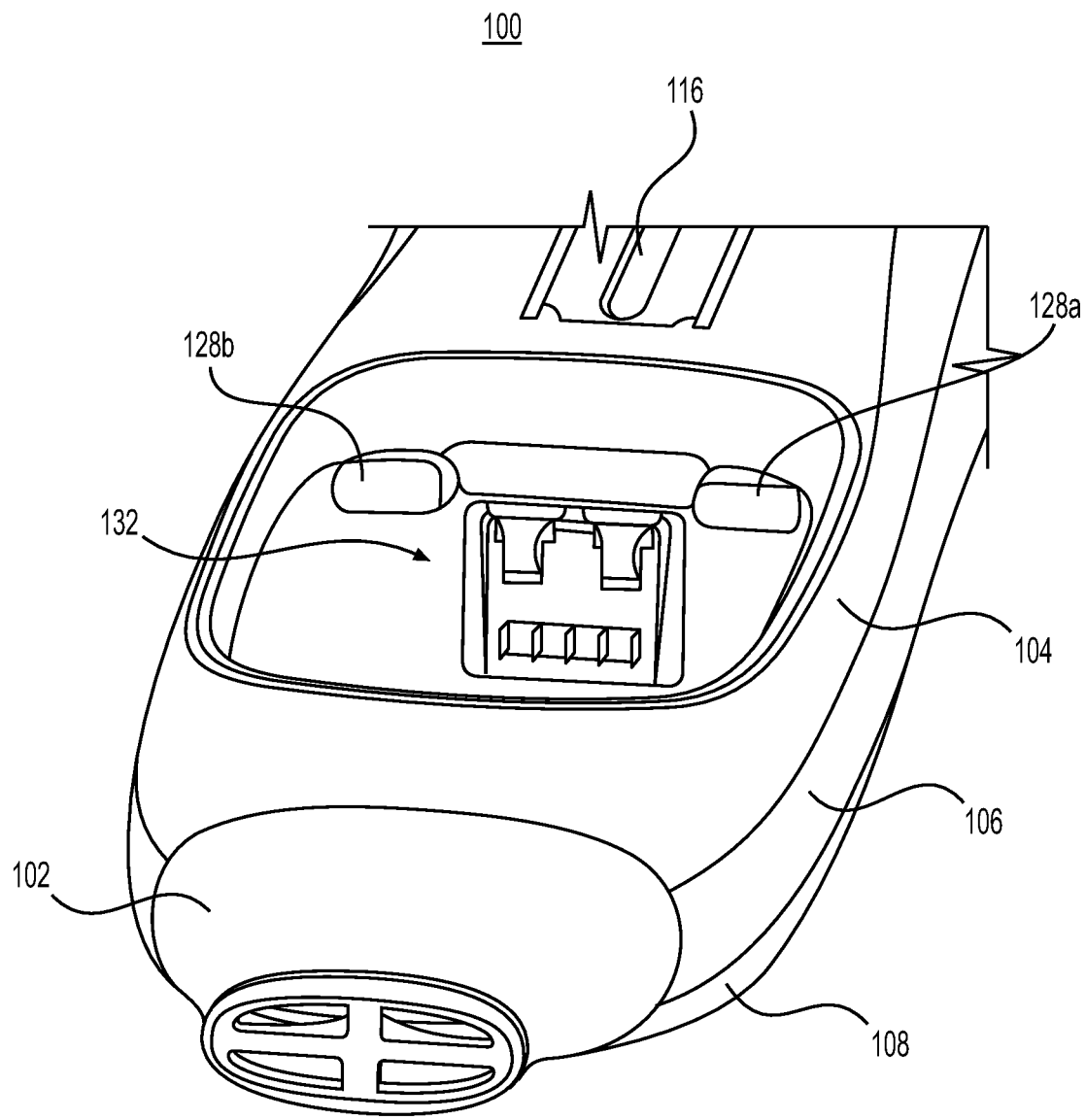
FIG. 12 is an enlarged perspective view of the device electrical connector in FIG. 10.

FIG. 12 is an enlarged perspective view of the device electrical contacts in FIG. 10. The device electrical contacts of the device body 100 are configured to engage with the pod electrical contacts of the pod assembly 300 when the pod assembly 300 is seated within the through hole 150 of the device body 100. Referring to FIG. 12, the device electrical contacts of the device body 100 include the device electrical connector 132. The device electrical connector 132 includes power contacts and data contacts. The power contacts of the device electrical connector 132 are configured to supply power from the device body 100 to the pod assembly 300. As illustrated, the power contacts of the device electrical connector 132 include a first pair of power contacts and a second pair of power contacts (which are positioned so as to be closer to the front cover 104 than the rear cover 108). The first pair of power contacts (e.g., the pair adjacent to the first upstream protrusion 128a) may be a single integral structure that is distinct from the second pair of power contacts and that, when assembled, includes two projections that extend into the through hole 150. Similarly, the second pair of power contacts (e.g., the pair adjacent to the second upstream protrusion 128b) may be a single integral structure that is distinct from the first pair of power contacts and that, when assembled, includes two projections that extend into the through hole 150. The first pair of power contacts and the second pair of power contacts of the device electrical connector 132 may be tractably-mounted and biased so as to protract into the through hole 150 as a default and to retract (e.g., independently) from the through hole 150 when subjected to a force that overcomes the bias.

Figure 13:
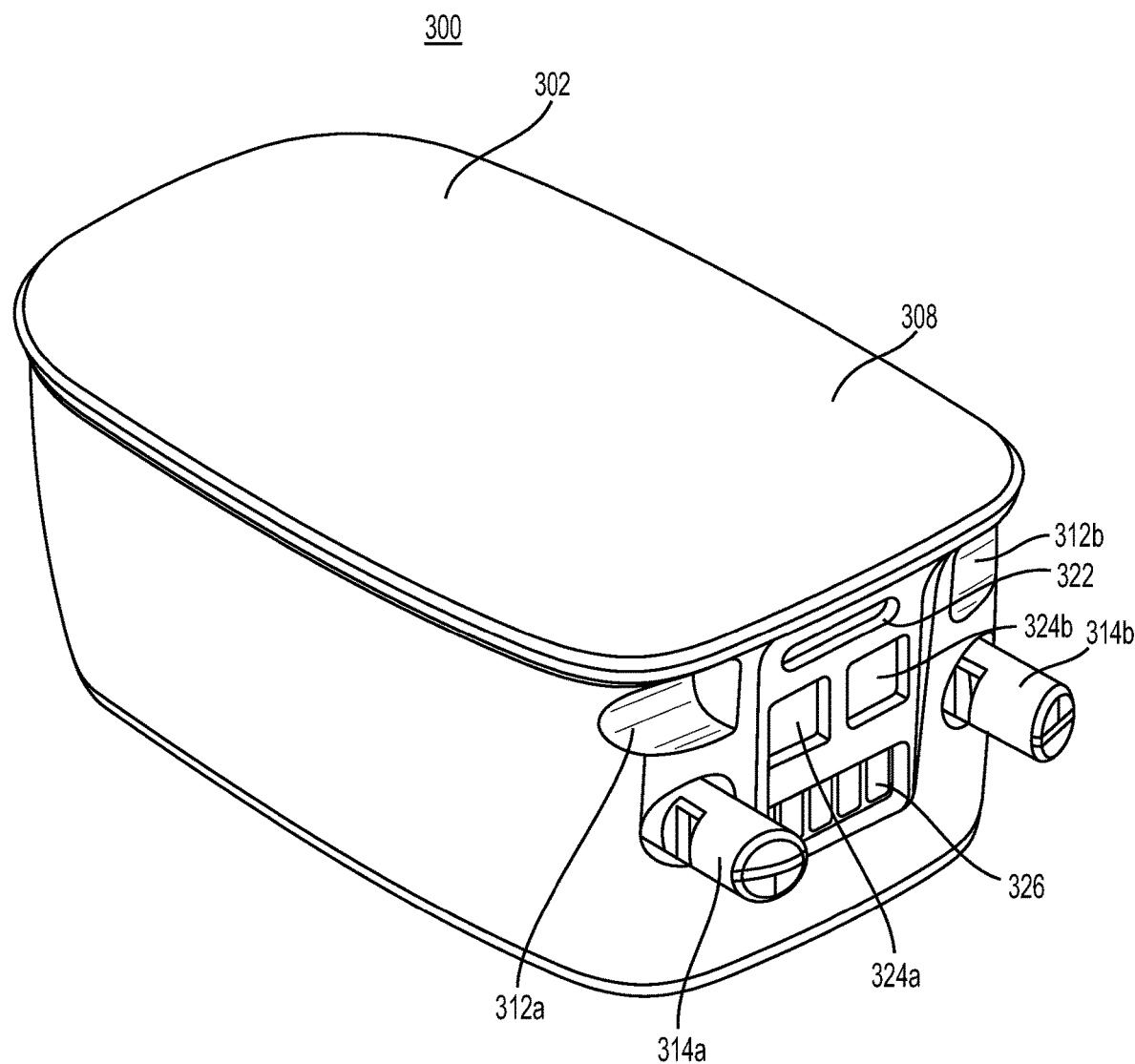
FIG. 13 is a perspective view of the pod assembly of the non-nicotine e-vaping device in FIG. 6.
Figure 14:
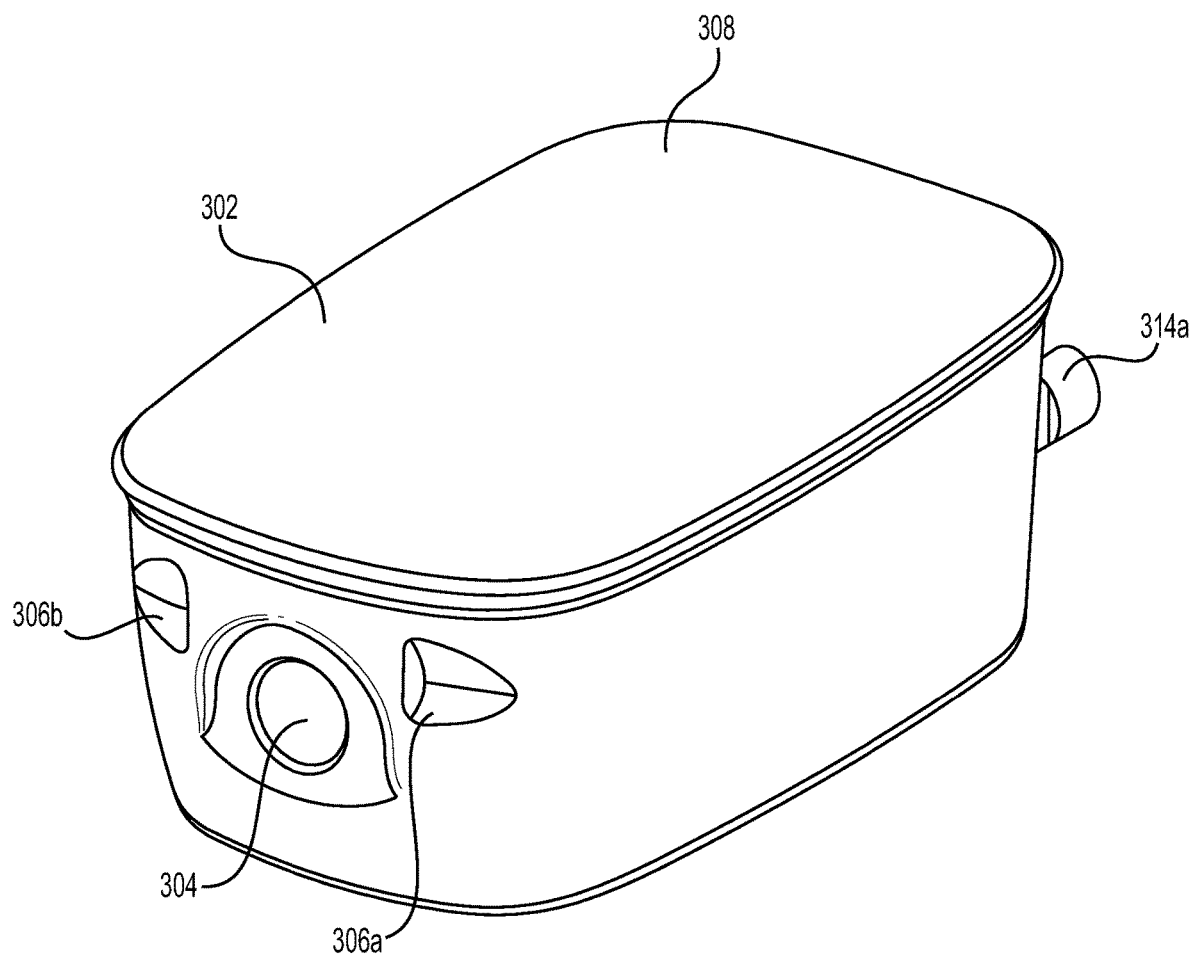
FIG. 14 is another perspective view of the pod assembly of FIG. 13.

FIG. 13 is a perspective view of the pod assembly of the non-nicotine e-vaping device in FIG. 6. FIG. 14 is another perspective view of the pod assembly of FIG. 13.

FIG. 13 is a perspective view of the pod assembly of the non-nicotine e-vaping device in FIG. 6. FIG. 14 is another perspective view of the pod assembly of FIG. 13. Referring to FIGS. 13 and 14, the pod assembly 300 for the non-nicotine e-vaping device 500 includes a pod body configured to hold a non-nicotine pre-vapor formulation. Thus, the pod assembly 300 is an example of a non-nicotine pre-vapor formulation storage portion of the non-nicotine e-vaping device 500. The pod body has an upstream end and a downstream end. The upstream end of the pod body defines a pod inlet 322. The downstream end of the pod body defines a pod outlet 304 that is in fluidic communication with the pod inlet 322 at the upstream end. During vaping, air enters the pod assembly 300 via the pod inlet 322, and non-nicotine vapor exits the pod assembly 300 via the pod outlet 304. The pod inlet 322 is shown in the drawings as being in a form of a slot. However, it should be understood that example embodiments are not limited thereto and that other forms are possible.

The pod assembly 300 includes a connector module 320 (e.g., FIG. 16) that is disposed within the pod body and exposed by openings in the upstream end. The external face of the connector module 320 includes at least one electrical contact. The at least one electrical contact may include a plurality of power contacts. For instance, the plurality of power contacts may include a first power contact 324a and a second power contact 324b. The first power contact 324a of the pod assembly 300 is configured to electrically connect with the first power contact (e.g., the power contact adjacent to the first upstream protrusion 128a in FIG. 12) of the device electrical connector 132 of the device body 100. Similarly, the second power contact 324b of the pod assembly 300 is configured to electrically connect with the second power contact (e.g., the power contact adjacent to the second upstream protrusion 128b in FIG. 12) of the device electrical connector 132 of the device body 100. In addition, the at least one electrical contact of the pod assembly 300 includes a plurality of data contacts 326. The plurality of data contacts 326 of the pod assembly 300 are configured to electrically connect with the data contacts of the device electrical connector 132 (e.g., row of five projections in FIG. 12). While two power contacts and five data contacts are shown in connection with the pod assembly 300, it should be understood that other variations are possible depending on the design of the device body 100.

In an example embodiment, the pod assembly 300 includes a front face, a rear face opposite the front face, a first side face between the front face and the rear face, a second side face opposite the first side face, an upstream end face, and a downstream end face opposite the upstream end face. The corners of the side and end faces (e.g., corner of the first side face and the upstream end face, corner of upstream end face and the second side face, corner of the second side face and the downstream end face, corner of the downstream end face and the first side face) may be rounded. However, in some instances, the corners may be angular. In addition, the peripheral edge of the front face may be in a form of a ledge. The external face of the connector module 320 (that is exposed by the pod body) may be regarded as being part of the upstream end face of the pod assembly 300. The front face of the pod assembly 300 may be wider and longer than the rear face. In such an instance, the first side face and the second side face may be angled inwards towards each other. The upstream end face and the downstream end face may also be angled inwards towards each other. Because of the angled faces, the insertion of the pod assembly 300 will be unidirectional (e.g., from the front side (side associated with the front cover 104) of the device body 100). As a result, the possibility that the pod assembly 300 will be improperly inserted into the device body 100 can be reduced or prevented.

As illustrated, the pod body of the pod assembly 300 includes a first housing section 302 and a second housing section 308. The first housing section 302 has a downstream end defining the pod outlet 304. The rim of the pod outlet 304 may optionally be a sunken or indented region. In such an instance, this region may resemble a cove, wherein the side of the rim adjacent to the rear face of the pod assembly 300 may be open, while the side of the rim adjacent to the front face may be surrounded by a raised portion of the downstream end of the first housing section 302. The raised portion may function as a stopper for the distal end of the mouthpiece 102. As a result, this configuration for the pod outlet 304 may facilitate the receiving and aligning of the distal end of the mouthpiece 102 (e.g., FIG. 11) via the open side of the rim and its subsequent seating against the raised portion of the downstream end of the first housing section 302. In a non-limiting embodiment, the distal end of the mouthpiece 102 may also include (or be formed of) a resilient material to help create a seal around the pod outlet 304 when the pod assembly 300 is properly inserted within the through hole 150 of the device body 100.

The downstream end of the first housing section 302 additionally defines at least one downstream recess. In an example embodiment, the at least one downstream recess is in a form of a first downstream recess 306a and a second downstream recess 306b. The pod outlet 304 may be between the first downstream recess 306a and the second downstream recess 306b. The first downstream recess 306a and the second downstream recess 306b are configured to engage with the first downstream protrusion 130a and the second downstream protrusion 130b, respectively, of the device body 100. As shown in FIG. 11, the first downstream protrusion 130a and the second downstream protrusion 130b of the device body 100 may be disposed on adjacent corners of the downstream sidewall of the through hole 150. The first downstream recess 306a and the second downstream recess 306b may each be in a form of a V-shaped notch. In such an instance, each of the first downstream protrusion 130a and the second downstream protrusion 130b of the device body 100 may be in a form of a wedge-shaped structure configured to engage with a corresponding V-shaped notch of the first downstream recess 306a and the second downstream recess 306b. The first downstream recess 306a may abut the corner of the downstream end face and the first side face, while the second downstream recess 306b may abut the corner of the downstream end face and the second side face. As a result, the edges of the first downstream recess 306a and the second downstream recess 306b adjacent to the first side face and the second side face, respectively, may be open. In such an instance, as shown in FIG. 14, each of the first downstream recess 306a and the second downstream recess 306b may be a 3-sided recess.

The second housing section 308 has an upstream end further defining (in addition to the pod inlet 322) a plurality of openings (e.g., first power contact opening 325a, second power contact opening 325b, data contact opening 327) configured to expose the connector module 320 (FIGS. 15-16) within the pod assembly 300. The upstream end of the second housing section 308 also defines at least one upstream recess. In an example embodiment, the at least one upstream recess is in a form of a first upstream recess 312a and a second upstream recess 312b. The pod inlet 322 may be between the first upstream recess 312a and the second upstream recess 312b. The first upstream recess 312a and the second upstream recess 312b are configured to engage with the first upstream protrusion 128a and the second upstream protrusion 128b, respectively, of the device body 100. As shown in FIG. 12, the first upstream protrusion 128a and the second upstream protrusion 128b of the device body 100 may be disposed on adjacent corners of the upstream sidewall of the through hole 150. A depth of each of the first upstream recess 312a and the second upstream recess 312b may be greater than a depth of each of the first downstream recess 306a and the second downstream recess 306b. A terminus of each of the first upstream recess 312a and the second upstream recess 312b may also be more rounded than a terminus of each of the first downstream recess 306a and the second downstream recess 306b. For instance, the first upstream recess 312a and the second upstream recess 312b may each be in a form of a U-shaped indentation. In such an instance, each of the first upstream protrusion 128a and the second upstream protrusion 128b of the device body 100 may be in a form of a rounded knob configured to engage with a corresponding U-shaped indentation of the first upstream recess 312a and the second upstream recess 312b. The first upstream recess 312a may abut the corner of the upstream end face and the first side face, while the second upstream recess 312b may abut the corner of the upstream end face and the second side face. As a result, the edges of the first upstream recess 312a and the second upstream recess 312b adjacent to the first side face and the second side face, respectively, may be open.

The first housing section 302 may define a reservoir within configured to hold the non-nicotine pre-vapor formulation. The reservoir may be configured to hermetically seal the non-nicotine pre-vapor formulation until an activation of the pod assembly 300 to release the non-nicotine pre-vapor formulation from the reservoir. As a result of the hermetic seal, the non-nicotine pre-vapor formulation may be isolated from the environment as well as the internal elements of the pod assembly 300 that may potentially react with the non-nicotine pre-vapor formulation, thereby reducing or preventing the possibility of adverse effects to the shelf-life and/or sensorial characteristics (e.g., flavor) of the non-nicotine pre-vapor formulation. The second housing section 308 may contain structures configured to activate the pod assembly 300 and to receive and heat the non-nicotine pre-vapor formulation released from the reservoir after the activation.

The pod assembly 300 may be activated manually by an adult vaper prior to the insertion of the pod assembly 300 into the device body 100. Alternatively, the pod assembly 300 may be activated as part of the insertion of the pod assembly 300 into the device body 100. In an example embodiment, the second housing section 308 of the pod body includes a perforator configured to release the non-nicotine pre-vapor formulation from the reservoir in the first housing section 302 during the activation of the pod assembly 300. The perforator may be in a form of a first activation pin 314a and a second activation pin 314b, which will be discussed in more detail herein.

To activate the pod assembly 300 manually, an adult vaper may press the first activation pin 314a and the second activation pin 314b inward (e.g., simultaneously or sequentially) prior to inserting the pod assembly 300 into the through hole 150 of the device body 100. For instance, the first activation pin 314a and the second activation pin 314b may be manually pressed until the ends thereof are substantially even with the upstream end face of the pod assembly 300. In an example embodiment, the inward movement of the first activation pin 314a and the second activation pin 314b causes a seal of the reservoir to be punctured or otherwise compromised so as to release the non-nicotine pre-vapor formulation therefrom.

Alternatively, to activate the pod assembly 300 as part of the insertion of the pod assembly 300 into the device body 100, the pod assembly 300 is initially positioned such that the first upstream recess 312a and the second upstream recess 312b are engaged with the first upstream protrusion 128a and the second upstream protrusion 128b, respectively (e.g., upstream engagement). Because each of the first upstream protrusion 128a and the second upstream protrusion 128b of the device body 100 may be in a form of a rounded knob configured to engage with a corresponding U-shaped indentation of the first upstream recess 312a and the second upstream recess 312b, the pod assembly 300 may be subsequently pivoted with relative ease about the first upstream protrusion 128a and the second upstream protrusion 128b and into the through hole 150 of the device body 100.

With regard to the pivoting of the pod assembly 300, the axis of rotation may be regarded as extending through the first upstream protrusion 128a and the second upstream protrusion 128b and oriented orthogonally to a longitudinal axis of the device body 100. During the initial positioning and subsequent pivoting of the pod assembly 300, the first activation pin 314a and the second activation pin 314b will come into contact with the upstream sidewall of the through hole 150 and transition from a protracted state to a retracted state as the first activation pin 314a and the second activation pin 314b are pushed (e.g., simultaneously) into the second housing section 308 as the pod assembly 300 progresses into the through hole 150. When the downstream end of the pod assembly 300 reaches the vicinity of the downstream sidewall of the through hole 150 and comes into contact with the first downstream protrusion 130a and the second downstream protrusion 130b, the first downstream protrusion 130a and the second downstream protrusion 130b will retract and then resiliently protract (e.g., spring back) when the positioning of the pod assembly 300 allows the first downstream protrusion 130a and the second downstream protrusion 130b of the device body 100 to engage with the first downstream recess 306a and the second downstream recess 306b, respectively, of the pod assembly 300 (e.g., downstream engagement).

As noted supra, according to an example embodiment, the mouthpiece 102 is secured to the retention structure 140 (of which the first downstream protrusion 130a and the second downstream protrusion 130b are a part). In such an instance, the retraction of the first downstream protrusion 130a and the second downstream protrusion 130b from the through hole 150 will cause a simultaneous shift of the mouthpiece 102 by a corresponding distance in the same direction (e.g., downstream direction). Conversely, the mouthpiece 102 will spring back simultaneously with the first downstream protrusion 130a and the second downstream protrusion 130b when the pod assembly 300 has been sufficiently inserted to facilitate downstream engagement. In addition to the resilient engagement by the first downstream protrusion 130a and the second downstream protrusion 130b, the distal end of the mouthpiece 102 is configured to also be biased against the pod assembly 300 (and aligned with the pod outlet 304 so as to form a relatively vapor-tight seal) when the pod assembly 300 is properly seated within the through hole 150 of the device body 100.

Furthermore, the downstream engagement may produce an audible click and/or a haptic feedback to indicate that the pod assembly 300 is properly seated within the through hole 150 of the device body 100. When properly seated, the pod assembly 300 will be connected to the device body 100 mechanically, electrically, and fluidically. Although the non-limiting embodiments herein describe the upstream engagement of the pod assembly 300 as occurring before the downstream engagement, it should be understood that the pertinent mating, activation, and/or electrical arrangements may be reversed such that the downstream engagement occurs before the upstream engagement.

Figure 15:
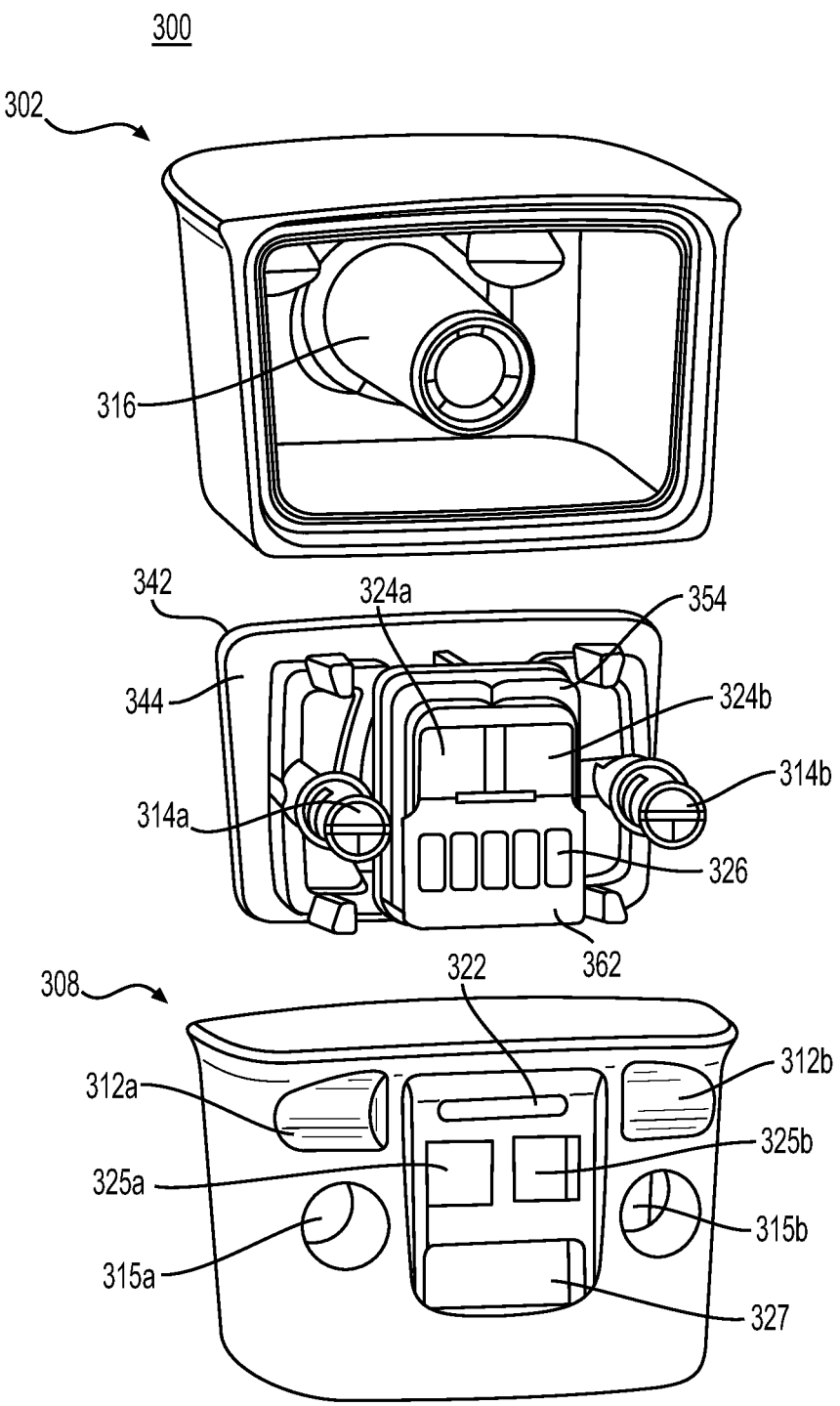
FIG. 15 is a partially exploded view of the pod assembly of FIG. 13.

FIG. 15 is a partially exploded view of the pod assembly of FIG. 13. Referring to FIG. 15, the first housing section 302 includes a vapor channel 316. The vapor channel 316 is configured to receive the non-nicotine vapor generated during vaping and is in fluidic communication with the pod outlet 304. In an example embodiment, the vapor channel 316 may gradually increase in size (e.g., diameter) as it extends towards the pod outlet 304. In addition, the vapor channel 316 may be integrally formed with the first housing section 302. An insert 342 and a seal 344 are disposed at an upstream end of the first housing section 302 to define the reservoir of the pod assembly 300. For instance, the insert 342 may be seated within the first housing section 302 such that the peripheral surface of the insert 342 engages with the inner surface of the first housing section 302 along the rim (e.g., via interference fit) such that the interface of the peripheral surface of the insert 342 and the inner surface of the first housing section 302 is fluid-tight (e.g., liquid-tight and/or air-tight). Furthermore, the seal 344 is attached to the upstream side of the insert 342 to close off the reservoir outlets in the insert 342 so as to provide a fluid-tight (e.g., liquid-tight and/or air-tight) containment of the non-nicotine pre-vapor formulation in the reservoir.

The upstream end of the second housing section 308 defines a pod inlet 322, a first power contact opening 325a, a second power contact opening 325b, a data contact opening 327, a first upstream recess 312a, a second upstream recess 312b, a first pin opening 315a, and a second pin opening 315b. As noted supra, the pod inlet 322 allows air to enter the pod assembly 300 during vaping, while the first power contact opening 325a, the second power contact opening 325b, and the data contact opening 327 are configured to expose the first power contact 324a, the second power contact 324b, and the data contacts 326, respectively, of the connector module 320. In an example embodiment, the first power contact 324a and the second power contact 324b are mounted on a module housing 354 of the connector module 320. In addition, the data contacts 326 may be disposed on a printed circuit board (PCB) 362. Furthermore, the pod inlet 322 may be situated between the first upstream recess 312a and the second upstream recess 312b, while the contact openings (e.g., first power contact opening 325a, second power contact opening 325b, data contact opening 327) may be situated between the first pin opening 315a and the second pin opening 315b. The first pin opening 315a and the second pin opening 315b are configured to accommodate the first activation pin 314a and the second activation pin 314b, respectively, which extend therethrough.

Figure 16:
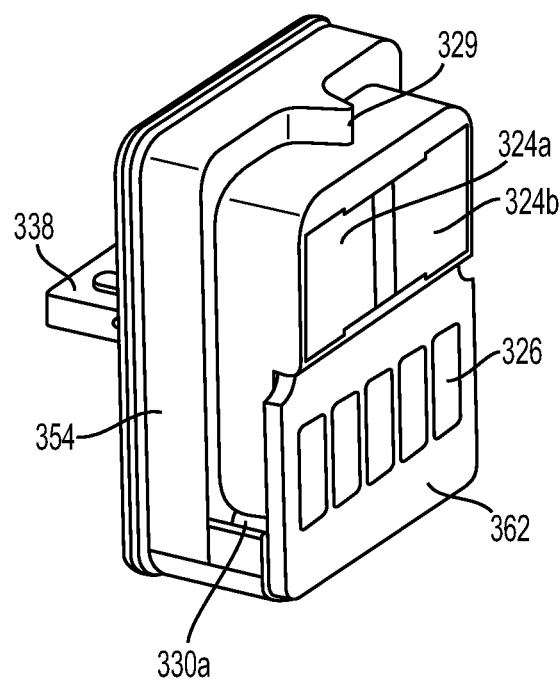
FIG. 16 is a perspective view of the connector module in FIG. 15.
Figure 17:
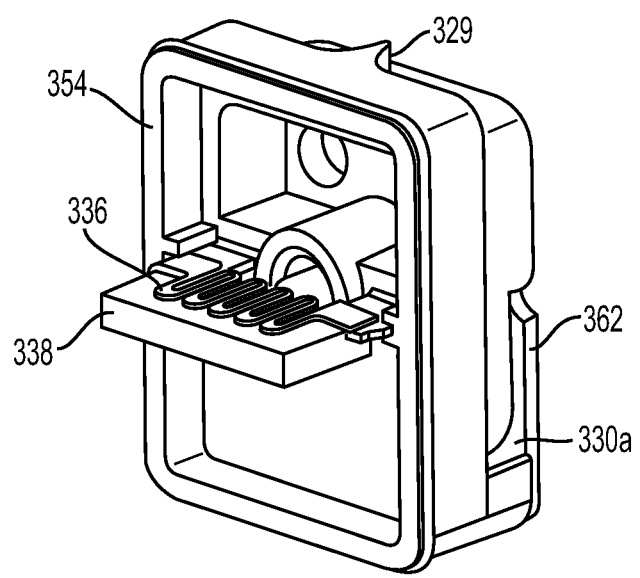
FIG. 17 is another perspective view of the connector module of FIG. 15.

FIG. 16 is a perspective view of the connector module in FIG. 15. FIG. 17 is another perspective view of the connector module of FIG. 16. Referring to FIGS. 16-17, the general framework of the connector module 320 includes a module housing 354. In addition, the connector module 320 has a plurality of faces, including an external face and side faces adjacent to the external face. In an example embodiment, the external face of the connector module 320 is composed of upstream surfaces of the module housing 354, the first power contact 324a, the second power contact 324b, the data contacts 326, and the printed circuit board (PCB) 362. The side faces of the connector module 320 may be integral parts of the module housing 354 and generally orthogonal to the external face.

The pod assembly 300 defines a flow path within from the pod inlet 322 to the pod outlet 304. The flow path through the pod assembly 300 includes, inter alia, a first diverged portion, a second diverged portion, and a converged portion. The pod inlet 322 is upstream from the first diverged portion and the second diverged portion of the flow path. In particular, as shown in FIG. 16, the side face (e.g., inlet side face) of the module housing 354 (and the connector module 320) above the first power contact 324a and the second power contact 324b is recessed so as to define a divider 329 along with initial segments of the first diverged portion and the second diverged portion of the flow path. In an example embodiment where the divider 329 is indented from the external face of the module housing 354 (e.g., FIG. 16), the side face of the module housing 354 above the first power contact 324a and the second power contact 324b may also be regarded as defining an inlet portion of the flow path that is downstream from the pod inlet 322 and upstream from the first diverged portion and the second diverged portion of the flow path.

The pair of longer side faces (e.g., vertical side faces) of the module housing 354 is also recessed so as to define subsequent segments of the first diverged portion and the second diverged portion of the flow path. Herein, the pair of longer side faces of the module housing 354 may be referred to, in the alternative, as lateral faces. The sector of the module housing 354 covered by the printed circuit board (PCB) 362 in FIG. 16 (but shown in FIG. 20) defines further segments of the first diverged portion and the second diverged portion along with the converged portion of the flow path. The further segments of the first diverged portion and the second diverged portion include a first curved segment (e.g., first curved path 330a) and a second curved segment (e.g., second curved path 330b), respectively. As will be discussed in more detail herein, the first diverged portion and the second diverged portion convene to form the converged portion of the flow path.

When the connector module 320 is seated within a receiving cavity in the downstream side of the second housing section 308, the unrecessed side faces of the module housing 354 interface with the sidewalls of the receiving cavity of the second housing section 308, while the recessed side faces of the module housing 354 together with the sidewalls of the receiving cavity define the first diverged portion and the second diverged portion of the flow path. The seating of the connector module 320 within the receiving cavity of the second housing section 308 may be via a close-fit arrangement such that the connector module 320 remains essentially stationary within the pod assembly 300.

As shown in FIG. 17, the connector module 320 includes a wick 338 that is configured to transfer a non-nicotine pre-vapor formulation to a heater 336. The heater 336 is configured to heat the non-nicotine pre-vapor formulation during vaping to generate a non-nicotine vapor. The heater 336 is electrically connected to at least one electrical contact of the connector module 320. For instance, one end (e.g., first end) of the heater 336 may be connected to the first power contact 324a, while the other end (e.g., second end) of the heater 336 may be connected to the second power contact 324b. In an example embodiment, the heater 336 includes a folded heating element. In such an instance, the wick 338 may have a planar form configured to be held by the folded heating element. When the pod assembly 300 is assembled, the wick 338 is configured to be in fluidic communication with an absorbent material such that the non-nicotine pre-vapor formulation that will be in the absorbent material (when the pod assembly 300 is activated) will be transferred to the wick 338 via capillary action. In the present specification, a heater may also be referred to as a heating engine.

In an example embodiment, an incoming air flow entering the pod assembly 300 through the pod inlet 322 is directed by the divider 329 into the first diverged portion and the second diverged portion of the flow path. The divider 329 may be wedge-shaped and configured to split the incoming air flow into opposite directions (e.g., at least initially). The split air flow may include a first air flow (that travels through the first diverged portion of the flow path) and a second air flow (that travels through the second diverged portion of the flow path). Following the split by the divider 329, the first air flow travels along the inlet side face and continues around the corner to and along the first lateral face to the first curved path 330a. Similarly, the second air flow travels along the inlet side face and continues around the corner to and along the second lateral face to the second curved path 330b (e.g., FIG. 20). The converged portion of the flow path is downstream from the first diverged portion and the second diverged portion. The heater 336 and the wick 338 are downstream from the converged portion of the flow path. Thus, the first air flow joins with the second air flow in the converged portion (e.g., converged path 330c in FIG. 20) of the flow path to form a combined flow before passing through a module outlet 368 (e.g., labeled in FIG. 18) in the module housing 354 to the heater 336 and the wick 338.

According to at least some example embodiments, the wick 338 may be a fibrous pad or other structure with pores/interstices designed for capillary action. In addition, the wick 338 may have a rectangular shape, although example embodiments are not limited thereto. For instance, the wick 338 may have an alternative shape of an irregular hexagon, wherein two of the sides are angled inward and toward the heater 336. The wick 338 may be fabricated into the desired shape or cut from a larger sheet of material into such a shape. Where the lower section of the wick 338 is tapered towards the winding section of the heater 336 (e.g., hexagon shape), the likelihood of the non-nicotine pre-vapor formulation being in a part of the wick 338 that continuously evades vaporization (due to its distance from the heater 336) can be reduced or avoided. Furthermore, as noted supra, the heater 336 may include a folded heating element configured to grip the wick 338. The folded heating element may also include at least one prong configured to protrude into the wick 338.

In an example embodiment, the heater 336 is configured to undergo Joule heating (which is also known as ohmic/resistive heating) upon the application of an electric current thereto. Stated in more detail, the heater 336 may be formed of one or more conductors and configured to produce heat when an electric current passes therethrough. The electric current may be supplied from a power source (e.g., battery) within the device body 100 and conveyed to the heater 336 via the first power contact 324a or the second power contact 324b.

Suitable conductors for the heater 336 include an iron-based alloy (e.g., stainless steel) and/or a nickel-based alloy (e.g., nichrome). The heater 336 may be fabricated from a conductive sheet (e.g., metal, alloy) that is stamped to cut a winding pattern therefrom. The winding pattern may have curved segments alternately arranged with horizontal segments so as to allow the horizontal segments to zigzag back and forth while extending in parallel. In addition, a width of each of the horizontal segments of the winding pattern may be substantially equal to a spacing between adjacent horizontal segments of the winding pattern, although example embodiments are not limited thereto. To obtain the form of the heater 336 shown in the drawings, the winding pattern may be folded so as to grip the wick 338. Additionally, when prongs are part of the heater 336, the projections corresponding to the prongs are bent (e.g., inward and/or orthogonally) before the winding pattern is folded. As a result of the prongs, the possibility that the wick 338 will slip out of the heater 336 will be reduced or prevented. The heater and associated structures are discussed in more detail in U.S. application Ser. No. 15/729,909, titled "Folded Heater For Electronic Vaping Device", filed Oct. 11, 2017, the entire contents of which is incorporated herein by reference.

Referring to FIG. 15, the first housing section 302 includes a vapor channel 316. The vapor channel 316 is configured to receive vapor generated by the heater 336 and is in fluidic communication with the pod outlet 304. In an example embodiment, the vapor channel 316 may gradually increase in size (e.g., diameter) as it extends towards the pod outlet 304. In addition, the vapor channel 316 may be integrally formed with the first housing section 302. An insert 342 and a seal 344 are disposed at an upstream end of the first housing section 302 to define the reservoir of the pod assembly 300. For instance, the insert 342 may be seated within the first housing section 302 such that the peripheral surface of the insert 342 engages with the inner surface of the first housing section 302 along the rim (e.g., via interference fit) such that the interface of the peripheral surface of the insert 342 and the inner surface of the first housing section 302 is fluid-tight (e.g., liquid-tight and/or air-tight). Furthermore, the seal 344 is attached to the upstream side of the insert 342 to close off the reservoir outlets in the insert 342 so as to provide a fluid-tight (e.g., liquid-tight and/or air-tight) containment of the non-nicotine pre-vapor formulation in the reservoir. Herein, the first housing section 302, the insert 342, and the seal 344 may be referred to collectively as the first section. As will be discussed in more detail herein, the first section is configured to hermetically seal the non-nicotine pre-vapor formulation until an activation of the pod assembly 300.

According to at least some example embodiments, the insert 342 includes a holder portion that projects from the upstream side and a connector portion that projects from the downstream side. According to at least some example embodiments, the holder portion of the insert 342 is configured to hold an absorbent material, while a connector portion of the insert 342 is configured to engage with the vapor channel 316 of the first housing section 302. The connector portion of the insert 342 may be configured to be seated within the vapor channel 316 and, thus, engage the interior of the vapor channel 316. Alternatively, the connector portion of the insert 342 may be configured to receive the vapor channel 316 and, thus, engage with the exterior of the vapor channel 316. The insert 342 also defines reservoir outlets through which the non-nicotine pre-vapor formulation flows when the seal 344 is punctured during the activation of the pod assembly 300. The holder portion and the connector portion of the insert 342 may be between the reservoir outlets (e.g., first and second reservoir outlets), although example embodiments are not limited thereto. Furthermore, the insert 342 defines a vapor conduit extending through the holder portion and the connector portion. As a result, when the insert 342 is seated within the first housing section 302, the vapor conduit of the insert 342 will be aligned with and in fluidic communication with the vapor channel 316 so as to form a continuous path through the reservoir to the pod outlet 304 for the non-nicotine vapor generated by the heater 336 during vaping.

The seal 344 is attached to the upstream side of the insert 342 so as to cover the reservoir outlets in the insert 342. In an example embodiment, the seal 344 defines an opening (e.g., central opening) configured to provide the pertinent clearance to accommodate the holder portion (that projects from the upstream side of the insert 342) when the seal 344 is attached to the insert 342. When the seal 344 is punctured by the first activation pin 314a and the second activation pin 314b of the pod assembly 300, the two punctured sections of the seal 344 will be pushed into the reservoir as flaps, thus creating two punctured openings (e.g., one on each side of the central opening) in the seal 344. The size and shape of the punctured openings in the seal 344 may correspond to the size and shape of the reservoir outlets in the insert 342. In contrast, when in an unpunctured state, the seal 344 may have a planar form and only one opening (e.g., central opening). The seal 344 is designed to be strong enough to remain intact during the normal movement and/or handling of the pod assembly 300 so as to avoid being prematurely/inadvertently breached. For instance, the seal 344 may be a coated foil (e.g., aluminum-backed Tritan).

The second housing section 308 may be structured to contain various components configured to release, receive, and heat the non-nicotine pre-vapor formulation. For instance, the first activation pin 314a and the second activation pin 314b are configured to puncture the reservoir in the first housing section 302 to release the non-nicotine pre-vapor formulation. Each of the first activation pin 314a and the second activation pin 314b has a distal end that extends through a corresponding one of the first pin opening 315a and the second pin opening 315b in the second housing section 308. In an example embodiment, the distal ends of the first activation pin 314a and the second activation pin 314b are visible after assembly (e.g., FIG. 13), while the remainder of the first activation pin 314a and the second activation pin 314b are hidden from view within the pod assembly 300. In addition, each of the first activation pin 314a and the second activation pin 314b has a proximal end that is positioned so as to be adjacent to and upstream from the seal 344 prior to activation of the pod assembly 300. When the first activation pin 314a and the second activation pin 314b are pushed into the second housing section 308 to activate the pod assembly 300, the proximal end of each of the first activation pin 314a and the second activation pin 314b will advance through the insert 342 and, as a result, puncture the seal 344, which will release the non-nicotine pre-vapor formulation from the reservoir. The movement of the first activation pin 314a may be independent of the movement of the second activation pin 314b (and vice versa).

An absorbent material may be downstream from and in fluidic communication with the wick 338. Furthermore, as noted supra, the absorbent material may be configured to engage with a holder portion of the insert 342 (which may project from the upstream side of the insert 342). The absorbent material may have an annular form, although example embodiments are not limited thereto. For example, the absorbent material may resemble a hollow cylinder. In such an instance, the outer diameter of the absorbent material may be substantially equal to (or slightly larger than) the length of the wick 338. The inner diameter of the absorbent material may be smaller than the average outer diameter of the holder portion of the insert 342 so as to result in an interference fit. To facilitate the engagement with the absorbent material, the tip of the holder portion of the insert 342 may be tapered. The absorbent material may be configured to receive and hold a quantity of the non-nicotine pre-vapor formulation released from the reservoir when the pod assembly 300 is activated. The wick 338 may be positioned within the pod assembly 300 so as to be in fluidic communication with the absorbent material such that the non-nicotine pre-vapor formulation can be drawn from the absorbent material to the heater 336 via capillary action. The wick 338 may physically contact an upstream side of the absorbent material. In addition, the wick 338 may be aligned with a diameter of the absorbent material, although example embodiments are not limited thereto.

Figure 18:
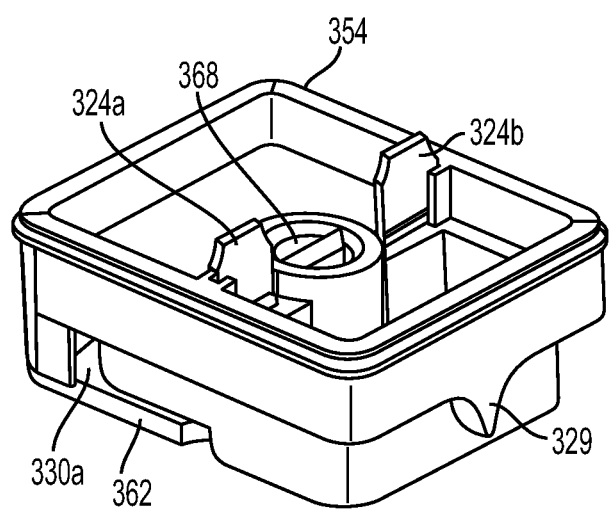
FIG. 18 is a perspective view of the connector module of FIG. 17 without the wick and heater.

As illustrated in FIG. 17, the heater 336 may have a folded configuration so as to grip and establish thermal contact with the opposing surfaces of the wick 338. The heater 336 is configured to heat the wick 338 during vaping to generate a non-nicotine vapor. To facilitate such heating, the first end of the heater 336 may be electrically connected to the first power contact 324a (FIGS. 16 and 18), while the second end of the heater 336 may be electrically connected to the second power contact 324b (FIGS. 16 and 18). As a result, an electric current may be supplied from a power source (e.g., battery) within the device body 100 and conveyed to the heater 336 via the first power contact 324a or the second power contact 324b. The relevant details of other aspects of the connector module 320 that have already been discussed supra (e.g., in connection with FIGS. 16-17) will not be repeated in this section in the interest of brevity. In an example embodiment, the second housing section 308 includes a receiving cavity for the connector module 320. Collectively, the second housing section 308 and the above-discussed components therein may be referred to as the second section. During vaping, the non-nicotine vapor generated by the heater 336 is drawn through the vapor conduit of the insert 342, through the vapor channel 316 of the first housing section 302, out the pod outlet 304 of the pod assembly 300, and through the vapor passage 136 of the mouthpiece 102 to the vapor outlet(s).

Figure 19:
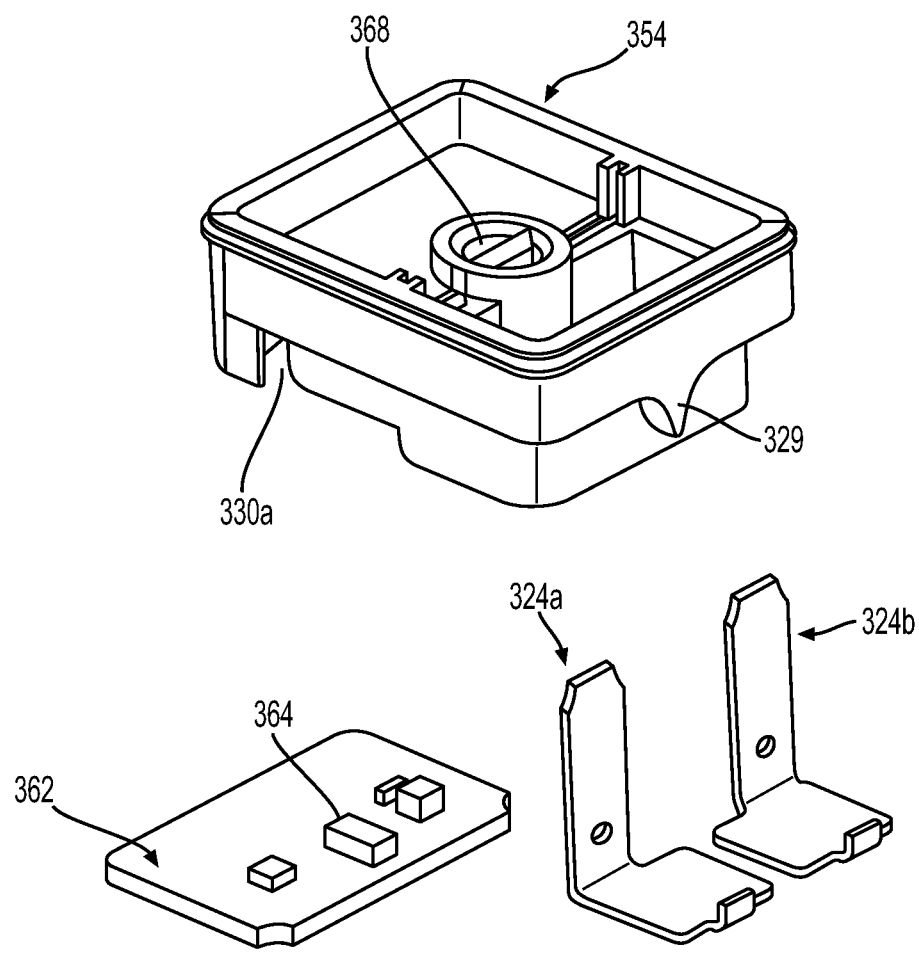
FIG. 19 is an exploded view of the connector module of FIG. 18.
Figure 20:
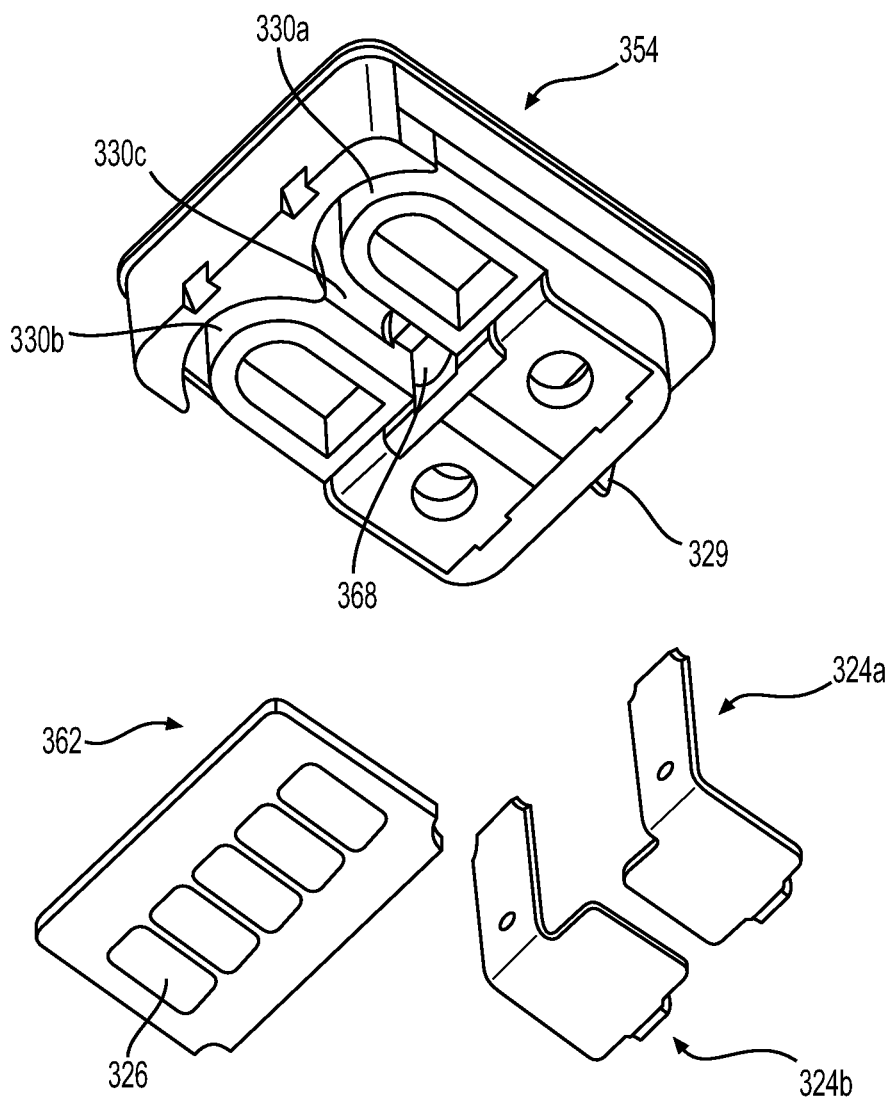
FIG. 20 is another exploded view of the connector module of FIG. 18.

FIG. 18 is a perspective view of the connector module of FIG. 17 without the wick and heater. FIG. 19 is an exploded view of the connector module of FIG. 18. FIG. 20 is another exploded view of the connector module of FIG. 18. Referring to FIGS. 18-20, the module housing 354 forms the framework of the connector module 320. The module housing 354 defines, inter alia, the divider 329 and the flow path for the air drawn into the pod assembly 300. The heating chamber is in fluidic communication with the flow path in the upstream side of the module housing 354 via a module outlet 368.

As noted supra, the flow path for the air drawn into the pod assembly 300 includes a first diverged portion, a second diverged portion, and a converged portion defined by the module housing 354. In an example embodiment, the first diverged portion and the second diverged portion are symmetrical portions bisected by an axis corresponding to the converged portion of the flow path. For instance, as shown in FIG. 20, the first diverged portion, the second diverged portion, and the converged portion may include a first curved path 330a, a second curved path 330b, and a converged path 330c, respectively. The first curved path 330a and the second curved path 330b may be substantially U-shaped paths, while the converged path 330c may be substantially a linear path. Based on an axis corresponding to the converged path 330c and aligned with a crest of the divider 329, the first diverged portion of the flow path may be a mirror image of the second diverged portion of the flow path. During vaping, the air drawn through the pod inlet 322 may be split by the divider 329 and initially flow in opposite directions away from the divider 329, followed by a subsequent flow in parallel before each air stream makes a U-turn (via the first curved path 330a and the second curved path 330b) and convenes (via the converged path 330c) for a combined flow that travels back toward the divider 329 prior to passing through the module outlet 368 to the heating chamber. The heater 336 and the wick 338 may be positioned such that both sides are exposed substantially equally to the combined flow of air passing through the module outlet 368. During vaping, the non-nicotine vapor generated is entrained by the combined flow of air traveling through the heating chamber to the vapor channel 316.

As illustrated in FIGS. 19-20, each of the first power contact 324a and the second power contact 324b may include a contact face and a contact leg. The contact leg (which may have an elongated configuration) may be oriented orthogonally relative to the contact face (which may be square-shaped), although example embodiments are not limited thereto. The module housing 354 may define a pair of shallow depressions and a pair of apertures to facilitate the mounting of the first power contact 324a and the second power contact 324b. During assembly, the contact face of each of the first power contact 324a and the second power contact 324b may be seated in a corresponding one of the pair of shallow depressions so as to be substantially flush with the external face of the module housing 354 (e.g., FIG. 16). In addition, the contact leg of each of the first power contact 324a and the second power contact 324b may extend through a corresponding one of the pair of apertures so as to protrude from the downstream side of the module housing 354 (e.g., FIG. 18). The heater 336 can be subsequently connected to the contact leg of each of the first power contact 324a and the second power contact 324b.

The printed circuit board (PCB) 362 includes the plurality of data contacts 326 on its upstream side (e.g., FIG. 20) and various electronic components, including a sensor 364, on its downstream side (e.g., FIG. 19). The sensor 364 may be positioned on the printed circuit board (PCB) 362 such that the sensor 364 is within the converged path 330c defined by the module housing 354. In an example embodiment, the printed circuit board (PCB) 362 (and associated components secured thereto) is an independent structure that is initially inserted into the receiving cavity in the downstream side of the second housing section 308 such that the data contacts 326 are exposed by the data contact opening 327 of the second housing section 308. Afterwards, the module housing 354 (with the first power contact 324a, the second power contact 324b, the heater 336, and the wick 338 mounted thereon) may be inserted into the receiving cavity such that the first power contact 324a and the second power contact 324b are exposed by the first power contact opening 325a and the second power contact opening 325b, respectively, of the second housing section 308. Alternatively, to simplify the above two-step insertion process to a one-step insertion process, it should be understood that the printed circuit board (PCB) 362 (and associated components secured thereto) may be affixed to the module housing 354 (e.g., to form a single integrated structure) so as to cover the first curved path 330a, the second curved path 330b, the converged path 330c, and the module outlet 368.

The module outlet 368 may be a resistance-to-draw (RTD) port. In such a configuration, the resistance-to-draw for the non-nicotine e-vaping device 500 may be adjusted by changing the size of the module outlet 368 (rather than changing the size of the pod inlet 322). In an example embodiment, the size of the module outlet 368 may be selected such that the resistance-to-draw is between 25-100 mmH$_2$O (e.g., between 30-50 mmH$_2$O). For instance, a diameter of 1.0 mm for the module outlet 368 may result in a resistance-to-draw of 88.3 mmH$_2$O. In another instance, a diameter of 1.1 mm for the module outlet 368 may result in a resistance-to-draw of 73.6 mmH$_2$O. In another instance, a diameter of 1.2 mm for the module outlet 368 may result in a resistance-to-draw of 58.7 mmH$_2$O. In yet another instance, a diameter of 1.3 mm for the module outlet 368 may result in a resistance-to-draw of about 40-43 mmH$_2$O. Notably, the size of the module outlet 368, because of its internal arrangement, may be adjusted without affecting the external aesthetics of the pod assembly 300, thereby allowing for a more standardized product design for pod assemblies with various resistance-to-draw (RTD) while also reducing the likelihood of an inadvertent blockage of the incoming air.

Example Non-Nicotine e-Vapor Device Systems

Example systems of the pod 300 and device body 100 of the non-nicotine e-vapor device 500 will now be discussed below with reference to FIGS. 21A-23.

Figure 21A:
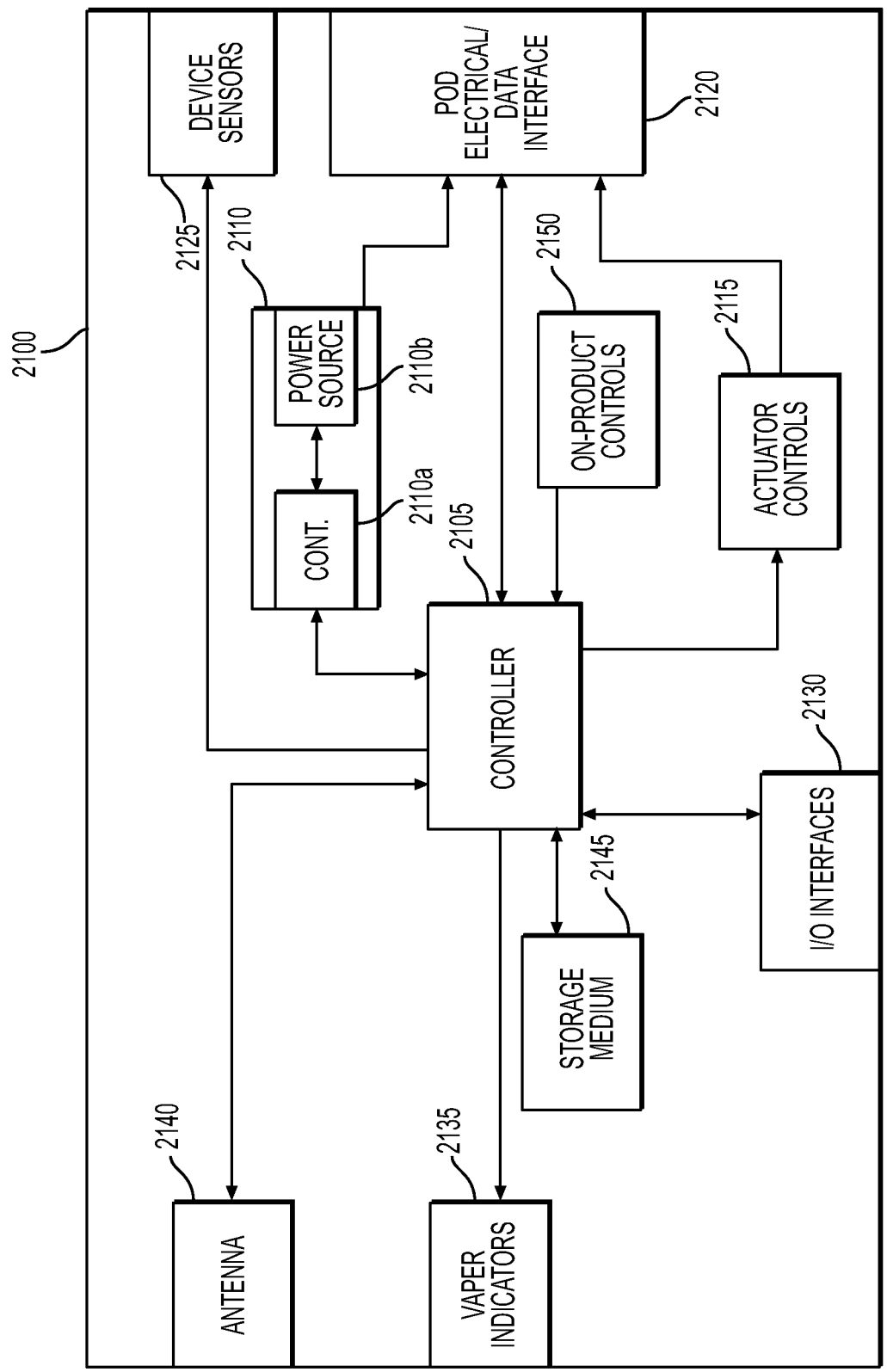
FIG. 21A illustrates a device system diagram of a dispensing body according to an example embodiment.

FIG. 21A illustrates a device system of a dispensing body according to an example embodiment. A device system 2100 may be a system within the device body 100 and the dispensing body.

The device system 2100 includes a controller 2105, a power supply 2110, actuator controls 2115, a pod electrical/data interface 2120, device sensors 2125, input/output (I/O) interfaces 2130, vaper indicators 2135, at least one antenna 2140 and a storage medium 2145. The device system 2100 is not limited to the features shown in FIG. 21A. For example, the device system 2100 may include additional elements. However, for the sake of brevity, the additional elements are not described. In other example embodiments, the device system 2100 may not include an antenna.

The controller 2105 may be hardware, firmware, hardware executing software, or any combination thereof. When the controller 2105 is hardware, such existing hardware may include one or more Central Processing Units (CPUs), microprocessors, processor cores, multiprocessors, digital signal processors (DSPs), application-specific-integrated-circuits (ASICs), field programmable gate arrays (FPGAs) computers or the like configured as special purpose machines to perform the functions of the controller 2105. CPUs, microprocessors, processor cores, multiprocessors, DSPs, ASICs and FPGAs may generally be referred to as processing devices.

In the event where the controller 2105 is, or includes, a processor executing software, the controller 2105 is configured as a special purpose machine (e.g., a processing device) to execute the software, stored in memory accessible by the controller 2105 (e.g., the storage medium 2145 or another storage device), to perform the functions of the controller 2105. The software may be embodied as program code including instructions for performing and/or controlling any or all operations described herein as being performed by the controller 2105 or the controller 2105A (FIG. 21B).

As disclosed herein, the term "storage medium", "computer readable storage medium" or "non-transitory computer readable storage medium" may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Figure 21B:
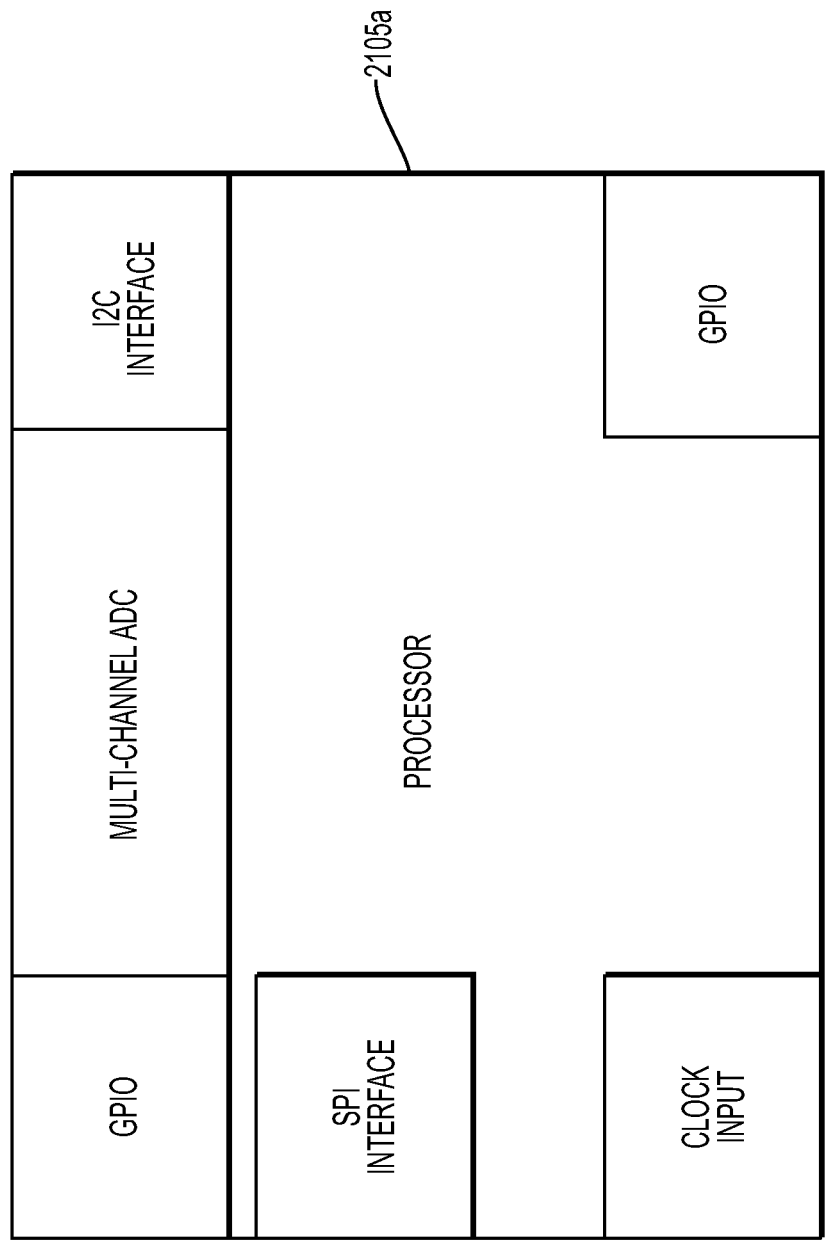
FIG. 21B illustrates an example of a controller in the device system of FIG. 21A according to an example embodiment.

FIG. 21B illustrates an example of a controller 2105A according to an example embodiment. According to an example embodiment, the controller 2105A illustrated in FIG. 21B is an example implementation of the controller 2105 illustrated in FIG. 21A. Accordingly, any operations described in the present specification as being performed or controlled by the controller 2105 may be performed or controlled by the controller 2105A. The controller 2105A may be on include a microprocessor. Further, the controller 2105A may include input/output interfaces, such as general purpose input/outputs (GPIOs), inter-integrated circuit (I²C) interfaces, serial peripheral interface bus (SPI) interfaces, or the like; a multichannel analog-to-digital converter (ADC); and a clock input terminal, as is shown in FIG. 21B. However, example embodiments should not be limited to this example. For example, the controller 2105A may further include a digital-to-analog converter and arithmetic circuitry or circuits.

Returning to FIG. 21A, the controller 2105 communicates with the power supply 2110, the actuator control 2115, the pod electrical/data interface 2120, the device sensors 2125, the input/output (I/O) interfaces 2130, the vaper indicators 2135, the on-product controls 2150, and the at least one antenna 2140.

The controller 2105 communicates with a cryptographic coprocessor with non-volatile memory (CC-NVM) or non-volatile memory (NVM) in the pod through the pod electrical/data interface 2120. The term CC-NVM may refer to a hardware module(s) including a processor for encryption and related processing and an NVM. More specifically, the controller 2105 may utilize encryption to authenticate the pod 300. As will be described, the controller 2105 communicates with the CC-NVM package or NVM to authenticate the pod 300. More specifically, the non-volatile memory may be encoded during manufacture with product and other information for authentication.

The memory device may be coded with an electronic identity to permit at least one of an authentication of the pod and a pairing of operating parameters specific to a type of the pod 300 (or physical construction, such as a heating engine type) when the pod 300 is inserted into the through-hole of the dispensing body. In addition to authenticating based on an electronic identity of the pod 300, the controller 2105 may authorize use of the pod based on an expiration date of the stored non-nicotine pre-vapor formulation and/or heater encoded into the NVM or the non-volatile memory of the CC-NVM. If the controller determines that the expiration date encoded into the non-volatile memory has passed, the controller may not authorize use of the pod and disable the non-nicotine e-vapor device 500.

The controller 2105 (or storage medium 2145) stores key material and proprietary algorithm software for the encryption. For example, encryption algorithms rely on the use of random numbers. The security of these algorithms depends on how truly random these numbers are. These numbers are usually pre-generated and coded into the processor or memory devices. Example embodiments may increase the randomness of the numbers used for the encryption by using the vapor drawing parameters e.g., durations of instances of vapor drawing, intervals between instances of vapor drawing, or combinations of them, to generate numbers that are more random and more varying from individual to individual than pre-generated random numbers. All communications between the controller 2105 and the pod may be encrypted.

Moreover, the pod can be used as a general pay-load carrier for other information such as software patches for the non-nicotine e-vapor device 500. Since encryption is used in all the communications between the pod and the controller 2105, such information is more secure and the non-nicotine e-vapor device 500 is less prone to being installed with malwares or viruses. Use of the CC-NVM as an information carrier such as data and software updates allows the non-nicotine e-vapor device 500 to be updated with software without it being connected to the Internet and for an adult vaper to go through a downloading process as with most other consumer electronics devices requiring periodic software updates.

The controller 2105 may also include a cryptographic accelerator to allow resources of the controller 2105 to perform functions other than the encoding and decoding involved with the authentication. The controller 2105 may also include other security features such as preventing unauthorized use of communication channels and preventing unauthorized access to data if a pod or adult vaper is not authenticated.

In addition to a cryptographic accelerator, the controller 2105 may include other hardware accelerators. For example, the controller 2105 may include a floating point unit (FPU), a separate DSP core, digital filters and Fast Fourier Transform (FFT) modules.

The controller 2105 is configured to operate a real time operating system (RTOS), control the device system 2100 and may be updated through communicating with the NVM or CC-NVM or when the device system 2100 is connected with other devices (e.g., a smart phone) through the I/O interfaces 2130 and/or the antenna 2140. The I/O interfaces 2130 and the antenna 2140 allow the device system 2100 to connect to various external devices such as smart phones, tablets, and PCs. For example, the I/O interfaces 2130 may include a micro-USB connector. The micro-USB connector may be used by the device system 2100 to charge the power source 2110b.

The controller 2105 may include on-board RAM and flash memory to store and execute code including analytics, diagnostics and software upgrades. As an alternative, the storage medium 2145 may store the code. Additionally, in another example embodiment, the storage medium 2145 may be on-board the controller 2105.

The controller 2105 may further include on-board clock, reset and power management modules to reduce an area covered by a PCB in the dispensing body.

The device sensors 2125 may include a number of sensor transducers that provide measurement information to the controller 2105. The device sensors 2125 may include a power supply temperature sensor, an external pod temperature sensor, a current sensor for the heater, power supply current sensor, air flow sensor and an accelerometer to monitor movement and orientation. The power supply temperature sensor and external pod temperature sensor may be a thermistor or thermocouple and the current sensor for the heater and power supply current sensor may be a resistive based sensor or another type of sensor configured to measure current. The air flow sensor may be a microelectromechanical system (MEMS) flow sensor or another type of sensor configured to measure air flow such as a hot-wire anemometer. As noted above, the device sensors 2125 may include sensors, like an accelerometer, for monitoring movement and orientation as is shown in, for example, FIG. 23.

Figure 23:
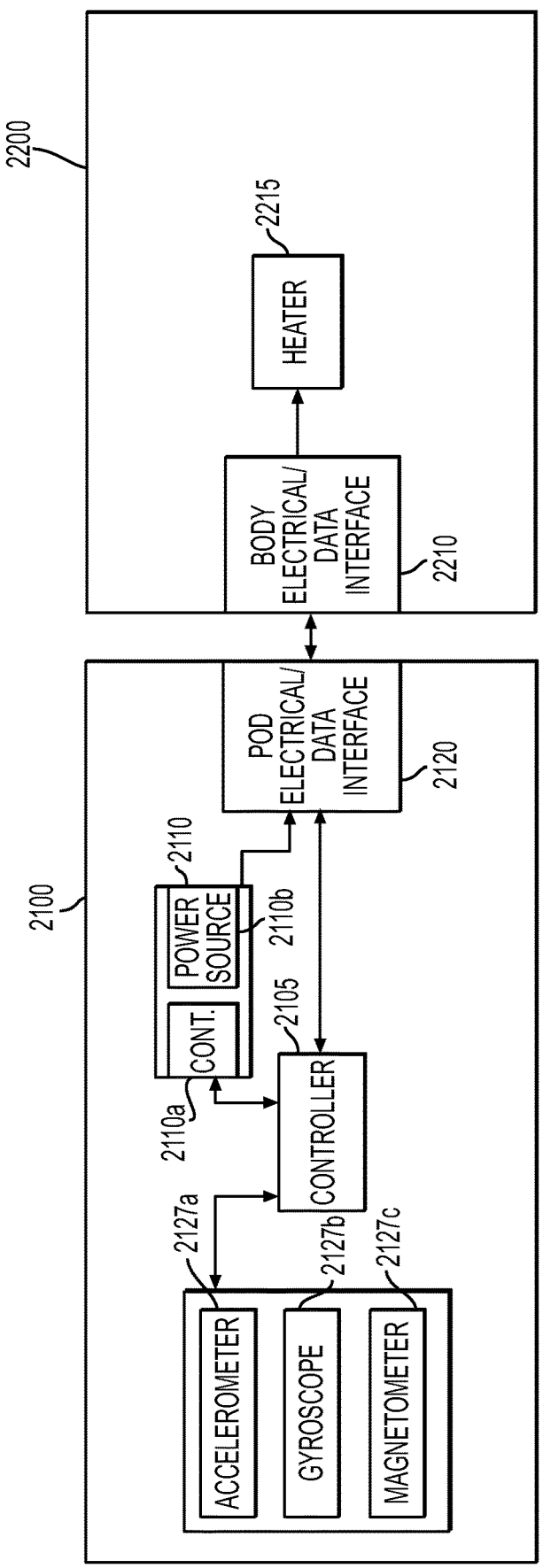
FIG. 23 illustrates a pod system connected to a device system according to an example embodiment.

FIG. 23 illustrates the pod system 2200 connected to the device system 2100 according to an example embodiment. For example, the device sensors 2125 may include one or more accelerometers 2127A, one or more gyroscopes 2127B, and/or one or more magnetometers 2127C to monitor movement and orientation. For example, the device sensors 2125 may include at least one inertial measurement unit (IMU). The IMU may include, for example, 3-axis accelerometers, 3-axis-gyroscopes and 3-axis magnetometers. For example, the one or more accelerometers 2127A, one or more gyroscopes 2127B, and/or one or more magnetometers 2127C of FIG. 23 may be included in an IMU. Examples of an IMU included in the device sensors 2125 include, but are not limited to, the Invensense 10-axis MPU-9250 and the ST 9-axis STEVAL-MKI1119V1. As will be discussed in greater detail below with respect to FIGS. 24-25, the controller 2105 may use movement and/or orientation information detected by the device sensors 2125 to control a level of power output by the power supply 2110 to the heater 2215 through the pod electrical/data interface 2120 and the body electrical/data interface 2210.

The data generated from the number of sensor transducers may be sampled at a sample rate appropriate to the parameter being measured using a discrete, multi-channel analog-to-digital converter (ADC).

The controller 2105 may adapt heater profiles for a non-nicotine pre-vapor formulation and other profiles based on the measurement information received from the controller 2105. For the sake of convenience, these are generally referred to as vaping or vapor profiles.

The heater profile identifies the power profile to be supplied to the heater during the few seconds when vapor drawing takes place. For example, a heater profile can deliver maximum power to the heater when an instance of vapor drawing is initiated, but then after a second or so immediately reduce the power to half way or a quarter way.

In addition, a heater profile can also be modified based on a negative pressure applied on the non-nicotine e-vapor device 500. The use of the MEMS flow sensor allows vapor drawing strength to be measured and used as feedback to the controller 2105 to adjust the power delivered to the heater of the pod 300, which may be referred to as heating or energy delivery.

When the controller 2105 recognizes a pod that is currently installed (e.g., via SKU), the controller 2105 matches an associated heating profile that is designed for that particular pod. The controller 2105 and the storage medium 2145 will store data and algorithms that allow the generation of heating profiles for all SKUs. In another example embodiment, the controller 2105 may read the heating profile from the pod. The adult vapers may also adjust heating profiles to suit their preferences.

As shown in FIG. 21A, the controller 2105 sends data to and receives data from the power supply 2110. The power supply 2110 includes a power source 2110b and a power controller 2110a to manage the power output by the power source 2110b.

The power source 2110b may be a Lithium-ion battery or one of its variants, for example a Lithium-ion polymer battery. Alternatively, the power source 2110b may be a Nickel-metal hydride battery, a Nickel cadmium battery, a Lithium-manganese battery, a Lithium-cobalt battery or a fuel cell. Alternatively, the power source 2110b may be rechargeable and include circuitry allowing the battery to be chargeable by an external charging device. In that case, the circuitry, when charged, provides power for a desired (or alternatively a pre-determined) number of instances of vapor drawing, after which the circuitry must be re-connected to an external charging device.

The power controller 2110a provides commands to the power source 2110b based on instructions from the controller 2105. For example, the power supply 2110 may receive a command from the controller 2105 to provide power to the pod (through the pod electrical/data interface 2120) when the pod is authenticated and the adult vaper activates the device system 2100 (e.g., by activating a switch such as a toggle button, capacitive sensor, IR sensor). When the pod is not authenticated, the controller 2105 may either send no command to the power supply 2110 or send an instruction to the power supply 2110 to not provide power. In another example embodiment, the controller 2105 may disable all operations of the device system 2100 if the pod is not authenticated.

In addition to supplying power to the pod 300, the power supply 2110 also supplies power to the controller 2105.

Moreover, the power controller 2110a may provide feedback to the controller 2105 indicating performance of the power source 2110b.

The controller 2105 sends data to and receives data from the at least one antenna 2140. The at least one antenna 2140 may include a Near Field Communication (NFC) modem and a Bluetooth Low Energy (LE) modem and/or other modems for other wireless technologies (e.g., Wi-Fi). In an example embodiment, the communications stacks are in the modems, but the modems are controlled by the controller 2105. The Bluetooth LE modem is used for data and control communications with an application on an external device (e.g., smart phone). The NFC modem may be used for pairing of the non-nicotine e-vapor device 500 to the application and retrieval of diagnostic information. Moreover, the Bluetooth LE modem may be used to provide location information (for an adult vaper to find the non-nicotine e-vapor device 500) or authentication during a purchase. Further, according to at least some example embodiments, the non-nicotine e-vapor device 500 (e.g., the controller 2105) may be configured to use a Bluetooth communications capability (e.g., provided by the Bluetooth LE modem) to selectively lock the non-nicotine e-vapor device 500. For example, an adult vapor can use an application (e.g., app) installed on an external mobile device (e.g., a mobile phone) with Bluetooth communications capability to lock the non-nicotine e-vapor device 500, thus preventing the non-nicotine e-vapor device 500 from operating to produce a non-nicotine vapor, and un-lock the non-nicotine e-vapor device 500, thus allowing the non-nicotine e-vapor device 500 to operate to produce a non-nicotine vapor. Additionally, according to at least some example embodiments, the adult vaper can choose a setting on the application to control the non-nicotine e-vapor device 500 such that the non-nicotine e-vapor device 500 remains locked (i.e., prevented from operating to produce a vapor) until the non-nicotine e-vapor device 500 is within a desired range of the electronic device on which the application is installed. For example, the adult vaper can use the application to set the non-nicotine e-vapor device 500 to remain locked until the non-nicotine e-vapor device 500 is within Bluetooth communication range of the electronic device on which the application is installed. For example, according to at least some example embodiments, the adult vaper can use the application to set the non-nicotine e-vapor device 500 such that the non-nicotine e-vapor device locks when the non-nicotine e-vapor device 500 is not paired with the electronic device on which the application is installed, and remains locked until the non-nicotine e-vapor device 500 is paired with the electronic device on which the application is installed.

As described above, the device system 2100 may generate and adjust various profiles for vaping. The controller 2105 uses the power supply 2110 and the actuator controls 2115 to regulate the profile for the adult vaper.

The actuator controls 2115 include passive and active actuators to regulate a desired vapor profile. For example, the dispensing body may include an inlet channel within a mouthpiece. The actuator controls 2115 may control the inlet channel based on commands from the controller 2105 associated with the desired vapor profile.

Moreover, the actuator controls 2115 are used to energize the heater in conjunction with the power supply 2110. More specifically, the actuator controls 2115 are configured to generate a drive waveform associated with the desired vaping profile. As described above, each possible profile is associated with a drive waveform. Upon receiving a command from the controller 2105 indicating the desired vaping profile, the actuator controls 2115 may produce the associated modulating waveform for the power supply 2110.

The controller 2105 supplies information to the vaper indicators 2135 to indicate statuses and occurring operations to the adult vaper. The vaper indicators 2135 include a power indicator (e.g., LED) that may be activated when the controller 2105 senses a button pressed by the adult vaper. The vaper indicators 2135 may also include a vibrator, speaker, an indicator for current state of an adult vaper-controlled vaping parameter (e.g., vapor volume) and other feedback mechanisms.

Furthermore, the device system 2100 may include a number of on-product controls 2150 that provide commands from an adult vaper to the controller 2105. The on-product controls 2150 include an on-off button which may be a toggle button, capacitive sensor or IR sensor, for example. The on-product controls 2150 may further include a vaping control button (if the adult vaper desires to override the buttonless vaping feature to energize the heater), a hard reset button, a touch based slider control (for controlling setting of a vaping parameter such as vapor drawing volume), a vaping control button to activate the slider control and a mechanical adjustment for an air inlet. Hand to mouth gesture (HMG) detection is another example of buttonless vaping. Further, a combination of key strokes (e.g., key strokes entered by an adult vaper via the on-product controls 2150) can be used to lock the non-nicotine e-vapor device and prevent the device from operating to produce vapor. According to at least some example embodiments, the combination of key strokes may be set by a manufacturer of the non-nicotine e-vapor device 500 and/or the device system 2100. According to at least some example embodiments, the combination of key strokes may be set, or changed, by an adult vaper (e.g., by key strokes entered by the adult vaper via the on-product controls 2150).

Once a pod is authenticated (e.g., in the manner discussed above with reference to FIG. 21A), the controller 2105 operates the power supply 2110, the actuator controls 2115, vaper indicators 2135 and antenna 2140 in accordance with the adult vaper using the non-nicotine e-vapor device 500 and the information stored by the NVM or CC-NVM on the pod 300. Moreover, the controller 2105 may include logging functions and be able to implement algorithms to calibrate the non-nicotine e-vapor device 500. The logging functions are executed by the controller 2105 to record usage data as well any unexpected events or faults. The recorded usage data may be used for diagnostics and analytics. The controller 2105 may calibrate the non-nicotine e-vapor device 500 using buttonless vaping (i.e., vaping without pressing a button such as generating a non-nicotine vapor when a negative pressure is applied on the mouthpiece), an adult vaper configuration and the stored information on the CC-NVM or NVM including vapor drawing sensing, non-nicotine pre-vapor formulation level and non-nicotine pre-vapor formulation composition. For example, the controller 2105 may command the power supply 2110 to supply power to the heater in the pod based on a vaping profile associated with the non-nicotine pre-vapor formulation composition in the pod 300. Alternatively, a vaping profile may be encoded in the CC-NVM or NVM and utilized by the controller 2105.

Figure 22A:
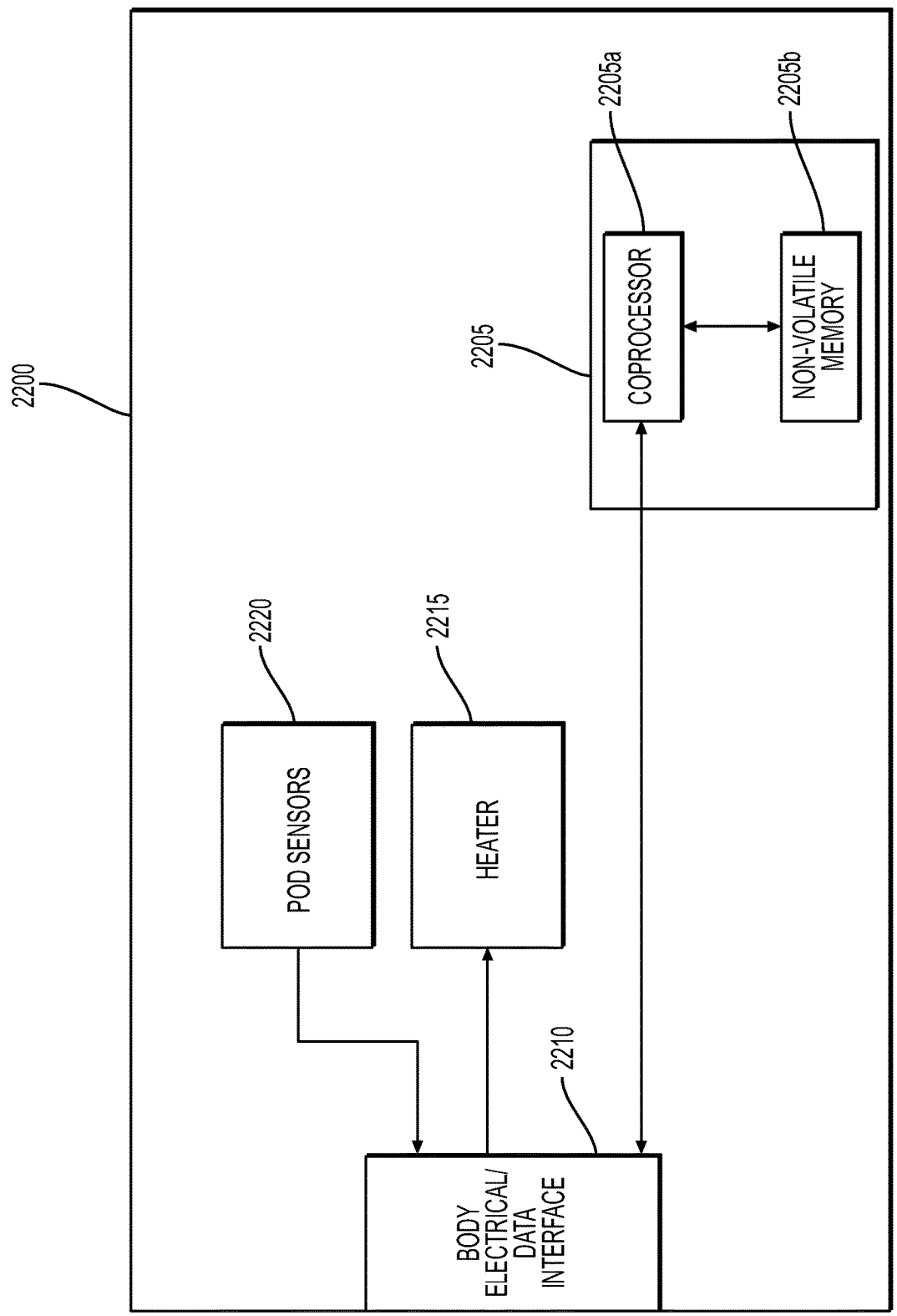
FIG. 22A illustrates a pod system diagram of a dispensing body according to an example embodiment.

FIG. 22A illustrates a pod system diagram of a dispensing body according to an example embodiment. A pod system 2200 may be within the pod assembly 300.

As shown in FIG. 22A, the pod system 2200 includes a CC-NVM 2205, a body electrical/data interface 2210, a heater 2215 and pod sensors 2220. The pod system 2200 communicates with the device system 2100 through the body electrical/data interface 2210 and the pod electrical/data interface 2120. The body electrical/data interface 2210 may correspond to the battery contacts 416 and data connection 417 connected within the pod assembly 300, shown in FIG. 19, for example. Thus, the CC-NVM 2205 is coupled to the data connection 417 and the battery contacts 416.

The CC-NVM 2205 includes a cryptographic coprocessor 2205a and a non-volatile memory 2205b. The controller 2105 may access the information stored on the non-volatile memory 2205b for the purposes of authentication and operating the pod by communicating with the cryptographic coprocessor 2205a.

In another example embodiment, the pod may not have a cryptographic coprocessor. For example, FIG. 22B illustrates an example of the pod system of FIG. 22A in which the cryptographic coprocessor 2205a is omitted, according to an example embodiment. As is shown in FIG. 22B, the pod system 2200 may include the non-volatile memory 2205b in place of the CC-NVM 2205, and the cryptographic coprocessor 2205a is omitted. When no cryptographic coprocessor exists in the pod system 2200, the controller 2105 may read data from the non-volatile memory 2205b without use of the cryptographic coprocessor to control/define the heating profile.

The non-volatile memory 2205b may be coded with an electronic identity to permit at least one of an authentication of the pod 300 and a pairing of operating parameters specific to a type of the pod 300 when the pod 300 is inserted into the through-hole of the device body 100. In addition to authenticating based on an electronic identity of the pod 300, the controller 2105 may authorize use of the pod based on an expiration date of the stored non-nicotine pre-vapor formulation and/or heater encoded into the non-volatile memory 2205b. If the controller determines that the expiration date encoded into the non-volatile memory non-volatile memory 2205b has passed, the controller may not authorize use of the pod and disable the non-nicotine e-vapor device 500.

Moreover, the non-volatile memory 2205b may store information such as a stock keeping unit (SKU) of the non-nicotine pre-vapor formulation in the non-nicotine pre-vapor formulation compartment (including non-nicotine pre-vapor formulation composition), software patches for the device system 2100, product usage information such as vapor drawing instance count, vapor drawing instance duration, and non-nicotine pre-vapor formulation level. The non-volatile memory 2205b may store operating parameters specific to the type of the pod and the non-nicotine pre-vapor formulation composition. For example, the non-volatile memory 2205b may store the electrical and mechanical design of the pod for use by the controller 2105 to determine commands corresponding to a desired vaping profile.

The non-nicotine pre-vapor formulation level in the pod may be determined in one of two ways, for example. In one example embodiment, one of the pod sensors 2220 directly measures the non-nicotine pre-vapor formulation level in the pod 300.

In another example embodiment, the non-volatile memory 2205b stores the vapor drawing instance count from the pod and the controller 2105 uses the vapor drawing instance count as a proxy to the amount of non-nicotine pre-vapor formulation vaporized.

The controller 2105 and/or the storage medium 2145 may store non-nicotine pre-vapor formulation calibration data that identifies an operating point for the non-nicotine pre-vapor formulation composition. The non-nicotine pre-vapor formulation calibration data include data describing how flow rate changes with a remaining non-nicotine pre-vapor formulation level or how volatility changes with an age of the non-nicotine pre-vapor formulation and may be used for calibration by the controller 2105. The non-nicotine pre-vapor formulation calibration data may be stored by the controller 2105 and/or the storage medium 2145 in a table format. The non-nicotine pre-vapor formulation calibration data allows the controller 2105 to equate the vapor drawing instance count to the amount of non-nicotine pre-vapor formulation vaporized.

The controller 2105 writes the non-nicotine pre-vapor formulation level and vapor drawing instance count back to the non-volatile memory 2205b in the pod so if the pod is removed from the dispensing body and later on re-installed, an accurate non-nicotine pre-vapor formulation level of the pod will still be known by the controller 2105.

The operating parameters (e.g., power supply, power duration, air channel control) are referred to as a vaping profile. Moreover, the non-volatile memory 2205b may record information communicated by the controller 2105. The non-volatile memory 2205b may retain the recorded information even when the dispensing body becomes disconnected from the pod 300.

In an example embodiment, the non-volatile memory 2205b may be a programmable read only memory.

The heater 2215 is actuated by the controller 2105 and transfers heat to at least a portion of the non-nicotine pre-vapor formulation in accordance with the commanded profile (volume, temperature (based on power profile) and flavor) from the controller 2105.

The heater 2215 may be a planar body, a ceramic body, a single wire, a cage of resistive wire, a wire coil surrounding a wick, a mesh, a surface or any other suitable form for example. Examples of suitable electrically resistive materials include titanium, zirconium, tantalum and metals from the platinum group. Examples of suitable metal alloys include stainless steel, nickel-, cobalt-, chromium-, aluminum-titanium-zirconium-, hafnium-, niobium-, molybdenum-, tantalum-, tungsten-, tin-, gallium-, manganese- and iron-containing alloys, and super-alloys based on nickel, iron, cobalt, stainless steel. For example, the heater may be formed of nickel aluminides, a material with a layer of alumina on the surface, iron aluminides and other composite materials, the electrically resistive material may optionally be embedded in, encapsulated or coated with an insulating material or vice-versa, depending on the kinetics of energy transfer and the external physicochemical properties required. In one embodiment, the heater 2215 comprises at least one material selected from the group consisting of stainless steel, copper, copper alloys, nickel-chromium alloys, superalloys and combinations thereof. In an embodiment, the heater 2215 is formed of nickel-chromium alloys or iron-chromium alloys. In one embodiment, the heater 2215 can be a ceramic heater having an electrically resistive layer on an outside surface thereof.

In another embodiment, the heater 2215 may be constructed of an iron-aluminide (e.g., FeAl or $Fe_3Al$), such as those described in commonly owned U.S. Pat. No. 5,595,706 to Sikka et al. filed Dec. 29, 1994, or nickel aluminides (e.g., $Ni_3Al$), the entire contents of which are hereby incorporate by reference.

The heater 2215 may determine an amount of non-nicotine pre-vapor formulation to heat based on feedback from the pod sensors or the controller 2105. The flow of non-nicotine pre-vapor formulation may be regulated by a micro-capillary or wicking action. Moreover, the controller 2105 may send commands to the heater 2215 to adjust an air inlet to the heater 2215.

The pod sensor 2220 may include a heater temperature sensor, non-nicotine pre-vapor formulation flow rate monitor and air flow monitor. The heater temperature sensor may be a thermistor or thermocouple and the flow rate sensing may be performed by the pod system 2200 (e.g., under the control of the controller 2105 or a controller included in the pod system 2200) using electrostatic interference or an in-non-nicotine pre-vapor formulation rotator. The air flow sensor may be a microelectromechanical system (MEMS) flow sensor or another type of sensor configured to measure air flow.

The data generated from the pod sensors 2220 may be sampled at a sample rate appropriate to the parameter being measured using a discrete, multi-channel analog-to-digital converter (ADC).

According to at least some example embodiments, the controller 2105 may also control the heater 2215 in response to detecting a hand to mouth gesture (HMG). As is noted above, with reference to FIG. 21A, a non-nicotine e-vapor device according to at least some example embodiments may implement a buttonless vaping feature. As an example of a buttonless vaping feature, the controller 2105 may determine when an adult vaper makes a HMG based on measurements from device sensors 2125. An HMG is a gesture in which an adult vaper's hand moves towards the adult vaper's mouth. An HMG made with respect to a non-nicotine e-vapor device (e.g., the non-nicotine e-vapor device 500 and/or a non-nicotine e-vapor device including device body 100) may indicate that vapor drawing will begin soon. According to at least some example embodiments, the controller 2105 may control a state and/or operation mode of the non-nicotine e-vapor device or one or more elements thereof based on the detection of an HMG. For example, the controller 2105 may control a state and/or operation mode of the heater 2215 by detecting an HMG.

As is noted above, the heater 2215 may be actuated by the controller 2105. According to at least some example embodiments, the controller 2105 may control the heater 2215 using a heating engine control algorithm and a heating engine driver implemented by the controller 2105. The heater 2215 may also be referred to, herein, as the heating engine 2215 or heater engine 2215. Example structures of a heat-not-burn aerosol-generating device will now be discussed below with reference to FIGS. 27-31.

Example Heat-not-Burn Aerosol-Generating Device Structures

Figure 27:
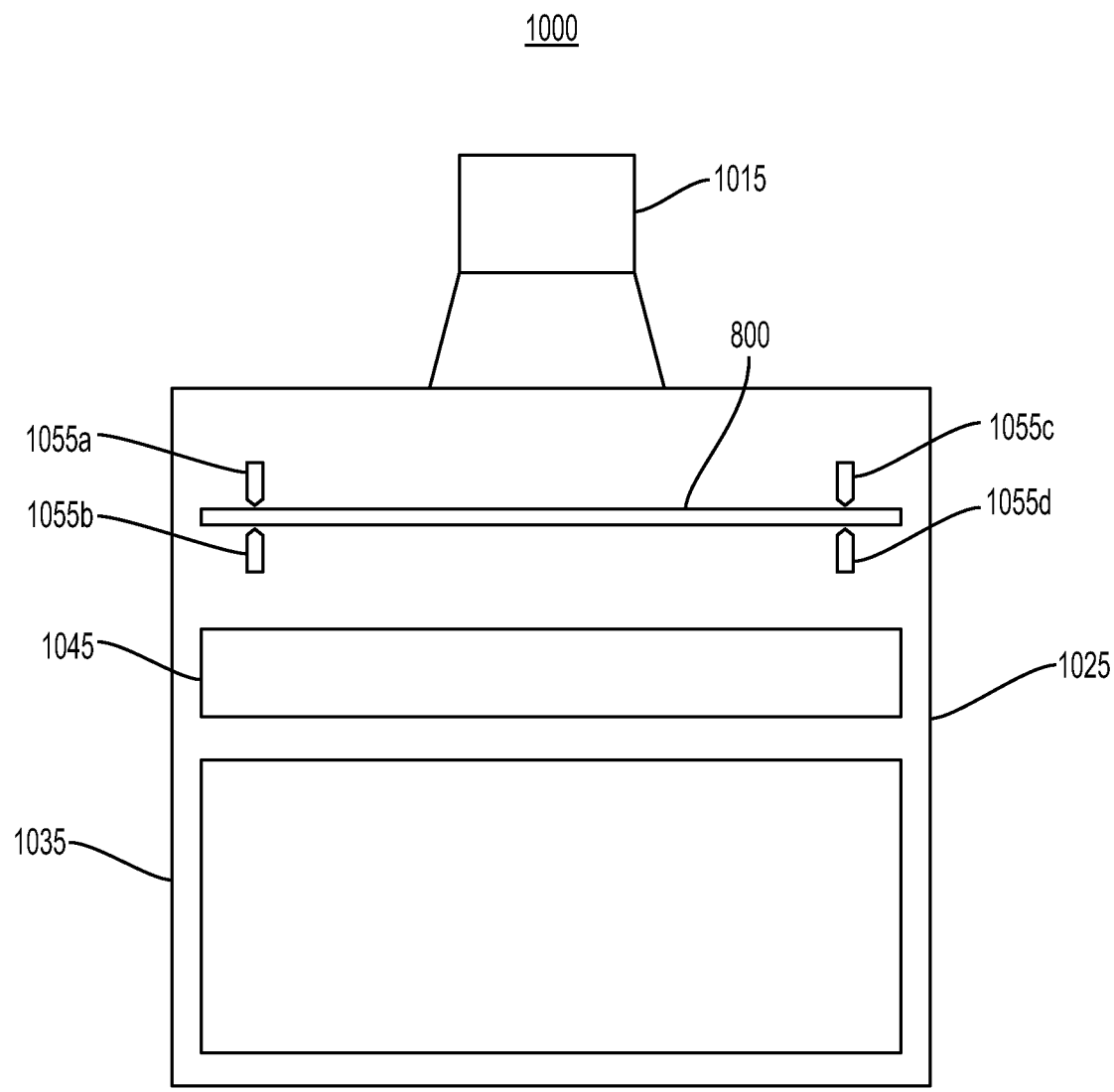
FIG. 27 is a schematic view of a heat-not-burn aerosol-generating device according to an example embodiment.

FIG. 27 is a schematic view of a heat-not-burn aerosol-generating device according to an example embodiment. Referring to FIG. 27, a heat-not-burn aerosol-generating device 1000 may include a mouthpiece 1015 and a device body 1025. A power source 1035 and control circuitry 1045 may be disposed within the device body 1025 of the heat-not-burn aerosol-generating device 1000. The heat-not-burn aerosol-generating device 1000 is configured to receive a capsule 800. The capsule 800, like the pod 300 of the non-nicotine e-vaping device 500 discussed, is a removable container. According to at least some example embodiments, the capsule 800 may include an aerosol-forming substrate sandwiched in between first and second heaters. According to at least some example embodiments, the first and second heaters may be planar and may be formed of a material that heats up when an electric current is applied thereto. The heat-not-burn aerosol-generating device 1000 may also include a first electrode 1055a, a second electrode 1055b, a third electrode 1055c, and a fourth electrode 1055d configured to electrically contact the capsule 800. According to at least some example embodiments, the first electrode 1055a and the third electrode 1055c may electrically contact the first heater, while the second electrode 1055b and the fourth electrode 1055d may electrically contact the second heater. However, in non-limiting embodiments involving a capsule with only one heater, it should be understood that the first electrode 1055a and the third electrode 1055c (or the second electrode 1055b and the fourth electrode 1055d) may be omitted.

As used herein, the term "aerosol-forming substrate" refers to a material (or combination of materials) that may yield an aerosol. As referred to herein, an "aerosol" is any matter generated or outputted from any heat-not-burn aerosol-generating device according to any of the example embodiments disclosed herein. The material is in a solid form and is a predominant source of a compound (e.g., a cannabinoid), wherein an aerosol including the compound is produced when the material is heated. The heating may be below the combustion temperature so as to produce an aerosol without involving a substantial pyrolysis of the aerosol-forming substrate or the substantial generation of combustion byproducts (if any). Thus, according to at least some example embodiments, pyrolysis does not occur during the heating and resulting production of aerosol. In other instances, there may be some pyrolysis and combustion byproducts, but the extent may be considered relatively minor and/or merely incidental. For example, once a heat-not-burn aerosol-generating device heats an aerosol-forming substrate to an aerosolization temperature, the aerosol-forming substrate may yield an aerosol. As used herein, the "aerosolization temperature" of an aerosol-forming substrate is the temperature at which the aerosol-forming substrate yields an aerosol, and is below the combustion temperature of the aerosol-forming substrate.

The aerosol-forming substrate may be a fibrous material. For instance, the fibrous material may be a botanical material. The fibrous material is configured to release a compound when heated. The compound may be a naturally occurring constituent of the fibrous material. For instance, the fibrous material may be plant material such as tobacco, and the compound released may be nicotine. The term "tobacco" includes any tobacco plant material including tobacco leaf, tobacco plug, reconstituted tobacco, compressed tobacco, shaped tobacco, or powder tobacco, and combinations thereof from one or more species of tobacco plants, such as *Nicotiana rustica* and *Nicotiana tabacum*.

In some example embodiments, the tobacco material may include material from any member of the genus *Nicotiana*. In addition, the tobacco material may include a blend of two or more different tobacco varieties. Examples of suitable types of tobacco materials that may be used include, but are not limited to, flue-cured tobacco, Burley tobacco, Dark tobacco, Maryland tobacco, Oriental tobacco, rare tobacco, specialty tobacco, blends thereof, and the like. The tobacco material may be provided in any suitable form, including, but not limited to, tobaccolamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass. Furthermore, in some instances, the tobacco material may be mixed and/or combined with at least one of propylene glycol, glycerin, sub-combinations thereof, or combinations thereof.

The compound may also be a naturally occurring constituent of a medicinal plant that has a medically-accepted therapeutic effect. For instance, the medicinal plant may be a cannabis plant, and the compound may be a cannabinoid. Cannabinoids interact with receptors in the body to produce a wide range of effects. As a result, cannabinoids have been used for a variety of medicinal purposes (e.g., treatment of pain, nausea, epilepsy, psychiatric disorders). The fibrous material may include the leaf and/or flower material from one or more species of cannabis plants such as *Cannabis sativa*, *Cannabis indica*, and *Cannabis ruderalis*. In some instances, the fibrous material is a mixture of 60-80% (e.g., 70%) *Cannabis sativa* and 20-40% (e.g., 30%) *Cannabis indica*.

Examples of cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (TI-ICA) is a precursor of tetrahydrocannabinol (THC), while cannabidiolic acid (CBDA) is precursor of cannabidiol (CBD). Tetrahydrocannabinolic acid (THCA) and cannabidiolic acid (CBDA) may be converted to tetrahydrocannabinol (THC) and cannabidiol (CBD), respectively, via heating. In an example embodiment, heat from the first heater and/or the second heater may cause decarboxylation so as to convert the tetrahydrocannabinolic acid (THCA) in the capsule (e.g., capsule 800 or 900) to tetrahydrocannabinol (THC), and/or to convert the cannabidiolic acid (CBDA) in the capsule to cannabidiol (CBD).

In instances where both tetrahydrocannabinolic acid (THCA) and tetrahydrocannabinol (THC) are present in the capsule, the decarboxylation and resulting conversion will cause a decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC) during the heating of the capsule. Similarly, in instances where both cannabidiolic acid (CBDA) and cannabidiol (CBD) are present in the capsule, the decarboxylation and resulting conversion will cause a decrease in cannabidiolic acid (CBDA) and an increase in cannabidiol (CBD). At least 50% (e.g., at least 87%) of the cannabidiolic acid (CBDA) may be converted to cannabidiol (CBD) during the heating of the capsule.

Furthermore, the compound may be or may additionally include a non-naturally occurring additive that is subsequently introduced into the fibrous material. In one instance, the fibrous material may include at least one of cotton, polyethylene, polyester, rayon, combinations thereof, or the like (e.g., in a form of a gauze). In another instance, the fibrous material may be a cellulose material (e.g., non-tobacco and/or non-cannabis material). In either instance, the compound introduced may include nicotine, cannabinoids, and/or flavorants. The flavorants may be from natural sources, such as plant extracts (e.g., tobacco extract, cannabis extract), and/or artificial sources. In yet another instance, when the fibrous material includes tobacco and/or cannabis, the compound may be or may additionally include one or more flavorants (e.g., menthol, mint, vanilla). Thus, the compound within the aerosol-forming substrate may include naturally occurring constituents and/or non-naturally occurring additives. In this regard, it should be understood that existing levels of the naturally occurring constituents of the aerosol-forming substrate may be increased through supplementation. For example, the existing levels of nicotine in a quantity of tobacco may be increased through supplementation with an extract containing nicotine. Similarly, the existing levels of one or more cannabinoids in a quantity of cannabis may be increased through supplementation with an extract containing such cannabinoids.

According to at least some example embodiments, when the capsule 800 is inserted into the heat-not-burn aerosol-generating device 1000, the control circuitry 1045 may instruct the power source 1035 to supply an electric current to the first electrode 1055a, the second electrode 1055b, the third electrode 1055c, and/or the fourth electrode 1055d. The supply of current from the power source 1035 may be in response to a manual operation (e.g., button-activation) or an automatic operation (e.g., puff-activation). As a result of the current, the capsule 800 may be heated to generate an aerosol.

Additional details of the capsule 800 and the heat-not-burn aerosol-generating device 1000, including the mouthpiece 1015, the device body 1025, the power source 1035, the control circuitry 1045, the first electrode 1055a, the second electrode 1055b, the third electrode 1055c, and the fourth electrode 1055d may be found in U.S. application Ser. No. 15/845,501, filed Dec. 18, 2017, titled "VAPORIZING DEVICES AND METHODS FOR DELIVERING A COMPOUND USING THE SAME,", the disclosure of which is incorporated herein in its entirety by reference. The capsule, aerosol-forming substrate, and related aspects discussed herein are also described in more detail in U.S. application Ser. No. 16/252,951, filed Jan. 21, 2019, titled "CAPSULE, HEAT-NOT-BURN (HNB) AEROSOL-GENERATING DEVICES, AND METHODS OF GENERATING AN AEROSOL,", and U.S. application Ser. No. 16/451,662, filed Jun. 25, 2019, titled "CAPSULES, HEAT-NOT-BURN (HNB) AEROSOL-GENERATING DEVICES, AND METHODS OF GENERATING AN AEROSOL," the disclosures of each of which are incorporated herein in their entirety by reference.

Figure 28:
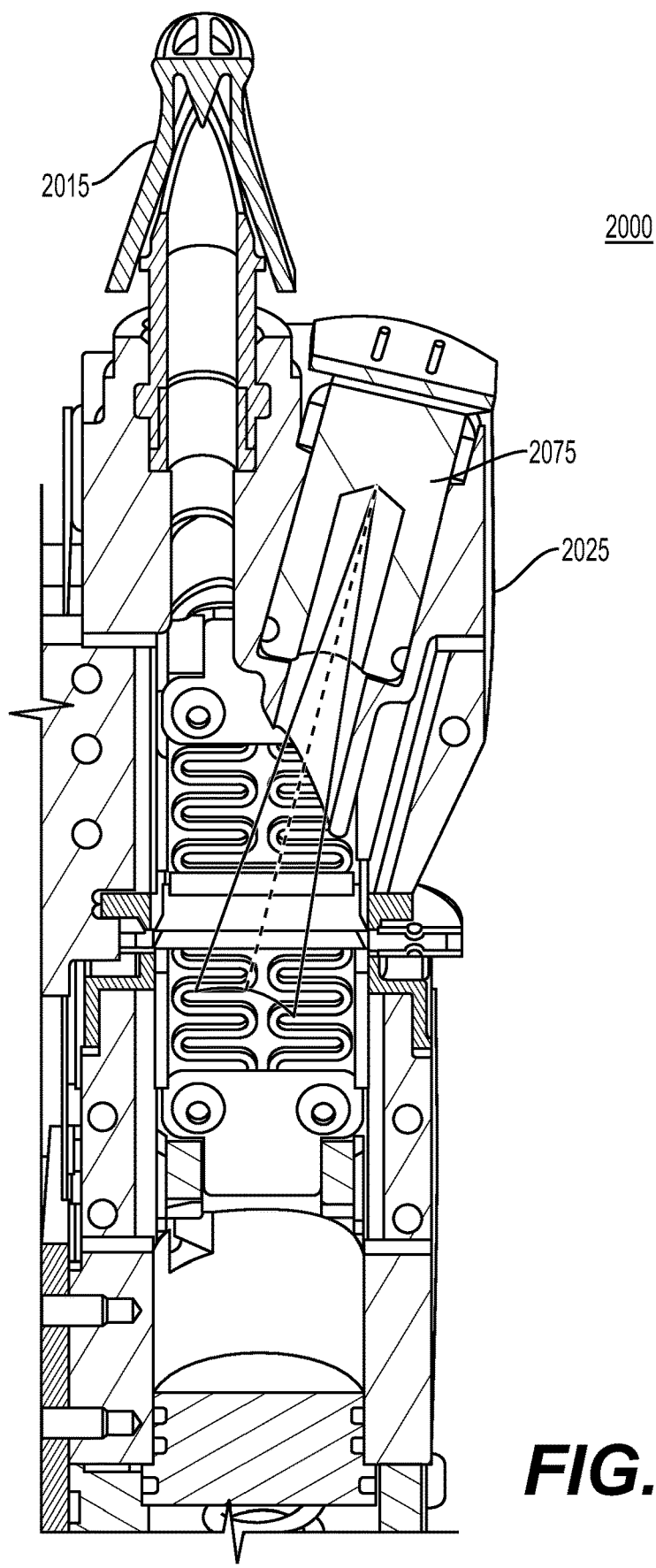
FIG. 28 is a cross-sectional view of another heat-not-burn aerosol-generating device according to an example embodiment.

FIG. 28 is a cross-sectional view of another heat-not-burn aerosol-generating device according to an example embodiment. Referring to FIG. 28, a heat-not-burn aerosol-generating device 2000 may include, inter alia, a mouthpiece 2015 and a device body 2025. It should be understood that the features in connection with the heat-not-burn aerosol-generating device 1000 of FIG. 27 may also be applicable to the heat-not-burn aerosol-generating device 2000 and will not be repeated in the interest of brevity. As shown in FIG. 28, a sensor 2075 may be included to measure a temperature of a capsule within the heat-not-burn aerosol-generating device 2000. For instance, the sensor 2075 may be an infrared (IR) sensor configured to perform contactless temperature sensing of a capsule. The sensor 2075 may be disposed so as to be downstream from and above a capsule within the device body 2025. In addition, the sensor 2075 may be offset from the aerosol path and oriented at an angle relative to the longitudinal axis of the heat-not-burn aerosol-generating device 2000. In an example embodiment, the longitudinal axis may be orthogonal to a plane corresponding to a face of the capsule, and the angle may be 8-20 degrees (e.g., 13-15 degrees) relative to the longitudinal axis. As a result, buildup and deposits from the generated aerosol may be reduced or prevented, thereby enhancing the performance and longevity of the sensor 2075.

Figure 29:
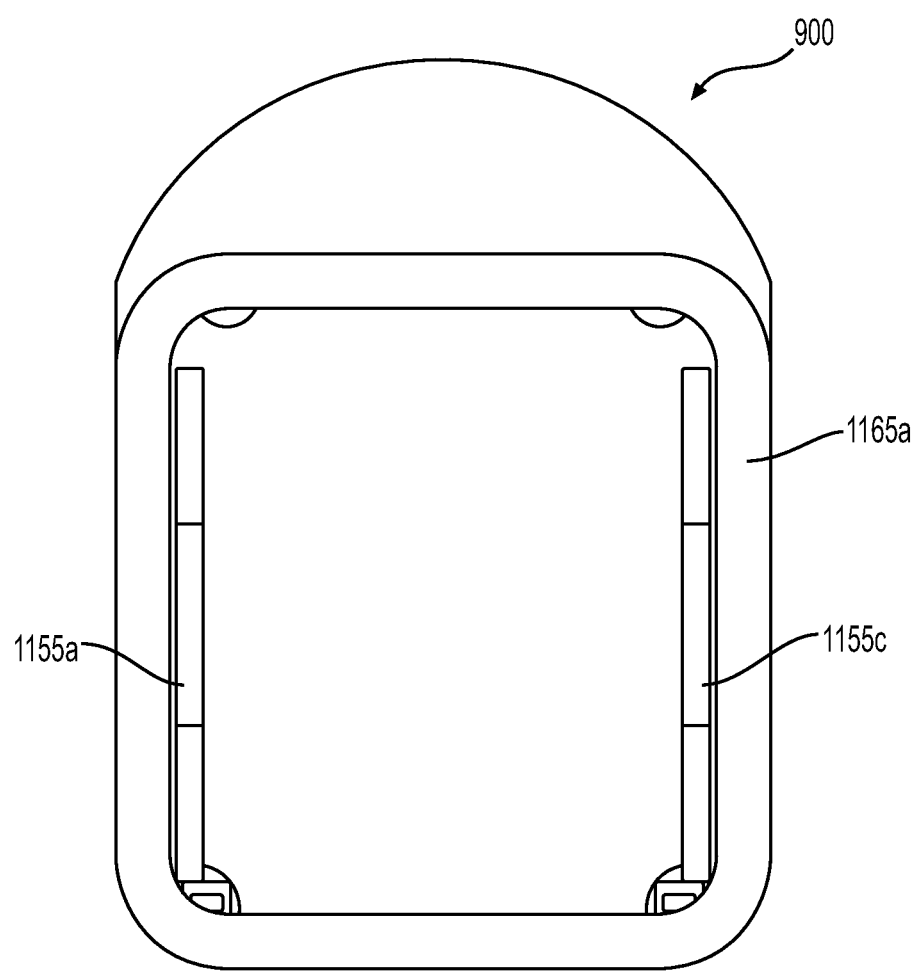
FIG. 29 is a plan view of an arrangement including a capsule engaged by electrodes and seals of a heat-not-burn aerosol-generating device according to an example embodiment.
Figure 30:
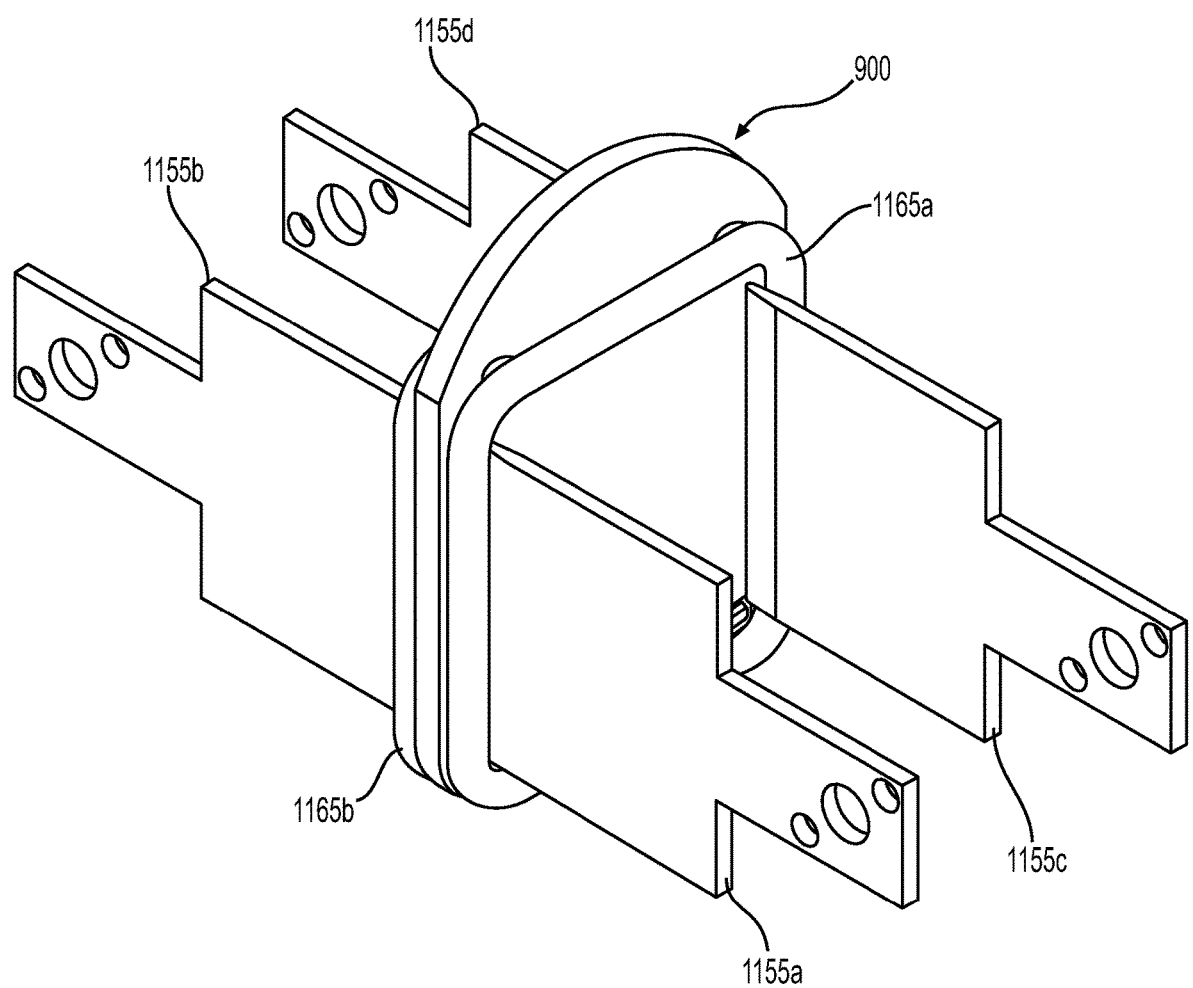
FIG. 30 is a perspective view of the arrangement of FIG. 29.
Figure 31:
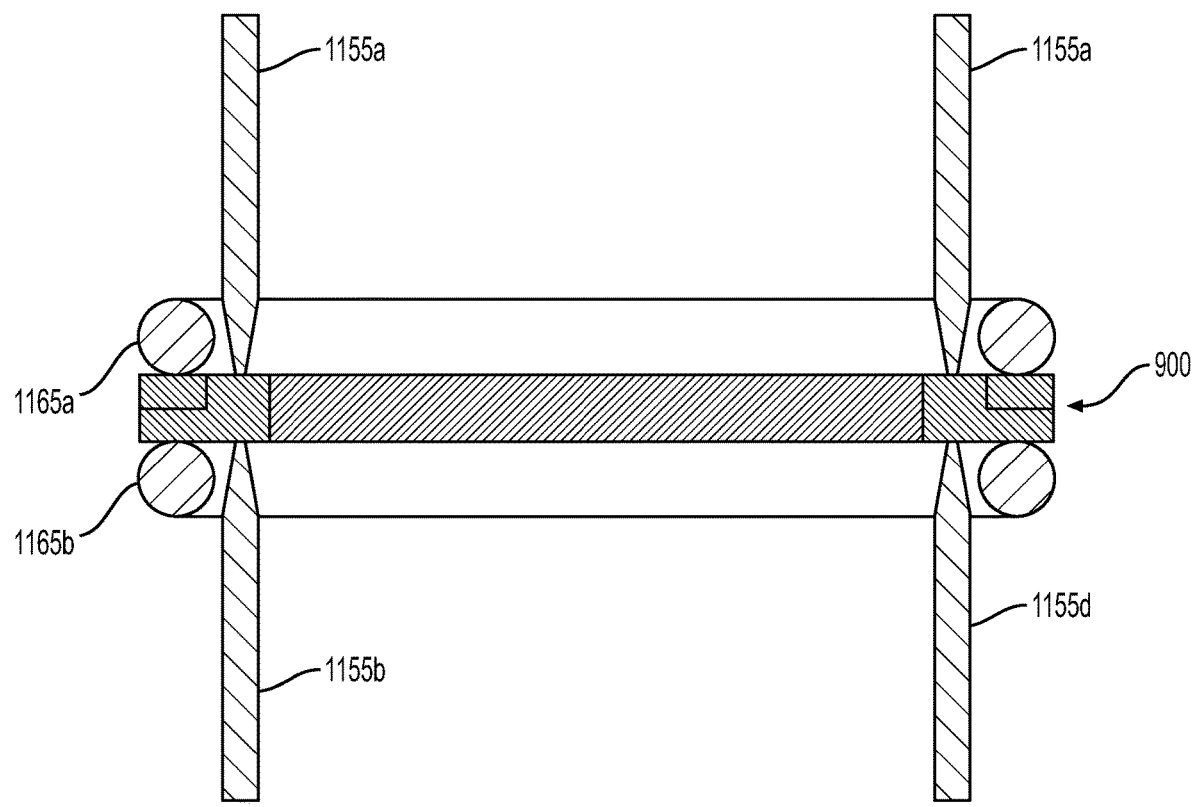
FIG. 31 is a side cross-sectional view of the arrangement of FIG. 29.

FIG. 29 is a plan view of an arrangement including a capsule engaged by electrodes and seals of a heat-not-burn aerosol-generating device according to an example embodiment. FIG. 30 is a perspective view of the arrangement of FIG. 29. FIG. 31 is a side cross-sectional view of the arrangement of FIG. 29. Referring to FIGS. 29-31, a capsule 900 within a heat-not-burn aerosol-generating device may be engaged by a first seal 1165a and a second seal 1165b. The first seal 1165a may be engaged with a side of the capsule 900 corresponding to a first heater, while the second seal 1165b may be engaged with a side of the capsule 900 corresponding to a second heater (or vice versa). When engaged, the first seal 1165a and the second seal 1165b may be on a periphery of the cavity so as to surround the heat-not-burn aerosol-forming substrate disposed therein.

A first electrode 1155a, a second electrode 1155b, a third electrode 1155c, and a fourth electrode 1155d are configured to electrically contact the capsule 900. According to at least some example embodiments, then the first electrode 1155a and the third electrode 1155c may electrically contact the first heater, while the second electrode 1155b and the fourth electrode 1155d may electrically contact the second heater. However, in non-limiting embodiments involving a capsule with only one heater, it should be understood that the first electrode 1155a and the third electrode 1155c (or the second electrode 1155b and the fourth electrode 1155d) may be omitted.

When engaged with the heaters, the first electrode 1155a and the third electrode 1155c are within the area bounded by the first seal 1165a, while the second electrode 1155b and the fourth electrode 1155d are within the area bounded by the second seal 1165b. The first electrode 1155a and the third electrode 1155c may also adjacent to opposite sides of the first seal 1165a such that the first heater is pressed against the underlying first frame. Similarly, the second electrode 1155b and the fourth electrode 1155d may be adjacent to opposite sides of the second seal 1165b such that the second heater is pressed against the underlying second frame. In example embodiments involving a third frame, the heaters may be pressed against the underlying third frame by the electrodes.

The first electrode 1155a, the second electrode 1155b, the third electrode 1155c, and the fourth electrode 1155d may be in the form of blades. Additionally, to reduce contact resistance, the first electrode 1155a, the second electrode 1155b, the third electrode 1155c, and the fourth electrode 1155d may be formed of steel and coated with titanium nitride. In an example embodiment, the blades may be straight-edged. Alternatively, the blades may be serrated to enhance an electrical contact in instances where the heaters have an uneven surface (e.g., heaters in the form of a mesh).

According to at least some example embodiments, the first electrode 1155a, second electrode 1155b, third electrode 1155c, fourth electrode 1155d, capsule 900, first seal 1165a and second seal 1165d may be included in the heat-not-burn aerosol-generating device 1000. For example, according to at least some example embodiments, the first electrode 1155a, second electrode 1155b, third electrode 1155c, fourth electrode 1155d and capsule 900 are examples of the first electrode 1055a, second electrode 1055b, third electrode 1055c, fourth electrode 1055d and capsule 800.

According to at least some example embodiments, the control circuitry 1045 and power source 1035 of the heat-not-burn aerosol-generating device 1000 are embodied, respectively, by the device system 2100 and power supply 2110 discussed above with reference to FIGS. 21A-23. Further, according to at least some example embodiments, the capsule 800 includes control circuitry, and the control circuitry of the capsule 800 is embodied by the pod system 2200 discussed above with reference to FIGS. 21A-23.

Examples of a heating engine control algorithm according to at least some example embodiments will be discussed in greater detail below with reference to FIGS. 24-25G.

Heating Engine Control Algorithms Overview

First, an overview of a heating engine control algorithm 2300 and related inputs will be explained with reference to FIG. 24. Next, example implementations of the heating engine control algorithm 2300 according to at least some example embodiments will be explained with reference to FIGS. 25A-26. Example implementations of the heating engine control algorithm 2300 include, but are not limited to, a setpoint heating engine control algorithm 2300A (FIGS. 25A-25B), an adaptive heating engine control algorithm 2300B (FIGS. 25C-25D), a temperature heating engine control algorithm 2300C (FIGS. 25E-25F), and a waveform heating engine control algorithm 2300D (FIGS. 25G-25H). Further, an example implementation of a buttonless vaping function 2310, which may provide a vaping mode as input to one or more of the heating engine control algorithms, 2300, 2300A, 2300B, 2300C, and 2300D, will be discussed below with reference to FIG. 26. For the purpose of simplicity, the algorithms of FIGS. 24-26 will be described below with reference, primarily, to the device system 2100 and pod system 2200 of the non-nicotine e-vapor device 500. However, as is discussed above, the heat-not-burn aerosol-generating devices 1000 and 2000 may also include the device system 2100 and pod system 2200. Consequently, details of the algorithms of FIGS. 24-26 described below with reference to a non-nicotine e-vapor device (e.g., the non-nicotine e-vapor device 500), or elements thereof, may also apply to the heat-not-burn aerosol-generating devices 1000 and 2000, or elements thereof. Further, details of the algorithms of FIGS. 24-26 described below with reference to a non-nicotine vapor or non-nicotine pre-vapor formulation may also apply to an aerosol or aerosol-forming substrate, respectively.

Referring to FIG. 24, FIG. 24 is a diagram illustrating the heating engine control algorithm 2300 and related inputs according to at least one example embodiment. Referring to FIG. 24, according to at least some example embodiments, the heating engine control algorithm 2300 generates a power level value and a heating engine driver 2305 controls the power supplied to the heating engine 2215 (e.g., using pulse width modulation (PWM) or another known method) based on the generated power level. For example, the heating engine driver 2305 may control an amount of power supplied to the heater engine 2215 via the body electrical/data interface 2210. According to at least some example embodiments, the heating engine control algorithm 2300 and heating engine driver 2305 are both implemented by the controller 2105 of the device system 2100 included in a non-nicotine e-vapor device (e.g., non-nicotine e-vapor device 500). Thus, any or all operations described in the present specification as being performed by any of heating engine control algorithm 2300 or the heating engine driver 2305 may be performed by the controller 2105.

As is illustrated in FIG. 24, the heating engine control algorithm 2300 may use one or more of a plurality of inputs to generate the power level supplied to the heating engine driver 2305. According to at least some example embodiments, inputs to the heating engine control algorithm 2300 may include, but are not necessarily limited to, a vaping mode generated by a buttonless vaping function 2310, one or more operating points generated by a first calibration mapping function 2320, a predicted temperature of the heating engine 2215 generated by a heating engine temperature prediction function 2330, heating engine temperature and electrical performance values provided by heating engine sensors 2222 (which may be included in the pod sensors 2220), airflow rate and wick wetness values provided by the pod sensors 2220, vaping profile information provided by an adult vaper vaping profile update function 2340, non-nicotine e-vapor device temperature information provided by device sensors 2125, non-nicotine pre-vapor formulation material level and/or flow rate information provided by a liquid level and flow rate prediction function 2350, battery health information provided by a battery health function 2360, and time information provided by a clock 2370. Pod sensors 2220 may also be referred to, herein, as smart pod sensors 2220. According to at least some example embodiments, the heating engine control algorithm operates in accordance with at least the following 3 states: an OFF state, a PREHEAT state, and an ON state. The OFF, PREHEAT, and ON states may also be referred to, herein, as "vaping mode states" or "operation modes."

According to at least some example embodiments, the OFF state is a state in which the heating engine control algorithm 2300 controls the heating engine driver 2305 such that a relatively low amount of power or, alternatively, no power is supplied to the heater engine 2215 by the non-nicotine e-vapor device 500; the PREHEAT state is a state in which the heating engine control algorithm 2300 controls the heating engine driver 2305 such that an amount of power supplied to the heater engine 2215 by the non-nicotine e-vapor device 500 is higher than the amount of power supplied in the OFF state; and the ON state is a state in which the heating engine control algorithm 2300 controls the heating engine driver 2305 such that an amount of power supplied to the heater engine 2215 by the non-nicotine e-vapor device 500 is higher than the amount of power supplied in the PREHEAT state. According to at least some example embodiments, the amount of power supplied to the heater engine 2215 during the PREHEAT operation mode is an amount that causes the heater engine 2215 to heat a non-nicotine pre-vapor formulation stored in the non-nicotine e-vapor device 500 to a temperature below a boiling point of the non-nicotine pre-vapor formulation (or an aerosol-generating temperature of the aerosol-forming substrate of the capsule 800), and the amount of power supplied to the heater engine 2215 during the second operation mode is an amount that causes the heater to heat the non-nicotine pre-vapor formulation stored in the non-nicotine e-vapor device 500 to a temperature equal to, or greater than, the boiling point of the non-nicotine pre-vapor formulation (or an aerosol-generating temperature of the aerosol-forming substrate of the capsule 800).

The setpoint heating engine control algorithm 2300A and buttonless vaping function 2310 will now be discussed below with reference to FIGS. 25A, 25B and 26.

Example Setpoint Heating Engine Control Algorithm

Figure 25A:
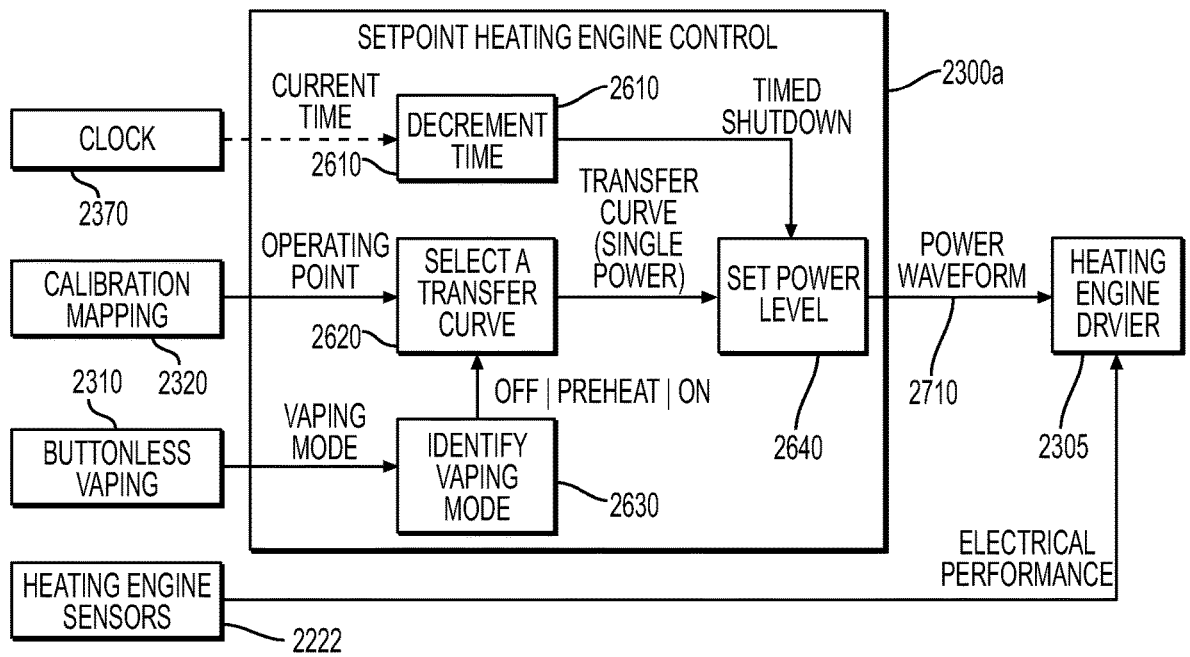
FIG. 25A is a block diagram illustrating a setpoint heating engine control algorithm according to at least some example embodiments.

FIG. 25A is a block diagram illustrating the setpoint heating engine control algorithm 2300A according to at least some example embodiments. According to at least some example embodiments, the setpoint heating engine control algorithm 2300A is an example implementation of the heating engine control algorithm 2300 illustrated in FIG. 24.

According to at least some example embodiments, the setpoint heating engine control algorithm 2300A is implemented by the controller 2105 of the device system 2100 included in a non-nicotine e-vapor device (e.g., non-nicotine e-vapor device 500). Thus, any or all operations described herein as being performed by the setpoint heating engine control algorithm 2300A (or, an element thereof) may be performed by the controller 2105.

According to at least some example embodiments, in the setpoint heating engine control algorithm 2300A, a set power level is directly provisioned based on an external configuration. According to at least some example embodiments, the power level applied to the heating engine 2215 (e.g., via the heating engine driver 2305) is static throughout the activation period of the heating engine 2215 or, alternatively, throughout the duration of a vaping mode. According to at least some example embodiments, a single power level is sent to the heating engine driver 2305, and an amount of power applied to the heating engine 2215 by the heating engine driver 2305 is proportional to the power level sent to the heating engine driver 2305. According to at least some example embodiments, the heating engine driver 2305 may set the level of the power output to the heating engine 2215 (e.g., by adjusting a duty cycle of a pulse width modulated driving signal applied to the heating engine 2215) immediately upon receiving the single power level.

Referring to FIG. 25A, the setpoint heating engine control algorithm 2300A may operate based on input received from the clock 2370, the heating engine sensors 2222 (which may be included in the smart pod sensors 2220), the buttonless vaping function 2310, and the first calibration mapping function 2320. Further, according to at least some example embodiments, the first calibration mapping function 2320 may operate based on input received from the AV vaping profile update function 2340.

The clock 2370, heating engine sensors 2222, buttonless vaping function 2310, first calibration mapping function 2320, and AV vaping profile update function 2340 will now be discussed in greater detail below.

The clock 2370 outputs a periodic timing signal in accordance with known methods. The heating engine sensors 2222 detect heating engine temperature values and/or electrical performance values associated with the heating engine 2215 in accordance with known methods. According to at least some example embodiments, the heating engine sensors provide the detected heating engine temperature values and/or electrical performance values to the heating engine driver 2305, for example, as feedback values. According to at least some example embodiments, the heating engine driver 2305 adjusts an amount of power being provided to the heating engine 2215 based on the feedback values. The buttonless vaping function 2310 will now be discussed below with reference to FIG. 26.

According to at least some example embodiments, the buttonless vaping function 2310 outputs, to the setpoint heating engine control algorithm 2300A, as the current vaping mode state, one of three states: the OFF state, the PREHEAT state, and the ON state. FIG. 26 is a flow chart illustrating the buttonless vaping function 2310 according to at least some example embodiments. The buttonless vaping function 2310 may be implemented by the controller 2105. Thus, any or all operations described herein as being performed by the buttonless vaping function 2310 may be performed by the controller 2105 of the device system 2100 included in a non-nicotine e-vapor device (e.g., non-nicotine e-vapor device 500).

Figure 26:
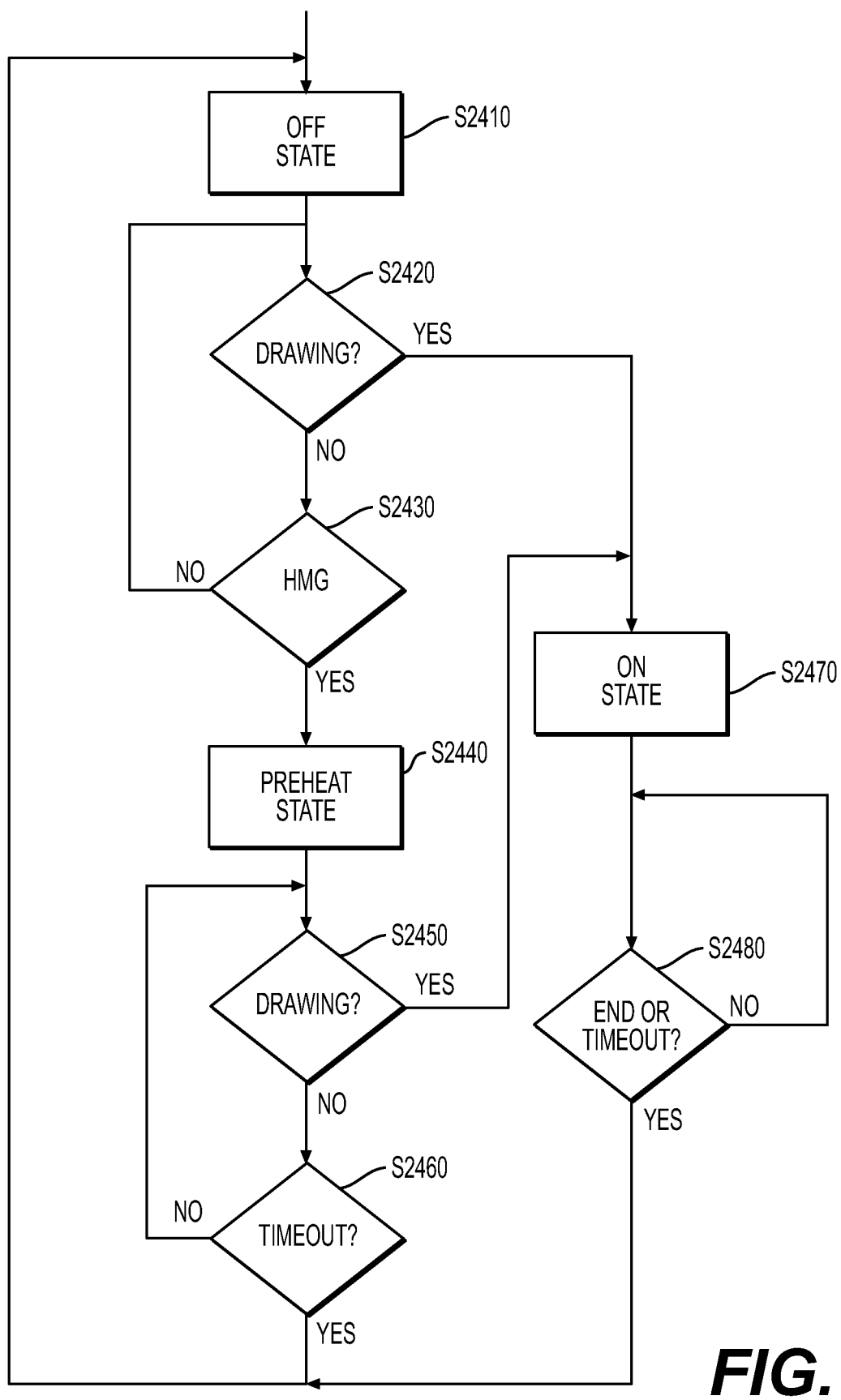
FIG. 26 is a flow chart illustrating the buttonless vaping function 2310 according to at least some example embodiments.

Referring to FIG. 26, initially, the buttonless vaping function 2310 outputs the OFF state. For example, in operation 52410, the buttonless vaping function 2310 outputs the OFF state as the current vaping mode state.

According to at least one example embodiment, the buttonless vaping function 2310 transitions the current vaping mode state from the OFF state to the ON state based on detecting vapor drawing during the OFF state. For example, in operation S2420, the buttonless vaping function 2310 determines whether or not vapor drawing is occurring. For example, the buttonless vaping function 2310 can determine whether or not a vapor drawing instance is occurring based on air flow information generated by the pod sensors 2220 and/or the device sensors 2124. For example, if the airflow information indicates an amount of airflow that is above a threshold value, the buttonless vaping function 2310 determines that a vapor drawing instance is occurring. If vapor drawing occurs during the OFF state, the buttonless vaping function 2310 proceeds to operation 52470. In operation 52470, the buttonless vaping function 2310 transitions the current vaping mode state from the OFF state to the ON state, and outputs the ON state as the current vaping mode state.

According to at least one example embodiment, the buttonless vaping function 2310 transitions the current vaping mode state from the OFF state to the PREHEAT state based on detecting a hand-to-mouth (HMG) gesture during the OFF state. An HMG is a gesture in which an adult vaper's hand moves towards the adult vaper's mouth. An HMG made with respect to a non-nicotine e-vapor device (e.g., the non-nicotine e-vapor device 500 and/or a non-nicotine e-vapor device including device body 100 or dispensing body) may indicate that vapor drawing may begin soon. Example methods of detecting an HMG are discussed in US Patent Application Publication Number 2017/0108840, the contents of which are incorporated, herein, by reference.

Returning to operation S2420, according to at least some example embodiments, if vapor drawing has not occurred during the OFF state, the buttonless vaping function 2310 proceeds to operation 52430. In operation 52430, the buttonless vaping function 2310 determines whether or not a HMG has occurred. If a HMG occurs during the OFF state, the buttonless vaping function 2310 proceeds to operation 52440. In operation 52440, the buttonless vaping function 2310 transitions the current vaping mode state from the OFF state to the PREHEAT state, and outputs the PREHEAT state as the current vaping mode state. According to at least some example embodiments, the buttonless vaping function 2310 maintains the OFF state as the current vaping mode state until the buttonless vaping function 2310 detects one of vapor drawing or a HMG. For example, returning to operation 52430, if a HMG has not occurred during the OFF state, the buttonless vaping function 2310 maintains the OFF state as the current vaping mode state and returns to operation S2420.

Returning to operation 52440, according to at least one example embodiment, the buttonless vaping function 2310 transitions the current vaping mode state from the PREHEAT state to the ON state based on detecting vapor drawing during the PREHEAT state. For example, the buttonless vaping function 2310 proceeds from operation 52440 to operation S2450. In operation S2450, the buttonless vaping function 2310 determines whether or not vapor drawing is occurring. If vapor drawing occurs during the PREHEAT state, the buttonless vaping function 2310 proceeds to operation 52470, thereby transitioning from the PREHEAT state to the ON state. As is discussed above, in operation 52470, the buttonless vaping function 2310 outputs the ON state as the current vaping mode state.

According to at least one example embodiment, the buttonless vaping function 2310 transitions from the PREHEAT state to the OFF state based on the occurrence of a preheat timeout event during the PREHEAT state. For example, in operation S2450, if vapor drawing has not occurred during the PREHEAT state, the buttonless vaping function 2310 proceeds to operation S2460. In operation S2460, the buttonless vaping function 2310 determines whether or not a preheat timeout event has occurred. The buttonless vaping function 2310 determines that a preheat timeout event has occurred when the buttonless vaping function 2310 determines that an amount of time spent in the PREHEAT state exceeds a preheat timeout value. If the buttonless vaping function 2310 determines a preheat timeout event has occurred during the PREHEAT state, the buttonless vaping function 2310 proceeds to operation 52410, thereby transitioning the current vaping mode state from the PREHEAT state to the OFF state. As is discussed above, in operation 52410, the buttonless vaping function 2310 outputs the OFF state as the current vaping mode state.

According to at least some example embodiments, the buttonless vaping function 2310 maintains the PREHEAT state as the current vaping mode state until the buttonless vaping function 2310 detects one of vapor drawing and a preheat timeout. For example, retuning to operation S2460, if, during the PREHEAT state, a preheat timeout event has not occurred and a vapor drawing instance has not been detected, the buttonless vaping function 2310 maintains the PREHEAT state and returns to operation S2450.

Returning to operation 52470, according to at least one example embodiment, the buttonless vaping function 2310 transitions from the ON state to the OFF state based on detecting a vapor drawing instance ending or a vaping timeout event. For example, the buttonless vaping function 2310 proceeds from operation 52470 to operation S2480. In operation S2480, the buttonless vaping function 2310 determines whether a vapor drawing instance has ended or whether a vaping timeout event has occurred. For example, based on airflow information generated by the pod sensors 2220 and/or the device sensors 2124, the buttonless vaping function 2310 can determine whether or not a vapor drawing instance detected in step S2420 or step S2450 has ended. For example, if, after vapor drawing is detected, the airflow information indicates that the airflow has fallen below a threshold value, the buttonless vaping function 2310 determines that a vapor drawing instance has ended. According to at least some example embodiments, the threshold used to detect the beginning of a vapor drawing instance in operation S2420 or S2450 may have a different value than the threshold used to detect the end of the vapor drawing instance in operation S2480.

Further, the buttonless vaping function 2310 determines that a vaping timeout event has occurred when the buttonless vaping function 2310 determines that an amount of time spent in the ON state exceeds a vaping timeout value. If the buttonless vaping function 2310 detects either the end of a vapor drawing instance or an occurrence of a vaping timeout event during the ON state, the buttonless vaping function 2310 proceeds to operation 52410, thereby transitioning the current vaping mode state from the ON state to the OFF state. According to at least some example embodiments, the buttonless vaping function 2310 maintains the ON state as the current vaping mode state until the buttonless vaping function 2310 detects one of the end of a vapor drawing instance and a vaping timeout event. For example, retuning to operation S2480, if a vaping timeout event has not occurred during the ON state, and an end to a current vapor drawing instance has not been detected, the buttonless vaping function 2310 maintains the ON state and repeats operation S2480.

According to at least some example embodiments, the buttonless vaping function 2310 may determine whether a preheat timeout event has occurred in operation S2460 and/or determine whether a preheat timeout event has occurred in operation S2480 based on timer values including a preheat timeout value and/or a vaping timeout value. For example, the buttonless vaping function 2310 may determine that the preheat timeout event has occurred in operation S2460 of FIG. 26 when the buttonless vaping function 2310 detects a PREHEAT vaping state length that exceeds the preheat timeout value. The preheat timeout value may be, for example, 1-2 seconds. Further, the buttonless vaping function 2310 may determine that the vaping timeout event has occurred in operation S2480 of FIG. 26 when the buttonless vaping function 2310 detects an ON vaping state length that exceeds the vaping timeout value. The vaping timeout value may be, for example, 7-10 seconds. According to at least some example embodiments, the buttonless vaping function 2310 can track the lengths of continuous ON or PREHEAT vaping states using the clock signal output by the clock 2370. Further, the preheat timeout and vaping timeout values are not limited to the example time lengths discussed above. For example, time lengths of the preheat timeout value and/or vaping timeout value may be set, for example, in accordance with the preferences of a designer or manufacturer of the non-nicotine e-vapor device 500.

Further, though the buttonless vaping function 2310 is described above as determining a current vaping mode state to be one of three states (i.e., OFF, PREHEAT and ON), according to at least some example embodiments, the PREHEAT state may be omitted, and the buttonless vaping function 2310 may determine the current vaping mode state to be one of only two states: ON and OFF. For example, referring to FIG. 26, when the PREHEAT state is omitted, the buttonless vaping function 2310 may omit operations S2430, S2440, S2450 and S2460. Further, when the PREHEAT state is omitted, the buttonless vaping function 2310 may perform operation S2420 without transitioning to the PREHEAT state. For example, the buttonless vaping function may perform operation S2420 by maintaining the OFF state while vapor drawing is not detected (N) and proceeding to operation S2470 in response to vapor drawing being detected (Y), thereby transitioning the current vaping mode state from the OFF state to the ON state. Additionally, when the PREHEAT state is omitted, the buttonless vaping function 2310 may perform the remaining operations S2410, S2470 and S2480 in the same manners discussed above with reference to FIG. 26. According to at least some example embodiments, the buttonless vaping function 2310 determines a current vaping mode state continuously and outputs the determined current vaping mode continuously, in accordance with the operations discussed above with respect to FIG. 26. The first calibration mapping function 2320 will now be discussed below.

The first calibration mapping function 2320 outputs operating points to the setpoint heating engine control algorithm 2300A. According to at least some example embodiments, the operating points correspond to power values or power levels, examples of which include, but are not limited to, 1 W, 2.567 W, 20 W, 32.15 W, and 52,663 W.

According to at least some example embodiments, the first calibration mapping function 2320 reads one or more operating points from a removable pod installed in a non-nicotine e-vapor device, and outputs one of the one or more operating points to the setpoint heating engine control algorithm 2300A. For example, a non-nicotine e-vapor device (e.g., non-nicotine e-vapor device 500) implementing the first calibration mapping function 2320 may be configured to detect power information from removable pod 300 installed in the non-nicotine e-vapor device 500. The power information read from the pod 300 may include one or more operating points. For example, according to at least some example embodiments, the power information read from the pod 300 may include an operating point for each vaping mode state (i.e., PREHEAT, ON and OFF). According to at least some example embodiments, the power information read from the pod 300 may include an operating points for the PREHEAT and ON states, and not the OFF state.

According to at least some example embodiments, the first calibration mapping function 2320 reads a plurality of operating points from the removable pod; receives a coarse preference level from the AV vaping profile update function 2340; selects the operating point or operating points, from among the read operating points, that correspond to the coarse preference level; and outputs the selected operating point or points to the setpoint heating engine control algorithm 2300A. For example, according to at least some example embodiments, the power information read from the pod 300 by the first calibration mapping function 2320 may include an operating point for each possible combination of coarse preference level and vaping mode state (PREHEAT, ON and OFF). According to at least some example embodiments, the power information read from the pod 300 may include an operating point for each coarse preference level with respect to the ON state, include only one operating point for the PREHEAT state, and include only one operating point (or, alternatively, no operating points) for the OFF state.

According to at least some example embodiments, the first calibration mapping function 2320 reads an operating point from the removable pod; receives a fine preference level from the AV vaping profile update function 2340; adjusts the read operating point based on the fine preference level; and outputs the adjusted operating point to the setpoint heating engine control algorithm 2300A. For example, the fine preference level received from the AV vaping profile update function 2340 may indicate an adjustment to be made to an operating point. For example, the fine preference level may indicate an adjustment direction and an adjustment amount (e.g., a sign and a magnitude: +3 W, −4.823 W, +10.645 W, etc.).

According to at least some example embodiments, the first calibration mapping function 2320 may generate an operating point based on both a coarse preference level and a fine preference level, each of which is received from the AV vaping profile update function 2340. For example, according to at least some example embodiments, the first calibration mapping function 2320 reads a plurality of operating points from the removable pod; receives a coarse preference level from the AV vaping profile update function 2340; selects the operating point, from among the read operating points, that corresponds to the coarse preference level; receives a fine preference level from the AV vaping profile update function 2340; adjusts the selected operating point based on the fine preference level; and outputs the adjusted operating point to the setpoint heating engine control algorithm 2300A.

According to at least some example embodiments, the first calibration mapping function 2320 is implemented by the controller 2105 of the device system 2100 included in a non-nicotine e-vapor device (e.g., non-nicotine e-vapor device 500). Thus, any or all operations described, herein, as being performed by first calibration mapping function 2320 may be performed, or controlled, by the controller 2105. The AV vaping profile update function 2340, coarse preference levels and fine preference levels will now be discussed in greater detail below.

According to at least some example embodiments, the AV vaping profile update function 2340 outputs one or both of the coarse preference level and fine preference level discussed above with reference to the first calibration mapping function 2320. An example of the AV vaping profile update function 2340 outputting a coarse preference level will now be discussed below.

According to at least one example embodiment, an adult vaper may manipulate an input device of the non-nicotine e-vapor device 500 to select one of a plurality of coarse preference levels. For example, as is noted above with reference to FIGS. 21A and 21B, the device body 100 of the non-nicotine e-vapor device 500 may include on-product controls 2150. According to at least some example embodiments, the on-product controls 2150 can include any device or devices capable of being manipulated manually by an adult vaper to indicate a selection of a value. Example implementations include, but are not limited to, one or more buttons, a dial, a capacitive sensor, and a slider. For example, when the on-product controls 2150 include a slider, the non-nicotine e-vapor device 500 may be capable of detecting a position of an adult vaper's finger along a length of the slider in accordance with known methods. For example, the slider may include a capacitive sensor that runs the length of the slider. Further, the non-nicotine e-vapor device 500 may be capable of detecting a location, along the length of the slider, of an adult vaper's finger touching the capacitive sensor based on signals generated by the capacitive sensor in accordance with known methods. As another example, the slider may include a mechanical element coupled to a track that runs the length of the slider. The mechanical element may be configured to be slid, by an adult vaper's finger, up and down the track. Further, the non-nicotine e-vapor device 500 may be capable of detecting a location of the mechanical element along the length of the slider.

According to at least some example embodiments, the length of the slider may be divided into a plurality of contiguous regions, and the plurality of coarse preference levels may be assigned to the plurality of contiguous regions, respectively. For example, in a scenario where 5 coarse preference levels are assigned to 5 contiguous regions of a length of the slider, respectively, the adult vaper can select a particular preference level, from among the 5 coarse preference levels, by manipulating the slider (e.g., by moving the adult vaper's finger and/or the mechanical element to a location along the length of the slider that is within the region to which the particular coarse preference level is assigned.). According to at least some example embodiments, the slider may be implemented as one or more capacitive touch sensors.

In addition to, or as an alternative to, including a slider, on-product controls 2150 may include one or more buttons that facilitate the selection of a particular preference level from among the coarse preference levels discussed above. For example, in the example illustrated in FIG. 1, the dispensing body includes first and second buttons 118 and 120. According to at least some example embodiments, the coarse preference levels (e.g., 5 coarse preference levels) may be cycled through by in response to manipulation of one or both of the first and second buttons 118 and 120. According to at least some example embodiments, the first and second buttons are implemented as touch sensors, which may be mechanical (e.g., mechanical buttons) and/or capacitive (e.g., capacitive sensors).

According to at least some example embodiments, the device body 100 may provide an indication (e.g., a visual, tactile and/or auditory indication) for identifying a presently selected coarse preference level from among a plurality of available coarse preference levels. For example, according to at least some example embodiments, the second button 120 is an intensity button, and manipulation of the second button 120 may cause the non-nicotine e-vapor device 500 to advance from a current coarse preference level to a next coarse preference level. Further, the light guide assembly illustrated in FIG. 1 may provide a different visual indication for each different coarse preference level (e.g., by changing a color, length, size and or brightness of light emitted by the light guide assembly), thereby identifying a presently selected coarse preference level.

Next, the AV vaping profile update function 2340 outputs the selected coarse preference level to the first calibration mapping function 2320. Further, the 5 coarse preference levels may correspond, respectively, to 5 operating points read by the first calibration mapping function 2320 from a removable pod (e.g., pod 300) installed in a non-nicotine e-vapor device 500. Accordingly, the first calibration mapping function 2320 outputs the operating point, from among the 5 operating points read from the removable pod, that corresponds to the received coarse preference level. An example of the AV vaping profile update function 2340 outputting a fine preference level will now be discussed below.

According to at least one example embodiment, an adult vaper may manipulate an input device to select one of a plurality of fine preference levels. According to at least some example embodiments, the input device may be a wireless electronic device (e.g., a wireless communication device) examples of which include, but are not limited to, a smart phone and a tablet. According to at least some example embodiments, the electronic device executes an application or app that an adult vaper can use to select a fine preference value for adjusting an operation point. According to at least some example embodiments, a non-nicotine e-vapor device (e.g., non-nicotine e-vapor device 500) and the wireless electronic device may communicate with each other, wirelessly (e.g., via a wireless communication link), using any known wireless technology, examples of which include, but are not limited to: Bluetooth, Wi-Fi, Wireless USB, Institute of Electrical and Electronics engineers (IEEE) 802.11, etc. For example, according to at least some example embodiments, the electronic device is a smart phone running an app that causes the smart phone to creates a graphic user interface (GUI) which an adult vaper can interact with in order to select a fine preference level. According to at least some example embodiments, the GUI includes an app slider. The app slider may be an image of a slider, output to a display of the smart phone, which an adult vaper can manipulate by using a touch screen, keys, buttons and/or other input devices of the smart phone. According to at least some example embodiments, the app slider enables an adult vaper to adjust an operating point (e.g. 7 W) in a fine or precise manner. For example, if an initial operating point is 7 W and the app slider allows an adult vaper to adjust the initial operating point in 1 mW increments within a range of ±128 mW, the adult vaper could choose an adjusted operating point between 6872 mW and 7128 mW. According to at least some example embodiments, the smart phone can send a fine preference level indicating the adjustment selected by the adult vaper through the app slider to the non-nicotine e-vapor device, wirelessly. At the non-nicotine e-vapor device, the AV vaping profile update function 2340 receives the fine preference level and provides the fine preference level to the first calibration mapping function 2320. As is noted above, the first calibration mapping function 2320 may use the fine preference level received from the AV vaping profile update function 2340 to an adjust an operating point before outputting the adjusted operating point to the setpoint heating engine control algorithm 2300A.

According to at least some example embodiments, the AV vaping profile update function 2340 writes coarse preference levels and/or fine preference levels selected by an adult vaper to memory (e.g., non-volatile memory 2205b) of a removable pod (e.g., removable pod 300) installed in a non-nicotine e-vapor device (e.g., non-nicotine e-vapor device 500). Accordingly, when a removable pod (e.g., pod 300) is reinstalled into the non-nicotine e-vapor device after having been removed for some time, the first calibration mapping function 2320 may read coarse preference levels and/or fine preference levels that were previously selected by the adult vaper from memory of the reinstalled removable pod. Further, the first calibration mapping function 2320 may use the previously selected coarse preference levels and/or fine preference levels to generate an adjusted operating point.

According to at least some example embodiments, the AV vaping profile update function 2340 writes vaping profile entries to a vaping profile data base. According to at least some example embodiments, the vaping profile database may be stored in a memory (e.g., storage medium 2145) of a dispensing body (e.g., device body 100) of a non-nicotine e-vapor device (e.g., non-nicotine e-vapor device 500). Each vaping profile entry may include a coarse preference level and/or fine preference level selected by an adult vaper along with formulation type information (e.g., a non-nicotine pre-vapor formulation identifier) that identifies a formulation type of non-nicotine pre-vapor formulation contained by the removable pod that was installed in the non-nicotine e-vapor device at the time the adult vaper selected the coarse preference level and/or fine preference level. Further, according to at least some example embodiments, when a new, unused removable pod is installed in the non-nicotine e-vapor device, the first calibration mapping function 2320 can read the non-nicotine pre-vapor formulation identifier of the new removable pod and compare the read non-nicotine pre-vapor formulation identifier to the vaping profile entries stored in the vaping profile database. When the first calibration mapping function 2320 identifies a vaping profile entry having a non-nicotine pre-vapor formulation identifier that matches the non-nicotine pre-vapor formulation identifier of the newly installed removable pod, the first calibration mapping function 2320 may read the coarse preference level and/or fine preference level included in the identified vaping profile entry. Further, the first calibration mapping function 2320 may use the read coarse preference level and/or fine preference level to generate an adjusted operating point. According to at least some example embodiments, the first calibration mapping function 2320 can read the identity (e.g., formulation type) of the non-nicotine pre-vapor formulation of a removable pod in the same manner discussed above with respect the first calibration mapping function 2320 reading operating points from an image (e.g., a QR code) located on a removable pod (e.g., pod 300) or memory of the removable pod.

According to at least some example embodiments, the AV vaping profile update function 2340 tracks coarse preference levels and/or fine preference levels selected by an adult vaper over time, and stores the tracked coarse preference levels and/or fine preference levels in a memory of the non-nicotine e-vapor device 500 (e.g., storage medium 2145 of the device body 100 of the non-nicotine e-vapor device 500). Further, the AV vaping profile update function 2340 can determine a predicted coarse preference level based on the tracked coarse preference levels and/or determine a predicted fine preference level based on the tracked fine preference levels. Predicted coarse preference levels and a predicted fine preference levels may also be referred to, herein, as predicted vaping preference levels.

According to at least some example embodiments, the predicted coarse preference value is a mean, median or mode of the tracked coarse preference levels. According to at least some example embodiments, the predicted coarse preference value is a mean, median or mode of the tracked coarse preference levels that fall within a window (e.g., the last 10 tracked coarse preference levels). According to at least some example embodiments, the predicted coarse preference value is a weighted average of the tracked coarse preference levels.

According to at least some example embodiments, the predicted fine preference value is a mean, median or mode of the tracked fine preference levels. According to at least some example embodiments, the predicted fine preference value is a mean, median or mode of the tracked fine preference levels that fall within a window (e.g., the last 10 tracked fine preference levels). According to at least some example embodiments, the predicted fine preference value is weighted average of the tracked fine preference levels.

According to at least some example embodiments, the AV vaping profile update function 2340 can calculate different predicted vaping preference values for different times of day. An example time of day is a time period within a day (e.g., 8 AM-12 PM; 12 PM-4 PM; etc.). Accordingly, the AV vaping profile update function 2340 can calculate a morning predicted coarse preference level based only on coarse preference levels tracked during the morning (e.g., 8 A-12 PM), and calculate an afternoon predicted coarse preference level based only on coarse preference levels tracked during the afternoon (e.g., 12 PM-4 PM). Further, the AV vaping profile update function 2340 can calculate a morning predicted fine preference level based only on fine preference levels tracked during the morning (e.g., 8 A-12 PM), and calculate an afternoon predicted fine preference level based only on fine preference levels tracked during the afternoon (e.g., 12 PM-4 PM). The AV vaping profile update function 2340 may store the above-referenced predicted vaping preference levels in a memory of the non-nicotine e-vapor device 500 (e.g., storage medium 2145 of the device body 100 of the non-nicotine e-vapor device 500). According to at least some example embodiments, upon activation of the non-nicotine e-vapor device 500, the first calibration mapping function 2320 may determine a current time (e.g., 2 PM); read the stored vaping preference levels corresponding to the current time (e.g., the afternoon coarse predicted preference value and the afternoon predicted coarse preference level) from the memory of the non-nicotine e-vapor device 500, and use the read vaping preference levels to generate an adjusted operating point.

Returning to FIG. 25A, the setpoint heating engine control algorithm 2300A may also include a decrement time operation 2610, a first transfer curve selection operation 2620, a vaping mode identification operation 2630, and a first power level setting operation 2640. According to at least some example embodiments, any or all of the decrement time operation 2610, first transfer curve selection operation 2620, vaping mode identification operation 2630, and first power level setting operation 2640 of the setpoint heating engine control algorithm 2300A may be performed continuously. The decrement time operation 2610 will now be discussed in greater detail below.

The decrement time operation 2610 decrements timer values based on a current time input from the clock 2370. As is discussed in greater detail below, the timer values may be used by other operations including, for example, the first power level setting operation 2640. The first transfer curve selection operation 2620 will now be discussed in greater detail below.

In the first transfer curve selection operation 2620, the setpoint heating engine control algorithm 2300A may select a transfer curve from among one or more transfer curves received from the first calibration mapping function 2320 and provide the selected transfer curve to the first power level setting operation 2640. According to at least some example embodiments, the transfer curve output by the first transfer curve selection operation may be one of a plurality of operating points output from the first calibration mapping function 2320 to the first transfer curve selection operation 2620.

For example, the first calibration mapping function 2320 may provide an operating point for each of a plurality of vaping mode states. For example, according to at least some example embodiments, the operating points provided to the setpoint heating engine control algorithm 2300A by the first calibration mapping function 2320 include two operating points: an operating point for the PREHEAT vaping mode state, and an operating point for the ON vaping mode state. However, alternatively, according to at least some example embodiments, the first calibration mapping function 2320 may provide, for one or both of the PREHEAT and ON vaping mode states a series of operating points which vary in level with respect to time, as will be discussed in greater detail below with reference to FIGS. 25G and 25H.

Returning to FIG. 25A, as is noted above, according to at least some example embodiments, the first calibration mapping function 2320 may output multiple operating points corresponding, respectively, to multiple vaping mode states. The first transfer curve selection operation 2620 may select one of the operating points output by the first calibration mapping function 2320 based on a current vaping mode of the setpoint heating engine control algorithm 2300A (e.g., OFF, PREHEAT, or ON). The first transfer curve selection operation 2620 may provide a transfer curve corresponding to selected operating point to the first power level setting operation 2640. For example, if the setpoint heating engine control algorithm 2300A is in the PREHEAT vaping mode state, the first transfer curve selection operation 2620 may provide the first power level setting operation 2640 with a transfer curve corresponding to the PREHEAT vaping mode state. Similarly, if the setpoint heating engine control algorithm 2300A is in the ON vaping mode state, the first transfer curve selection operation 2620 may provide the first power level setting operation 2640 with a transfer curve corresponding to the ON vaping mode state. Further, if the setpoint heating engine control algorithm 2300A is in the OFF vaping mode state, the first transfer curve selection operation 2620 may provide the first power level setting operation 2640 with a transfer curve corresponding to the OFF vaping mode state. If the selected transfer curve does not include a portion corresponding to the OFF vaping mode state, then, according to at least some example embodiments, the first transfer curve selection operation 2620 may provide the first power level setting operation 2640 with a default transfer curve that corresponds to providing a low level of power or no power to the heating engine 2215 for the OFF vaping mode state. According to at least some example embodiments, the first transfer curve selection operation 2620 chooses a transfer curve to provide to the first power level setting operation 2640 based on vaping mode state information received from the vaping mode identification operation 2630. The vaping mode identification operation 2630 will now be discussed in greater detail below. According to at least some example embodiments, the transfer curves provided by the first transfer curve selection operation 2620 may be, or correspond to, power values.

According to at least some example embodiments, the vaping mode identification operation 2630 determines a current vaping mode state of the setpoint heating engine control algorithm 2300A (e.g., OFF, PREHEAT, or ON) based on the current vaping mode state output of the buttonless vaping function 2310. According to at least some example embodiments, the buttonless vaping function 2310 outputs the current vaping mode state in the manner discussed above with reference to FIG. 26. As is noted above, the first transfer curve selection operation 2620 may use the vaping mode state received from the vaping mode identification operation 2630 to choose which transfer curve to provide to the first power level setting operation 2640. According to at least some example embodiments, the vaping mode identification operation 2630 may be omitted and the first transfer curve selection operation 2620 may receive the vaping mode state (e.g., OFF, PREHEAT, or ON) from the buttonless vaping function 2310. The first power level setting operation 2640 will now be discussed in greater detail below.

According to at least some example embodiments, the first power level setting operation 2640 receives a transfer curve from the first transfer curve selection operation 2620 and outputs a first power level waveform 2710 in accordance with the operating point or points included in the received transfer curve. The first power level setting operation 2640 may output the first power level waveform 2710 to the heating engine driver 2305, and the heating engine driver 2305 may cause the power supply 2110 to supply power to the heater engine 2215 in accordance with the first power level waveform 2710.

Figure 25B:
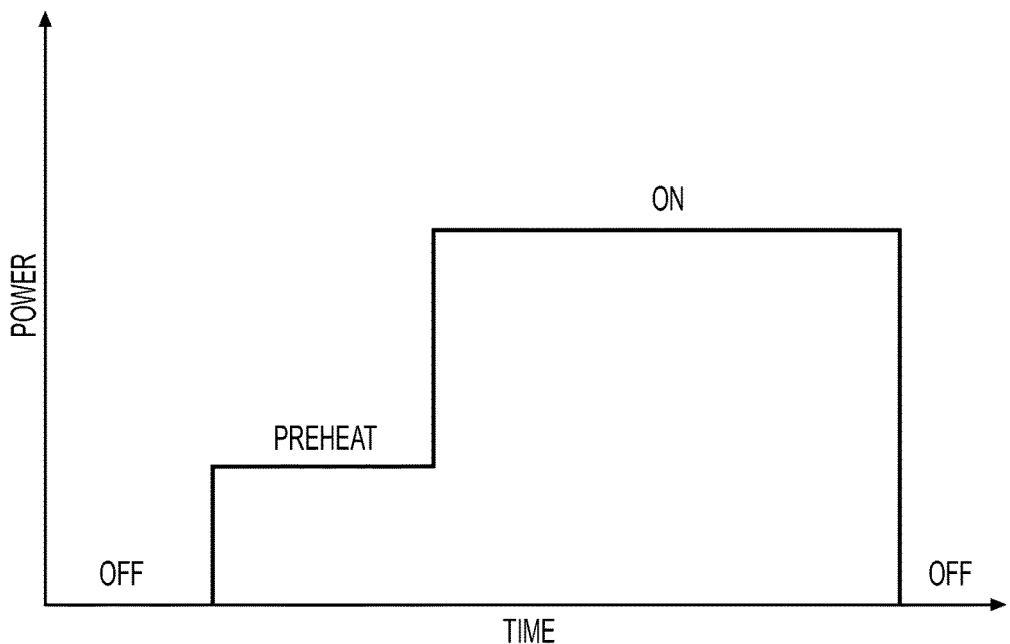
FIG. 25B illustrates an example of at least a portion of power level waveform generated by the setpoint heating engine control algorithm of FIG. 25A according to at least some example embodiments.

FIG. 25B illustrates an example of at least a portion of power level waveform output by the setpoint heating engine control algorithm 2300A. For example, FIG. 25B illustrates an example of at least a portion of a first power level waveform 2710 output by the first power level setting operation 2640 as a vaping mode state output from the buttonless vaping function 2310 and/or the vaping mode identification operation 2630 transitions in accordance with the following sequence, OFF→PREHEAT→ON→OFF. As used in the present specification, the term "power level waveform" refers to a waveform corresponding to power levels output by a heating engine control algorithm to the heating engine driver 2305 over time. Further, the term "power level waveform" may be considered to be synonymous with, and may be occasionally referred to as, a "power waveform." According to at least some example embodiments, the heating engine driver 2305 causes an amount of power provided to the heater 2215 by the power supply 2110 to increase or decrease in manner that is proportional to an increase or decrease in a magnitude of the power levels of a power level waveform output to the heating engine driver 2305.

As is illustrated in FIG. 25B, the first power level waveform 2710 output by the first power level setting operation 2640 may begin with a power level corresponding to the OFF vaping mode state (e.g., in response to the first transfer curve selection operation 2620 selecting the transfer curve corresponding to the OFF vaping mode state); rise from the power level corresponding to the OFF vaping mode state to a power level corresponding to the PREHEAT vaping mode state (e.g., in response to the first transfer curve selection operation 2620 selecting the transfer curve corresponding to the PREHEAT vaping mode state); rise from the power level corresponding to the PREHEAT vaping mode state to the power level corresponding to the ON vaping mode state (e.g., in response to the first transfer curve selection operation 2620 selecting the transfer curve corresponding to the ON vaping mode state); and fall from the power level corresponding to the ON vaping mode state back down to the power level corresponding to an OFF vaping mode state (e.g., in response to the first transfer curve selection operation 2620 selecting the transfer curve corresponding to the OFF vaping mode state).

As is illustrated in FIG. 25A, according to at least some example embodiments, the decrement time operation 2610 may cause the first power level setting operation 2640 to perform a shutdown operation with respect to the heating engine 2215 by sending a timer shutdown signal to the first power level setting operation 2640. The timer shutdown signal may also be referred to, herein, as a "timed shutdown signal." For example, according to at least some example embodiments, the decrement time operation 2610 may be used to implement a shutdown of the power provided to the heating engine 2215 by controlling the power level output by the first power level setting operation 2640. For example, in addition to, or instead of, the buttonless vaping function 2310 causing a shutdown of the power provided to the heating engine 2215 (e.g., by tracking a preheat timeout event and/or vaping timeout event, and outputting the OFF state as the current vaping mode state in the manner discussed above with reference to operations S2460 and S2480 of FIG. 26), the decrement time operation 2610 may track the preheat timeout value and/or the vaping timeout value against time lengths for which the current vaping mode state of the setpoint heating engine control algorithm 2300A is maintained as the PREHEAT state or the ON state. Further, in response to the decrement time operation 2610 determining that the preheat timeout value or the vaping timeout value has been exceeded, the decrement time operation 2610 sends a timer shutdown signal to the first power level setting operation 2640, and the first power level setting operation 2640 responds to the timer shutdown signal by outputting a power level or power level waveform to the heating engine driver 2305 that causes the heating engine driver 2305 to cut or cease the supply of power to the heating engine 2215. According to at least some example embodiments, in response to the first power level setting operation 2640 receiving the timer shutdown signal from the decrement time operation 2610, the first power level setting operation 2640 causes the heating engine driver 2305 to cut or cease the supply of power to the heating engine 2215 regardless of the transfer curve output by the first transfer curve selection operation 2620.

The adaptive heating engine control algorithm 2300B will now be discussed below with reference to FIGS. 25C and 25D.

Example Adaptive Heating Engine Control Algorithm

Figure 25C:
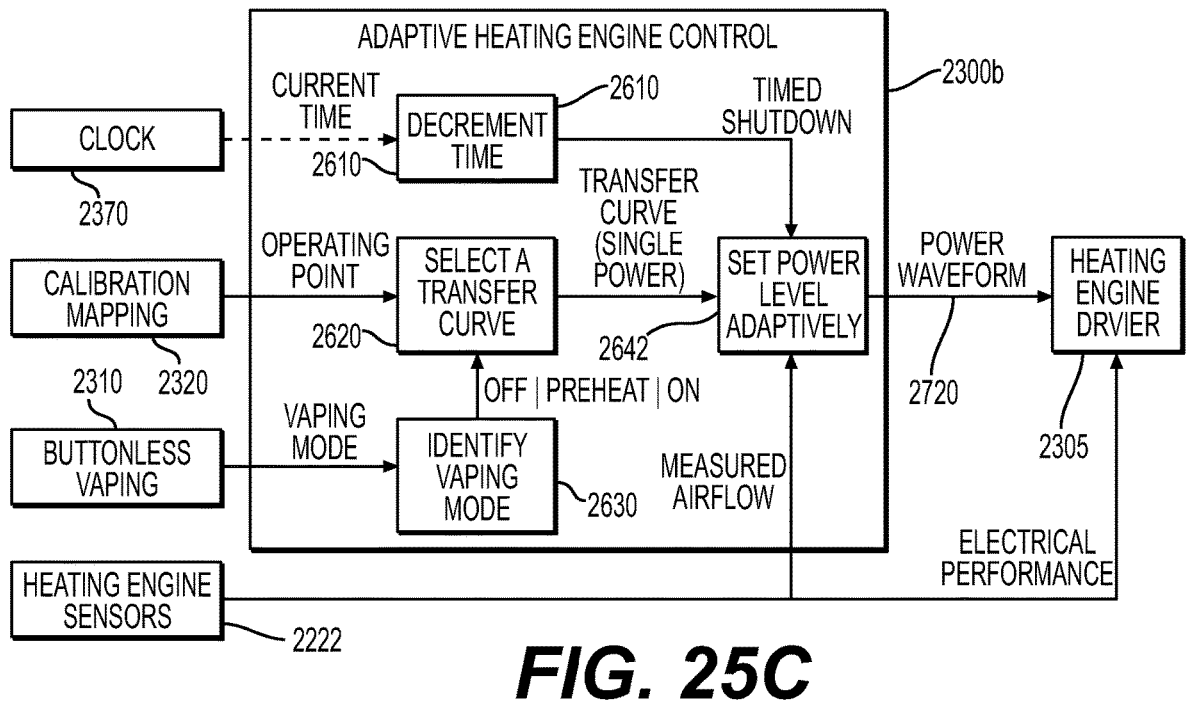
FIG. 25C is a block diagram illustrating an adaptive heating engine control algorithm according to at least some example embodiments.
Figure 25D:
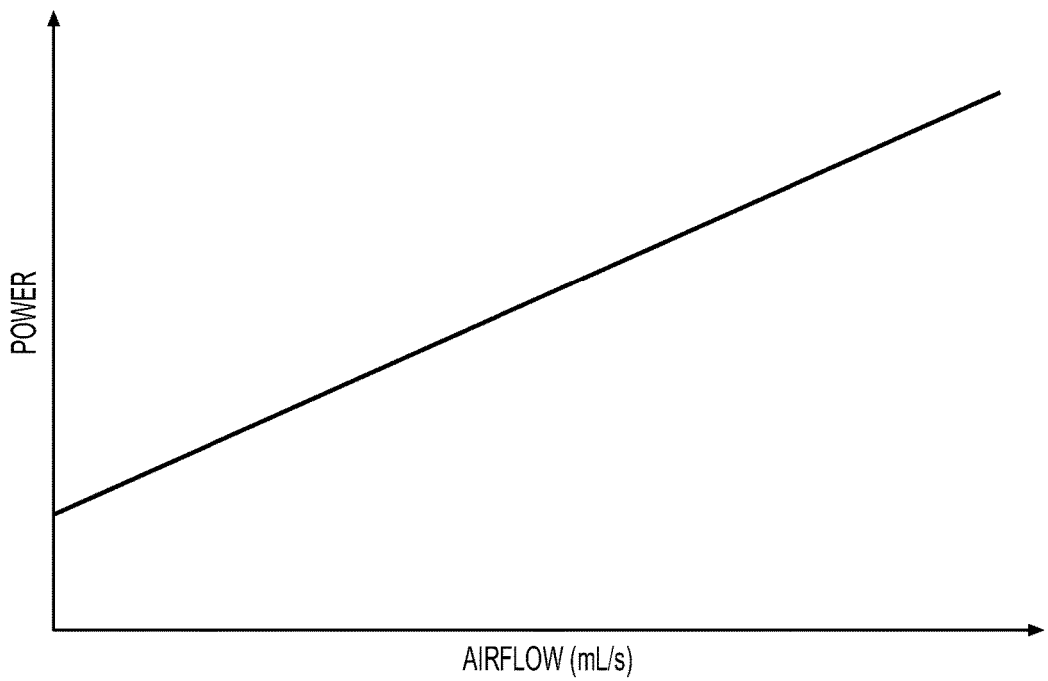
FIG. 25D illustrates an example relationship between detected airflow and an adapted power level generated by the adaptive heating engine control algorithm of FIG. 25C according to at least some example embodiments.

FIG. 25C is a block diagram illustrating the adaptive heating engine control algorithm 2300B according to at least some example embodiments. According to at least some example embodiments, the adaptive heating engine control algorithm 2300B is an example implementation of the heating engine control algorithm 2300 illustrated in FIG. 24.

According to at least some example embodiments, the adaptive heating engine control algorithm 2300B is implemented by the controller 2105 of the device system 2100 included in a non-nicotine e-vapor device (e.g., non-nicotine e-vapor device 500). Thus, any or all operations described herein as being performed by the adaptive heating engine control algorithm 2300B (or, an element thereof) may be performed by the controller 2105.

Referring to FIG. 25C, according to at least some example, during a vaping drawing instance, an amount of power applied to the heating engine 2215 by the adaptive heating engine control algorithm 2300B may correspond to a magnitude of measured airflow. The terms "airflow" and "airflow rate," as used in the present specification, refer to a rate at which air flows (i.e., a volume of air that passes per unit of time), and may be measured, for example, in terms of milliliters per second (mL/s).

According to at least some example embodiments, as is illustrated in FIG. 25C, the adaptive heating engine control algorithm 2300B may have the same structure as the setpoint heating engine control algorithm 2300A of FIG. 25A, with the exception that the first power level setting operation 2640 is replaced with an adaptive power level setting operation 2642. Relative to the first power level setting operation 2640, the adaptive power level setting operation 2642 may additionally receive airflow measurements from one or more sensors of the non-nicotine e-vapor device 500 (e.g., a hot-wire anemometer flow sensor included in heating engine sensors 2222, pod sensors 2220, or device sensors 2125). For example, heating engine sensors 2222 may repeatedly measure a rate of airflow with respect to air flowing through the non-nicotine e-vapor device 500 and/or pod 300, and output the measured airflow to the adaptive power level setting operation 2642.

Further, according to at least some example embodiments, during the ON vaping mode state, the adaptive power level setting operation 2642 may output a second power waveform 2720 based on both (i) the transfer curve output by the first transfer curve selection operation 2620 and (ii) measured airflow output by the heating engine sensors 2222 and/or pod sensors 2220. For example, the adaptive power level setting operation 2642 may generate an adapted power level by performing a mathematical operation on the power level corresponding to the output transfer curve, such that a value of the adapted power level increases as the measured airflow increases. For example, FIG. 25D illustrates an example relationship between detected airflow and an adapted power level generated by the adaptive heating engine control algorithm 2300B according to at least some example embodiments. As is illustrated in FIG. 25D, the adapted power level increases as the measured airflow increases. In the example shown in FIG. 25D, the adaptive power level setting operation 2642 is configured such that a relationship between the adapted power level and the measured airflow is substantially linear. However, at least some example embodiments are not limited to the example shown in FIG. 25D. For example, according to at least some example embodiments, the adaptive power level setting operation 2642 may be configured such that a relationship between the adapted power level and the measured airflow is not linear. According to at least some example embodiments, a relationship between the adapted power level and the measured airflow (i.e., the manner in which the generated adapted power level changes as the measured airflow changes) may be set in accordance with preferences of a designer or manufacturer of the non-nicotine e-vapor device 500 and/or pod 300.

Accordingly, the adaptive heating engine control algorithm 2300B controls an amount of power applied to the heating engine 2215 such that the amount of power applied to the heating engine 2215, and thus, a temperature and/or volume of vapor generated by the non-nicotine e-vapor device 500 and/or pod 300, varies as airflow through the non-nicotine e-vapor device 500 and/or pod 300 varies. Consequently, a temperature and/or volume of vapor generated by the non-nicotine e-vapor device 500 may be adjusted by adjusting an airflow of air through the non-nicotine e-vapor device 500 and/or pod 300.

Additionally, the decrement time operation 2610 of the adaptive heating engine control algorithm 2300B may operate in the same manner discussed above with reference to FIG. 25A, for example, by outputting a timer shutdown signal. Further, according to at least some example embodiments, the adaptive power level setting operation 2642 responds to the timer shutdown signal by outputting a power level or power level waveform to the heating engine driver 2305 that causes the heating engine driver 2305 to cut or cease the supply of power to the heating engine 2215. According to at least some example embodiments, in response to the adaptive power level setting operation 2642 receiving the timer shutdown signal from the decrement time operation 2610, the adaptive power level setting operation 2642 causes the heating engine driver 2305 to cut or cease the supply of power to the heating engine 2215 regardless of the transfer curve output by the first transfer curve selection operation 2620, and regardless of a measured airflow.

For ease of description, the adaptive heating engine control algorithm 2300B is discussed above, primarily, with reference to heating engine sensors 2222. However, according to at least some example embodiments, measurements discussed with reference to FIGS. 25C and 25D as being performed by heating engine sensors 2222 may also be performed by pod sensors 2220 or device sensors 2125. Further, for ease of description, the process of generating an adapted power level that varies in accordance with measured airflow is described above with reference to a heating engine control algorithm (i.e. adaptive heating engine control algorithm 2300B) which is a modification of the setpoint heating engine control algorithm 2300A of FIG. 25A. However, according to at least some example embodiments, the heating engine control algorithms 2300, 2300C and 2300D may also be modified to generate a power level waveform having adapted power levels that vary in accordance with measured airflow in the same manner discussed above with respect to FIG. 25C.

The temperature heating engine control algorithm 2300C will now be discussed below with reference to FIGS. 25E-25F.

Example Temperature Heating Engine Control Algorithm

Figure 25E:
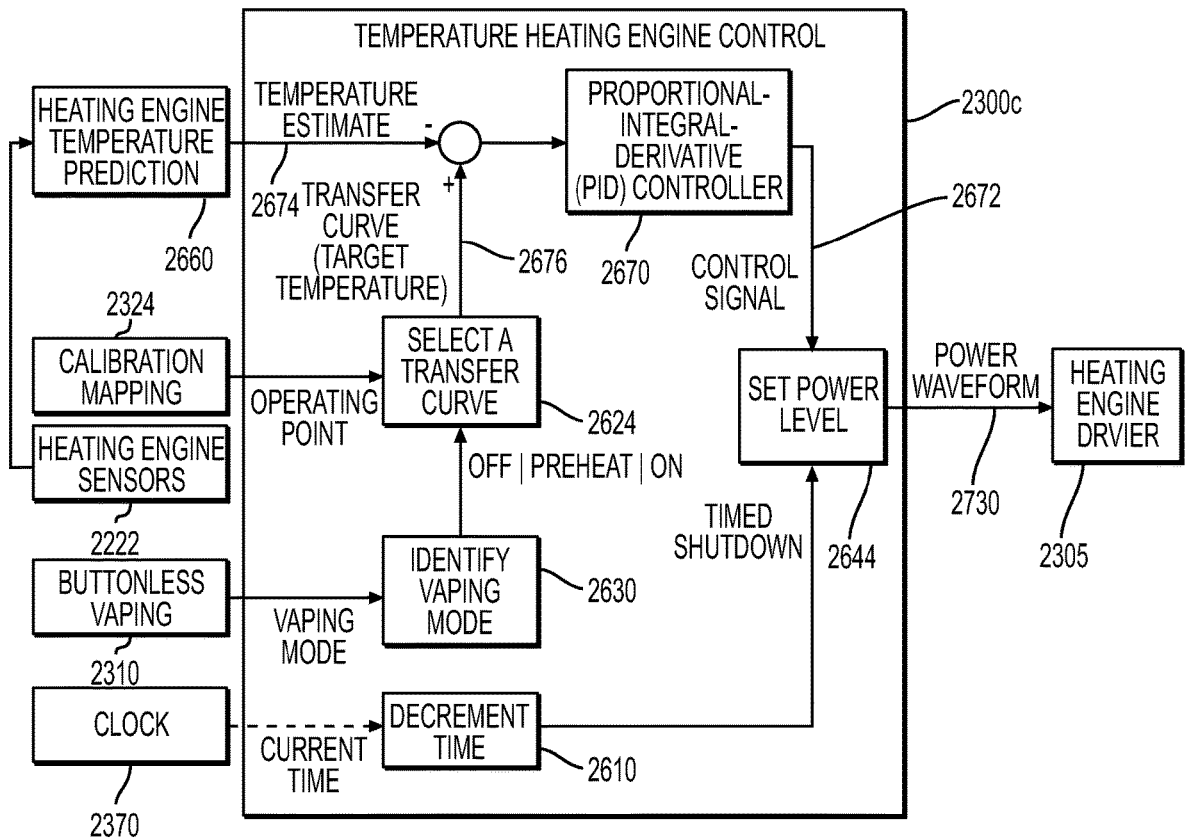
FIG. 25E is a block diagram illustrating a temperature heating engine control algorithm according to at least some example embodiments.

FIG. 25E is a block diagram illustrating the temperature heating engine control algorithm 2300C according to at least some example embodiments. According to at least some example embodiments, the temperature heating engine control algorithm 2300C is an example implementation of the heating engine control algorithm 2300 illustrated in FIG. 24.

According to at least some example embodiments, the temperature heating engine control algorithm 2300C is implemented by the controller 2105 of the device system 2100 included in a non-nicotine e-vapor device (e.g., non-nicotine e-vapor device 500). Thus, any or all operations described herein as being performed by the temperature heating engine control algorithm 2300C (or, an element thereof) may be performed by the controller 2105.

Referring to FIG. 25E, the temperature heating engine control algorithm 2300C uses a proportional-integral-derivative (PID) controller 2670 to control an amount of power applied to the heating engine 2215 so as to achieve a desired temperature. For example, as is discussed in greater detail below, according to at least some example embodiments, the temperature heating engine control algorithm 2300C includes determining a heater temperature value (e.g., heating engine temperature estimate 2674); obtaining a target temperature value (e.g., target temperature 2676); and controlling, by a PID controller (e.g., PID controller 2670), a level of power provided to the heater, based on the heater temperature value and the target temperature value.

A second calibration mapping function 2324 of the temperature heating engine control algorithm 2300C may differ from the first calibration mapping function 2320 of the setpoint heating engine control algorithm 2300A of FIG. 25A in that the second calibration mapping function 2324 may output operating points in the form of temperature values instead of power levels. For example, according to at least some example embodiments, the second calibration mapping function 2324 may read temperature values from the pod 300 or, alternatively, read operating points expressed as power values from the pod 300 and translate the operating points into temperature values. Accordingly, the second calibration mapping function 2324 may output a plurality of temperature values corresponding, respectively, to the plurality of vaping mode states: OFF, PREHEAT and ON. Further, in the same manner discussed above with respect to the operating points output by the first calibration mapping function 2320, the second calibration mapping function 2324 may select which temperature values to output with respect to one or more of the OFF, PREHEAT and ON vaping mode states based on one or both of a coarse preference level and fine preference level received from the AV vaping profile update function 2340.

Accordingly, a second transfer curve selection operation 2624 of the temperature heating engine control algorithm 2300C selects, from among the temperature values output by the second calibration mapping function 2324, a temperature value corresponding to the vaping mode state output by the vaping mode identification operation 2630. Further, the second transfer curve selection operation 2624 outputs the selected temperature value as target temperature 2676.

Consequently, according to at least some example embodiments, the temperature heating engine control algorithm 2300C obtains a target temperature value (e.g., target temperature 2676) by detecting, from the removable pod 300 included in the non-nicotine e-vapor device 500, power information indicating a plurality of temperature setpoints; determining a current operation mode of the non-nicotine e-vaping device 500 (e.g., the vaping mode state output by the vaping mode identification operation 2630); and selecting, as the target temperature value, a temperature setpoint, from among a plurality of temperature setpoints, that corresponds to the determined current operation mode of the non-nicotine e-vaping device 500.

Further, according to at least some example embodiments, the target temperature 2676 serves as a setpoint (i.e., a temperature setpoint) in a PID control loop controlled by the PID controller 2670. Other elements of the PID control loop controlled by the PID controller 2670 are as follows: a power control signal 2672 output by the PID controller 2670 to a second power level setting operation 2644 for controlling the levels of a third power waveform 2730 output by the second power level setting operation 2644 serves as the control variable of the PID control loop, and a heating engine temperature estimate 2674 output by the heating engine temperature prediction function 2660 serves and the process variable of the PID control loop.

As is discussed above, according to at least some example embodiments, the heating engine temperature estimate 2674 is output by the heating engine temperature prediction function 2660. For example, according to at least some example embodiments, the heating engine temperature prediction function 2660 may receive electrical measurements from the heating engine sensors 2222 indicating, for example, a current of the heater 2215, heater current heater_I; a voltage of the heater 2215, heater voltage heater_V; or other electrical attributes of the heater 2215 from which the heater current heater_I and/or heater voltage heater_V can be derived or estimated. Further, the heating engine temperature prediction function 2660 may use the electrical measurements of the heater 2215 to determine a resistance of the heater 2215, heater resistance heater_R (e.g., using Ohm's law or other known methods). For example, according to at least some example embodiments, the heating engine temperature prediction function 2660 may determine the quotient resulting from dividing the heater voltage heater_V by the heater current heater_I to be the heater resistance heater_R (i.e., heater_V/heater_I=heater_R).

Additionally, the non-nicotine e-vapor device 500 may store (e.g., in the storage medium 2145 of device system 2100 or the non-volatile memory 2205b of the pod system 2200) a look-up table (LUT) that stores a plurality of heater resistance values as indexes for a plurality of respectively corresponding heater temperature values also stored in the LUT. Consequently, the heating engine temperature prediction function 2660 may estimate a current temperature of the heater 2215 by using the previously determined heater resistance heater_R as an index for the LUT to identify (e.g., look-up) a corresponding heater temperature heater_T from among the heater temperatures stored in the LUT. According to at least some example embodiments, the heating engine temperature prediction function 2660 may output the heater temperature heater_T identified from the LUT as the heating engine temperature estimate 2674.

Consequently, the PID controller 2670 continuously corrects a level of the power control signal 2672 so as to control the third power waveform 2730 output by the second power level setting operation 2644 to the heating engine driver 2305 in such a manner that a difference (e.g., a magnitude of the difference) between the target temperature 2676 and the heating engine temperature estimate 2674 is reduced or, alternatively, minimized. The difference between the target temperature 2676 and the heating engine temperature estimate 2674 may also be viewed as an error value which the PID controller 2670 works to reduce or minimize. For example, according to at least some example embodiments, the second power level setting operation 2644 outputs the third power waveform 2730 such that levels of the third power waveform 2730 are controlled by the power control signal 2672. Further, as was discussed above with reference to FIG. 25B, the heating engine driver 2305 causes an amount of power provided to the heater 2215 by the power supply 2110 to increase or decrease in manner that is proportional to an increase or decrease in a magnitude of the power levels of a power level waveform output to the heating engine driver 2305. Consequently, by controlling the power control signal 2672 in the manner discussed above, the PID controller 2670 controls a level of power provided to the heater 2215 (e.g., by the power supply 2110 of the non-nicotine e-vapor device 500) such that a magnitude of the difference between a target temperature value (e.g., target temperature 2676) and a heater temperature value (e.g., heating engine temperature estimate 2674) is reduced, or alternatively, minimized.

Figure 25F:
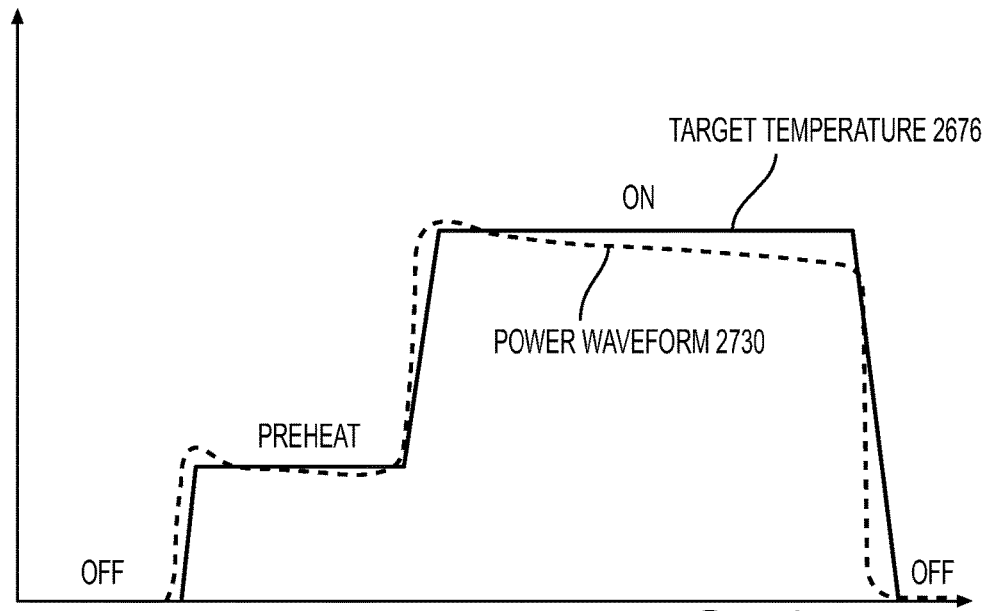
FIG. 25F illustrates an example of at least a portion of power level waveform generated by the temperature heating engine control algorithm of FIG. 25E according to at least some example embodiments.

For example, FIG. 25F illustrates an example of at least a portion of power level waveform generated by the temperature heating engine control algorithm of 2300C according to at least some example embodiments. FIG. 25 shows an example manner in which levels of the third power waveform 2730 may vary over time as the PID controller 2670 continuously corrects the power control signal 2672 provided to the second power level setting operation 2644. FIG. 25 shows an example manner in which levels of the third power waveform 2730 may vary as a vaping mode state output from the buttonless vaping function 2310 and/or the vaping mode identification operation 2630 transitions in accordance with the following sequence, OFF→PRE-HEAT→ON→OFF.

Returning to FIG. 25E, according to at least some example embodiments, the PID controller 2670 may operate in accordance with known PID control methods. According to at least some example embodiments, the PID controller 2670 may generate 2 or more terms from among the proportional term (P), the integral term (I), and the derivative term (D), and the PID controller 2670 may use the two or more terms adjust or correct the power control signal 2672 in accordance with known methods.

According to at least some example embodiments, the pod 300 may store PID parameters for calibrating the PID controller 2670, and the non-nicotine e-vapor device 500 may calibrate the PID controller 2670 based on the stored parameters. For example, PID parameters stored on the pod 300 may include any or all of a proportional gain $K_p$, an integral gain $K_i$, and a derivative gain $K_d$. PID parameters stored on the pod 300 may further include any other known PID controller parameters. According to at least some example embodiments, the PID parameters stored on the pod 300 may be chosen (e.g., by a designer or manufacturer of the pod 300) to correspond to characteristics of a formulation type of the non-nicotine pre-vapor formulation contained within the pod 300. Accordingly, pods with non-nicotine pre-vapor formulations of different formulation types may have different PID parameters stored in or on the pod, and thus, the operation of the PID controller 2670 may be tailored to characteristics of each different formulation type.

Additionally, the decrement time operation 2610 of the temperature heating engine control algorithm of 2300C may operate in the same manner discussed above with reference to FIG. 25A, for example, by outputting a timer shutdown signal. Further, according to at least some example embodiments, the second power level setting operation 2644 responds to the timer shutdown signal by outputting a power level or power level waveform to the heating engine driver 2305 that causes the heating engine driver 2305 to cut or cease the supply of power to the heating engine 2215. According to at least some example embodiments, in response to the second power level setting operation 2644 receiving the timer shutdown signal from the decrement time operation 2610, the second power level setting operation 2644 causes the heating engine driver 2305 to cut or cease the supply of power to the heating engine 2215 regardless of the power control signal 2672 output by the first transfer curve selection operation 2620.

The waveform heating engine control algorithm 2300D will now be discussed below with reference to FIGS. 25G-25H.

Example Waveform Heating Engine Control Algorithm

Figure 25G:
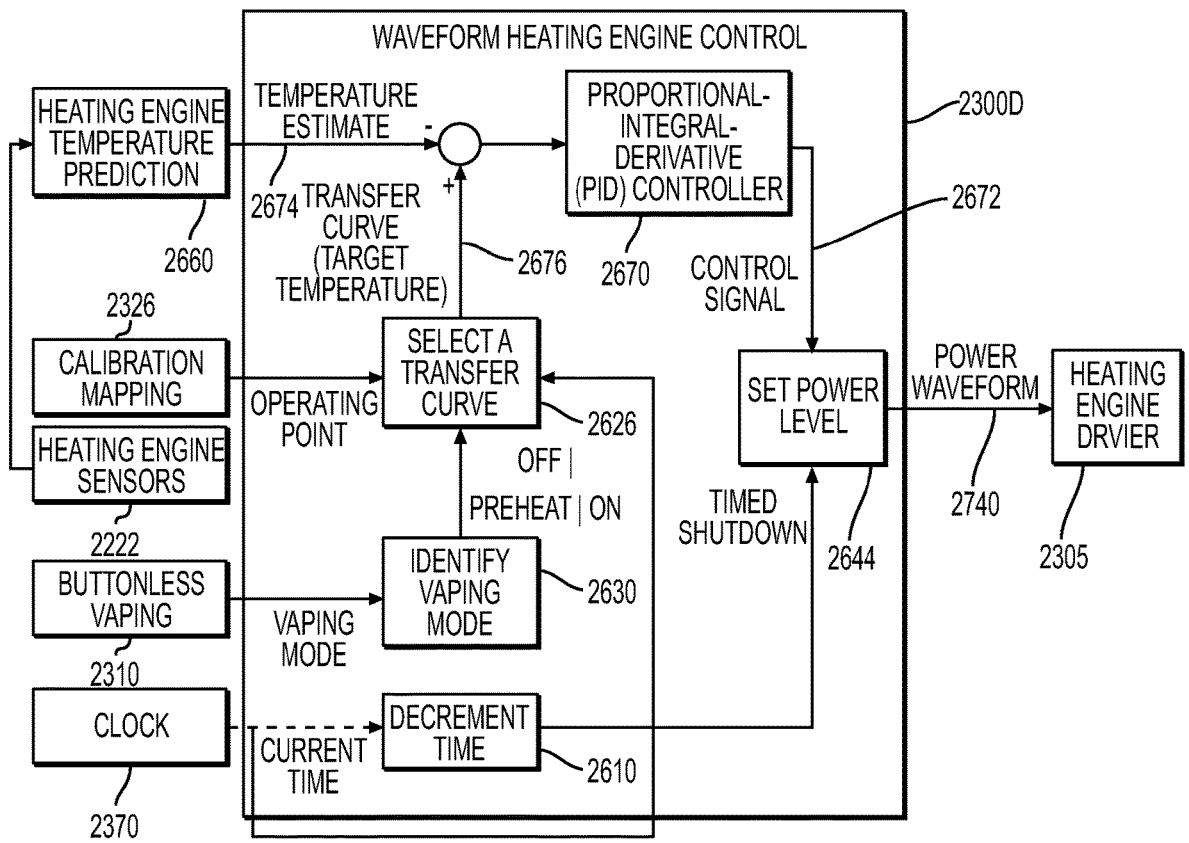
FIG. 25G is a block diagram illustrating a waveform heating engine control algorithm according to at least some example embodiments.
Figure 25H:
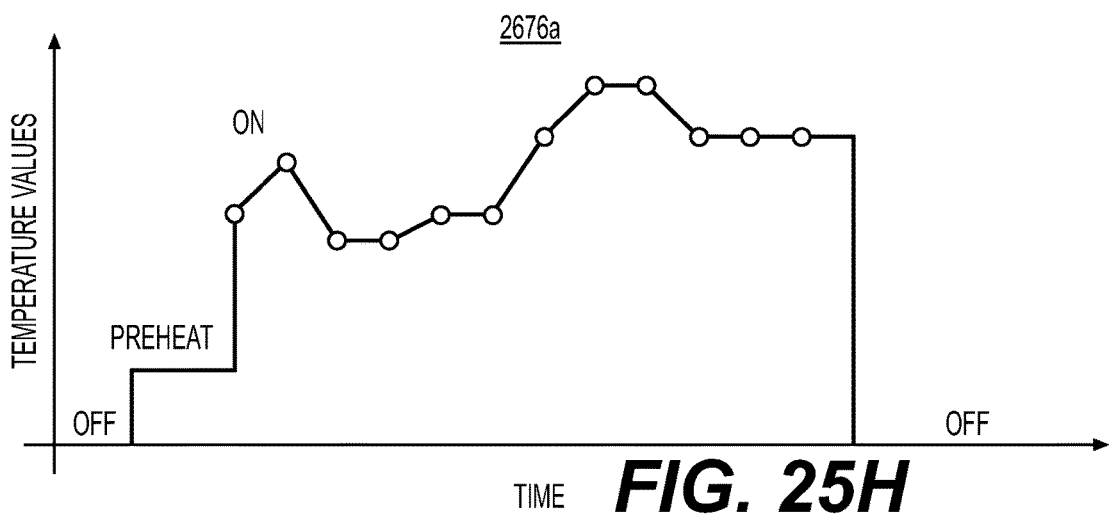
FIG. 25H illustrates an example of at least a portion of a temperature value waveform generated by the waveform heating engine control algorithm of FIG. 25G according to at least some example embodiments.

FIG. 25G is a block diagram illustrating the waveform heating engine control algorithm 2300D according to at least some example embodiments. According to at least some example embodiments, the waveform heating engine control algorithm 2300D is an example implementation of the heating engine control algorithm 2300 illustrated in FIG. 24.

According to at least some example embodiments, the waveform heating engine control algorithm 2300D is implemented by the controller 2105 of the device system 2100 included in a non-nicotine e-vapor device (e.g., non-nicotine e-vapor device 500). Thus, any or all operations described herein as being performed by the waveform heating engine control algorithm 2300D (or, an element thereof) may be performed by the controller 2105.

According to at least some example embodiments, the waveform heating engine control algorithm 2300D may control the power applied to the heater 2215 (e.g., by power supply 2110) during the ON vaping mode state so as to achieve a specified sequence (i.e., waveform) of heater temperatures, thereby resulting in a specified sequence of temperatures and/or volumes of vapor generated by the non-nicotine e-vapor device 500 and/or pod 300.

Referring to FIG. 25G, according to at least some example embodiments, the waveform heating engine control algorithm 2300D may be the same or substantially the same as the temperature heating engine control algorithm 2300C of FIG. 25E with the exception that in that the waveform heating engine control algorithm 2300D may include a third calibration mapping function 2326 and a third transfer curve selection operation 2626 instead of the second calibration mapping function 2324 and the second transfer curve selection operation 2624.

The third calibration mapping function 2326 may operate in the same manner discussed above with respect to the second calibration mapping function 2324 of FIG. 25E, with the exception that, instead out outputting one temperature value corresponding to the ON vaping mode state, the third calibration mapping function 2326 outputs a waveform including several temperature values.

Further, the third transfer curve selection operation 2626 may operate in the same manner discussed above with respect to the second transfer curve selection operation 2624 of FIG. 25E, with the exception that, instead out outputting one target temperature 2676 corresponding to the ON vaping mode state, the third transfer curve selection operation 2626 outputs a waveform including several target temperatures 2676, as is shown in FIG. 25H.

FIG. 25H illustrates an example of at least a portion of a target temperature waveform 2676A generated by the waveform heating engine control algorithm 2300D according to at least some example embodiments. The target temperature waveform 2676A illustrated in FIG. 25H shows target temperatures 2676 output by the third transfer curve selection operation 2626 over time. For example, according to at least some example embodiments, the target temperature waveform 2676A corresponds to the waveform of temperature values output by the third calibration mapping function 2326 as discussed above. Further, as is shown in FIG. 25G, the third transfer curve selection operation 2626 may receive a current time from clock 2370. Accordingly, the third transfer curve selection operation 2626 may use the current time to transition between each consecutive, individual values of the target temperature waveform 2676A in accordance with a time interval, as is shown by the white dots illustrated in FIG. 25H.

According to at least some example embodiments, a calibration mapping function (e.g., the first calibration mapping function 2320) may read and output a waveform of operating points (i.e., power values) in the same manner discussed above with respect to the wave form of temperature values output by the third calibration mapping function 2326. According to at least some example embodiments, a transfer curve selection operation (e.g., the first transfer curve selection operation 2620 of the setpoint heating engine control algorithm 2300A) may output power level waveform that includes several different power levels for the ON vaping mode state, in the same manner discussed above with respect to the several target temperatures corresponding to the ON vaping mode state in the target temperature waveform 2676A output by the third transfer curve selection operation 2626.

According to at least some example embodiments, a shape of a waveform of temperature values or operating points read by a calibration mapping function from the pod (e.g., pod 300) may be set (e.g., by a designer or manufacturer of the pod) in accordance with characteristics of a formulation type of the non-nicotine pre-vapor formulation contained within the pod. Accordingly, pods with different non-nicotine pre-vapor formulations of different formulation types may have different temperature value waveforms or operating point waveforms stored in or on the pod.

Further, according to at least some example embodiments, the device body 100 may store one or more waveforms. For example, the one or more waveforms may be stored on the device body 100 as sequences of offsets to be applied to a temperature value or operating point (e.g., a single temperature value or operating point) output by a calibration mapping function (e.g., the third calibration mapping function 2326) with respect to the ON vaping mode state. For example, a transfer curve selection operation (e.g., the third transfer curve selection operation 2626) may read one the one or more waveforms stored on the device body 100, and apply the offsets corresponding to the read waveform to the ON-state temperature value or operating point output by the calibration mapping function in order to generate a target temperature waveform or power waveform having several different values with respect to the ON vaping mode, like the target temperature waveform 2676A illustrated in FIG. 25H.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. A method of controlling a heater of a non-nicotine e-vaping device, the non-nicotine e-vaping device including a removable container that stores a non-nicotine pre-vapor formulation, the method comprising:
   detecting, from the removable container, power information indicating a first operating point and a second operating point, the power information including a plurality of operating points that correspond, respectively, to a plurality of coarse preference levels, the plurality of operating points including the first operating point and the second operating point;
   receiving, via one or more touch sensors located on the non-nicotine e-vaping device, a selection of a coarse preference level from among the plurality of coarse preference levels;

selecting an operating point from among the plurality of operating points that corresponds to the selected coarse preference level as the second operating point; and supplying power to the heater based on the detected power information by, determining a first amount of power based on the first operating point, supplying the first amount of power to the heater during a first operation mode of the heater, determining a second amount of power based on the second operating point, and supplying the second amount of power to the heater during a second operation mode of the heater, the second amount of power being higher than the first amount of power.

2. The method of claim 1, wherein, the first amount of power supplied during the first operation mode is an amount that causes the heater to heat the non-nicotine pre-vapor formulation stored in the non-nicotine e-vaping device to a temperature below a boiling point of the non-nicotine pre-vapor formulation, and the second amount of power supplied during the second operation mode is an amount that causes the heater to heat the non-nicotine pre-vapor formulation stored in the non-nicotine e-vaping device to a temperature equal to, or greater than, the boiling point of the non-nicotine pre-vapor formulation.

3. The method of claim 2, wherein the non-nicotine pre-vapor formulation is stored in the removable container.

4. The method of claim 2, wherein the removable container includes the heater.

5. The method of claim 1, wherein the determining of the second amount of power comprises:

receiving, by the non-nicotine e-vaping device from an external source, a selection of a fine preference level, from among a plurality of fine preference levels; and determining the second amount of power based on the second operating point and the selected fine preference level.

6. The method of claim 5, wherein the external source is a wireless communication device, and the receiving of the selection of the fine preference level comprises:

receiving, by the non-nicotine e-vaping device, the selection of the fine preference level via a wireless communication link between the non-nicotine e-vaping device and the external source.

7. The method of claim 1, wherein the plurality of operating points includes a first plurality of operating points, and the method further comprises:

receiving, via the one or more touch sensors located on the non-nicotine e-vaping device, a selection of a second coarse preference level, from among the plurality of coarse preference levels; and selecting an operating point, from among the first plurality of operating points, that corresponds to the selected second coarse preference level as the first operating point.

8. The method of claim 7, wherein the determining of the first amount of power comprises:

receiving, by the non-nicotine e-vaping device from an external source, a selection of a fine preference level from among a plurality of fine preference levels; and determining the first amount of power based on the first operating point and the selected fine preference level.

9. The method of claim 8, wherein the external source is a wireless communication device, and the receiving of the selection of the fine preference level comprises:

receiving, by the non-nicotine e-vaping device, the selection of the fine preference level via a wireless communication link between the non-nicotine e-vaping device and the external source.

10. The method of claim 8, wherein the plurality of operating points further includes a second plurality of operating points, and the selecting the operating point from among the plurality of operating points includes selecting the operating point from the second plurality of operating points.

11. The method of claim 10, wherein the determining of the second amount of power comprises:

determining the second amount of power based on the second operating point and the selected fine preference level.

12. The method of claim 11, wherein the external source is a wireless communication device, and the receiving of the selection of the fine preference level comprises:

receiving, by the non-nicotine e-vaping device, the selection of the fine preference level via a wireless communication link between the non-nicotine e-vaping device and the external source.

13. The method of claim 1, wherein the detecting of the power information comprises:

reading, by the non-nicotine e-vaping device, the power information from an image located on the removable container.

14. The method of claim 13, wherein the image includes a QR code, and the reading of the power information comprises:

reading, by the non-nicotine e-vaping device, the power information from the QR code located on the removable container.

15. The method of claim 1, wherein, the detecting of the power information comprises:

reading, by the device, the power information from a memory of the removable container.

16. A method of controlling a heater of a heat-not-burn aerosol-generating device, the heat-not-burn aerosol-generating device including a removable container that stores an aerosol-forming substrate, the method comprising:

detecting, from the removable container, power information indicating a first operating point and a second operating point, the power information including a plurality of operating points that correspond, respectively, to a plurality of coarse preference levels, the plurality of operating points including the first operating point and the second operating point;

receiving, via one or more touch sensors located on the heat-not-burn aerosol-generating device, a selection of a coarse preference level from among the plurality of coarse preference levels;

selecting an operating point from among the plurality of operating points that corresponds to the selected coarse preference level as the second operating point; and supplying power to the heater based on the detected power information by, determining a first amount of power based on the first operating point, supplying the first amount of power to the heater during a first operation mode of the heater, determining a second amount of power based on the second operating point, and supplying the second amount of power to the heater during a second operation mode of the heater, the second amount of power being higher than the first amount of power.

17. The method of claim 16, wherein, the first amount of power supplied during the first operation mode is an amount that causes the heater to heat the aerosol-forming substrate stored in the heat-not-burn aerosol-generating device to a temperature below an aerosolization temperature of the aerosol-forming substrate, and the second amount of power supplied during the second operation mode is an amount that causes the heater to heat the aerosol-forming substrate stored in the heat-not-burn aerosol-generating device to a temperature equal to, or greater than, the aerosolization temperature of the aerosol-forming substrate.

18. The method of claim 16, wherein the power information includes a plurality of operating points that correspond, respectively, to a plurality of coarse preference levels, and the method further comprises:

receiving, via one or more touch sensors located on the heat-not-burn aerosol-generating device, a selection of a coarse preference level, from among the plurality of coarse preference levels; and selecting, as the second operating point, the operating point, from among the plurality of operating points, that corresponds to the selected coarse preference level.

19. The method of claim 16, wherein the plurality of operating points includes a first plurality of operating points, and the method further comprises:

receiving, via the one or more touch sensors located on the heat-not-burn aerosol-generating device, a selection of a second coarse preference level, from among the plurality of coarse preference levels; and selecting, as the first operating point, an operating point, from among the first plurality of operating points, that corresponds to the selected second coarse preference level.

20. The method of claim 16, wherein the detecting of the power information comprises:

reading, by the heat-not-burn aerosol-generating device, the power information from an image located on the removable container.

21. The method of claim 16, wherein, the detecting of the power information comprises:

reading, by the heat-not-burn aerosol-generating device, the power information from memory of the removable container.

* * * * *